US012594416B2

(12) United States Patent
Tuval et al.

(10) Patent No.: US 12,594,416 B2
(45) Date of Patent: Apr. 7, 2026

(54) VENA CAVAL OCCLUSION

(71) Applicant: MAGENTA MEDICAL LTD, Kadima (IL)

(72) Inventors: Yosi Tuval, Even Yehuda (IL); Ehud Schwammenthal, Ra'anana (IL); Daniel Glozman, Kfar Yona (IL); Gad Lubinsky, Ein Vered (IL)

(73) Assignee: MAGENTA MEDICAL LTD, Kadima (IL)

( * ) Notice: Subject to any disclaimer, the term of this patent is extended or adjusted under 35 U.S.C. 154(b) by 0 days.

(21) Appl. No.: 18/767,628

(22) Filed: Jul. 9, 2024

(65) Prior Publication Data

US 2024/0359001 A1 Oct. 31, 2024

Related U.S. Application Data

(63) Continuation of application No. 18/130,698, filed on Apr. 4, 2023, now Pat. No. 12,133,978, which is a
(Continued)

(51) Int. Cl.
*A61M 60/833* (2021.01)
*A61M 60/13* (2021.01)
(Continued)

(52) U.S. Cl.
CPC .......... *A61M 60/833* (2021.01); *A61M 60/13* (2021.01); *A61M 60/139* (2021.01);
(Continued)

(58) Field of Classification Search
CPC .. A61M 60/833; A61M 60/13; A61M 60/139; A61M 60/531; A61M 60/585; A61M 60/237
See application file for complete search history.

(56) References Cited

U.S. PATENT DOCUMENTS 4,822,345 A 4/1989 Danforth
4,886,506 A 12/1989 Lovgren et al.
(Continued)

FOREIGN PATENT DOCUMENTS

AU 2013205145 A1 5/2013
AU 2013257469 B2 3/2016
(Continued)

OTHER PUBLICATIONS

Final Office Action for U.S. Appl. No. 18/510,983 mailed Mar. 11, 2025.
(Continued)

*Primary Examiner* — Catherine M Voorhees
(74) *Attorney, Agent, or Firm* — Ballard Spahr LLP

(57) ABSTRACT
Apparatus and methods are described including reducing cardiac preload of a subject by partially occluding a vena cava of the subject at an infra-renal location. One or more physiological parameters of the subject are monitored, the one or more physiological parameters including lower body venous pressure, central venous pressure, central venous blood flow, renal venous pressure, cardiac diameter, cardiac volume, arterial pressure, and/or arterial blood flow. An extent to which the vena cava is occluded at the infra-renal location is modulated, responsively to the one or more physiological parameters. Other applications are also described.

17 Claims, 34 Drawing Sheets

Related U.S. Application Data continuation of application No. 17/320,742, filed on May 14, 2021, now Pat. No. 11,648,392, which is a continuation of application No. 16/345,389, filed as application No. PCT/IL2017/051273 on Nov. 21, 2017, now Pat. No. 11,033,727.

(60) Provisional application No. 62/425,814, filed on Nov. 23, 2016.

(51) Int. Cl.

| | |
|---|---|
| *A61M 60/139* | (2021.01) |
| *A61M 60/216* | (2021.01) |
| *A61M 60/416* | (2021.01) |
| *A61M 60/531* | (2021.01) |
| *A61M 60/585* | (2021.01) |
| *A61M 60/804* | (2021.01) |
| *A61M 60/818* | (2021.01) |
| *A61M 60/414* | (2021.01) |

(52) U.S. Cl.
CPC ........ *A61M 60/216* (2021.01); *A61M 60/416* (2021.01); *A61M 60/531* (2021.01); *A61M 60/585* (2021.01); *A61M 60/804* (2021.01); *A61M 60/818* (2021.01); *A61M 60/414* (2021.01)

(56) References Cited

U.S. PATENT DOCUMENTS

| | | | |
|---|---|---|---|
| 4,919,647 | A | 4/1990 | Nash |
| 4,954,055 | A | 9/1990 | Raible et al. |
| 5,040,944 | A | 8/1991 | Cook |
| 5,300,112 | A | 4/1994 | Barr |
| 5,613,935 | A | 3/1997 | Jarvik |
| 5,713,730 | A | 2/1998 | Nose et al. |
| 5,749,855 | A | 5/1998 | Reitan |
| 5,772,693 | A | 6/1998 | Brownlee |
| 5,876,385 | A | 3/1999 | Ikari et al. |
| 5,964,694 | A | 10/1999 | Siess et al. |
| 6,086,527 | A | 7/2000 | Talpade |
| 6,135,729 | A | 10/2000 | Aber |
| 6,136,025 | A | 10/2000 | Barbut et al. |
| 6,176,848 | B1 | 1/2001 | Rau et al. |
| 6,183,220 | B1 | 2/2001 | Ohara et al. |
| 6,247,892 | B1 | 6/2001 | Kazatchkov et al. |
| 6,482,228 | B1 | 11/2002 | Norred |
| 6,533,716 | B1 | 3/2003 | Schmutz-Rode et al. |
| 6,592,567 | B1 | 7/2003 | Levin et al. |
| 6,616,624 | B1 | 9/2003 | Kieval |
| 6,884,210 | B2 | 4/2005 | Nose et al. |
| 7,004,925 | B2 | 2/2006 | Navia et al. |
| 7,011,620 | B1 | 3/2006 | Siess |
| 7,070,555 | B2 | 7/2006 | Siess |
| 7,144,364 | B2 | 12/2006 | Barbut et al. |
| 7,159,593 | B2 | 1/2007 | Mccarthy et al. |
| 7,201,772 | B2 | 4/2007 | Schwammenthal et al. |
| 7,335,192 | B2 | 2/2008 | Keren et al. |
| 7,341,570 | B2 | 3/2008 | Keren et al. |
| 7,485,104 | B2 | 2/2009 | Kieval |
| 7,717,952 | B2 | 5/2010 | Case et al. |
| 7,744,642 | B2 | 6/2010 | Rittgers et al. |
| 7,762,941 | B2 | 7/2010 | Jarvik |
| 7,766,853 | B2 | 8/2010 | Lane |
| 7,766,892 | B2 | 8/2010 | Keren et al. |
| 7,766,961 | B2 | 8/2010 | Patel et al. |
| 7,780,628 | B1 | 8/2010 | Keren et al. |
| 7,811,221 | B2 | 10/2010 | Gross |
| 7,841,976 | B2 | 11/2010 | McBride et al. |
| 7,914,503 | B2 | 3/2011 | Goodson et al. |
| 7,927,068 | B2 | 4/2011 | Mcbride et al. |
| 8,007,254 | B2 | 8/2011 | Larose et al. |
| 8,012,121 | B2 | 9/2011 | Goodson et al. |
| 8,079,948 | B2 | 12/2011 | Shifflette |
| 8,221,492 | B2 | 7/2012 | Case et al. |
| 8,235,933 | B2 | 8/2012 | Keren et al. |
| 8,277,470 | B2 | 10/2012 | Demarais et al. |
| 8,376,707 | B2 | 2/2013 | Mcbride et al. |
| 8,449,443 | B2 | 5/2013 | Rodefeld et al. |
| 8,512,262 | B2 | 8/2013 | Gertner |
| 8,538,535 | B2 | 9/2013 | Ariav et al. |
| 8,579,858 | B2 | 11/2013 | Reitan et al. |
| 8,617,239 | B2 | 12/2013 | Reitan |
| 8,684,904 | B2 | 4/2014 | Campbell et al. |
| 8,690,749 | B1 | 4/2014 | Nunez |
| 8,721,516 | B2 | 5/2014 | Scheckel |
| 8,721,517 | B2 | 5/2014 | Zeng et al. |
| 8,727,959 | B2 | 5/2014 | Reitan et al. |
| 8,734,331 | B2 | 5/2014 | Evans et al. |
| 8,734,508 | B2 | 5/2014 | Hastings et al. |
| 8,777,832 | B1 | 7/2014 | Wang et al. |
| 8,849,398 | B2 | 9/2014 | Evans |
| 8,992,163 | B2 | 3/2015 | Mcbride et al. |
| 9,028,216 | B2 | 5/2015 | Schumacher et al. |
| 9,067,006 | B2 | 6/2015 | Toellner |
| 9,089,634 | B2 | 7/2015 | Schumacher et al. |
| 9,138,518 | B2 | 9/2015 | Campbell et al. |
| 9,162,017 | B2 | 10/2015 | Evans et al. |
| 9,217,442 | B2 | 12/2015 | Wiessler et al. |
| 9,227,002 | B1* | 1/2016 | Giridharan .......... A61M 60/148 |
| 9,314,558 | B2 | 4/2016 | Er |
| 9,327,067 | B2 | 5/2016 | Zeng et al. |
| 9,339,596 | B2 | 5/2016 | Roehn |
| 9,358,329 | B2 | 6/2016 | Fitzgerald et al. |
| 9,393,384 | B1 | 7/2016 | Kapur et al. |
| 9,402,942 | B2 | 8/2016 | Hastie et al. |
| 9,416,783 | B2 | 8/2016 | Schumacher et al. |
| 9,572,915 | B2 | 2/2017 | Heuring et al. |
| 9,597,205 | B2 | 3/2017 | Tuval |
| 9,675,740 | B2 | 6/2017 | Zeng et al. |
| 9,750,860 | B2 | 9/2017 | Schumacher |
| 9,750,861 | B2 | 9/2017 | Hastie et al. |
| 9,764,113 | B2 | 9/2017 | Tuval et al. |
| 9,771,801 | B2 | 9/2017 | Schumacher et al. |
| 9,895,475 | B2 | 2/2018 | Toellner et al. |
| 9,903,384 | B2 | 2/2018 | Roehn |
| 9,907,891 | B2 | 3/2018 | Wiessler et al. |
| 9,913,937 | B2 | 3/2018 | Schwammenthal et al. |
| 9,964,115 | B2 | 5/2018 | Scheckel |
| 10,039,874 | B2 | 8/2018 | Schwammenthal et al. |
| 10,052,419 | B2 | 8/2018 | Er |
| 10,107,299 | B2 | 10/2018 | Scheckel |
| 10,172,985 | B2 | 1/2019 | Simon et al. |
| 10,179,197 | B2 | 1/2019 | Kaiser et al. |
| 10,196,899 | B2 | 2/2019 | Toellner et al. |
| 10,207,037 | B2 | 2/2019 | Corbett et al. |
| 10,208,763 | B2 | 2/2019 | Schumacher et al. |
| 10,215,187 | B2 | 2/2019 | Mcbride et al. |
| 10,231,838 | B2 | 3/2019 | Chin et al. |
| 10,245,363 | B1* | 4/2019 | Rowe ................. A61M 60/216 |
| 10,299,701 | B2 | 5/2019 | Blanton et al. |
| 10,299,918 | B2 | 5/2019 | Tuval |
| 10,342,904 | B2 | 7/2019 | Schumacher |
| 10,342,906 | B2 | 7/2019 | D'ambrosio et al. |
| 10,363,350 | B2 | 7/2019 | Schwammenthal et al. |
| 10,413,646 | B2 | 9/2019 | Wiessler et al. |
| 10,478,538 | B2 | 11/2019 | Scheckel et al. |
| 10,478,539 | B2 | 11/2019 | Pfeffer et al. |
| 10,495,101 | B2 | 12/2019 | Scheckel |
| 10,557,475 | B2 | 2/2020 | Roehn |
| 10,583,231 | B2 | 3/2020 | Schwammenthal et al. |
| 10,584,589 | B2 | 3/2020 | Schumacher et al. |
| 10,589,012 | B2 | 3/2020 | Toellner et al. |
| 10,617,808 | B2 | 4/2020 | Hastie et al. |
| 10,662,967 | B2 | 5/2020 | Scheckel |
| 10,669,855 | B2 | 6/2020 | Toellner et al. |
| 10,765,789 | B2 | 9/2020 | Zeng et al. |
| 10,792,406 | B2 | 10/2020 | Roehn et al. |
| 10,799,624 | B2 | 10/2020 | Pfeffer et al. |
| 10,799,626 | B2 | 10/2020 | Siess et al. |
| 10,801,511 | B2 | 10/2020 | Siess et al. |
| 10,806,838 | B2 | 10/2020 | Er |

(56) References Cited

U.S. PATENT DOCUMENTS

| | | | |
|---|---|---|---|
| 10,835,653 B2 | 11/2020 | Liebing | |
| 10,857,272 B2 | 12/2020 | Liebing | |
| 10,864,309 B2 | 12/2020 | Mcbride et al. | |
| 10,864,310 B2 | 12/2020 | Schwammenthal et al. | |
| 10,865,801 B2 | 12/2020 | Mcbride et al. | |
| 10,874,783 B2 | 12/2020 | Pfeffer et al. | |
| 10,881,845 B2 | 1/2021 | Siess et al. | |
| 10,894,115 B2 | 1/2021 | Pfeffer et al. | |
| 10,898,629 B2 | 1/2021 | Siess et al. | |
| 10,905,808 B2 | 2/2021 | Tuval et al. | |
| 10,907,646 B2 | 2/2021 | Bredenbreuker et al. | |
| 10,920,596 B2 | 2/2021 | Toellner et al. | |
| 10,926,013 B2 | 2/2021 | Schumacher et al. | |
| 10,935,038 B2 | 3/2021 | Siess | |
| 10,980,927 B2 | 4/2021 | Pfeffer et al. | |
| 11,007,350 B2 | 5/2021 | Tao et al. | |
| 11,020,584 B2 | 6/2021 | Siess et al. | |
| 11,027,114 B2 | 6/2021 | D'ambrosio et al. | |
| 11,033,727 B2 | 6/2021 | Tuval et al. | |
| 11,033,729 B2 | 6/2021 | Scheckel et al. | |
| 11,040,187 B2 | 6/2021 | Wiessler et al. | |
| RE48,649 E | 7/2021 | Siess | |
| 11,116,960 B2 | 9/2021 | Simon et al. | |
| 11,123,539 B2 | 9/2021 | Pfeffer et al. | |
| 11,129,978 B2 | 9/2021 | Pfeffer et al. | |
| 11,167,124 B2 | 11/2021 | Pfeffer et al. | |
| 11,168,705 B2 | 11/2021 | Liebing | |
| 11,197,690 B2 | 12/2021 | Fantuzzi et al. | |
| 11,219,755 B2 | 1/2022 | Siess et al. | |
| 11,229,786 B2 | 1/2022 | Zeng et al. | |
| 11,253,692 B2 | 2/2022 | Schumacher | |
| 11,253,693 B2 | 2/2022 | Pfeffer et al. | |
| 11,260,215 B2 | 3/2022 | Scheckel et al. | |
| 11,266,824 B2 | 3/2022 | Er | |
| 11,268,521 B2 | 3/2022 | Toellner | |
| 11,273,301 B2 | 3/2022 | Pfeffer et al. | |
| 11,278,711 B2 | 3/2022 | Liebing | |
| 11,280,345 B2 | 3/2022 | Bredenbreuker et al. | |
| 11,291,824 B2 | 4/2022 | Schwammenthal et al. | |
| 11,298,525 B2 | 4/2022 | Jahangir | |
| 11,305,105 B2 | 4/2022 | Corbett et al. | |
| 11,313,228 B2 | 4/2022 | Schumacher et al. | |
| 11,338,124 B2 | 5/2022 | Pfeffer et al. | |
| 11,351,358 B2 | 6/2022 | Nix et al. | |
| 11,364,373 B2 | 6/2022 | Corbett et al. | |
| 11,421,701 B2 | 8/2022 | Schumacher et al. | |
| 11,434,922 B2 | 9/2022 | Roehn | |
| 11,484,701 B2 | 11/2022 | Schwammenthal et al. | |
| 11,648,387 B2 | 5/2023 | Schwammenthal et al. | |
| 11,648,391 B2 | 5/2023 | Schwammenthal et al. | |
| 11,648,392 B2 | 5/2023 | Tuval et al. | |
| 11,806,117 B2 | 11/2023 | Tuval et al. | |
| 11,883,274 B2 | 1/2024 | Schwammenthal et al. | |
| 12,128,228 B2 * | 10/2024 | Friedland | A61M 60/216 |
| 2002/0107536 A1 | 8/2002 | Hussein | |
| 2003/0055486 A1 | 3/2003 | Adams et al. | |
| 2003/0149473 A1 | 8/2003 | Chouinard et al. | |
| 2003/0208097 A1 | 11/2003 | Aboul-hosn et al. | |
| 2004/0064090 A1 | 4/2004 | Keren et al. | |
| 2004/0064091 A1 | 4/2004 | Keren et al. | |
| 2004/0111006 A1 | 6/2004 | Alferness et al. | |
| 2004/0116769 A1 | 6/2004 | Jassawalla et al. | |
| 2004/0167415 A1 | 8/2004 | Gelfand et al. | |
| 2004/0210236 A1 | 10/2004 | Allers et al. | |
| 2004/0219028 A1 | 11/2004 | Demarais et al. | |
| 2004/0260389 A1 | 12/2004 | Case et al. | |
| 2005/0033406 A1 | 2/2005 | Barnhart et al. | |
| 2005/0049692 A1 | 3/2005 | Numamoto et al. | |
| 2005/0055082 A1 | 3/2005 | Ben et al. | |
| 2005/0079274 A1 | 4/2005 | Palasis et al. | |
| 2005/0119682 A1 | 6/2005 | Nguyen et al. | |
| 2005/0137680 A1 | 6/2005 | Ortiz et al. | |
| 2006/0062672 A1 | 3/2006 | Mcbride et al. | |
| 2006/0064059 A1 | 3/2006 | Gelfand et al. | |
| 2006/0106449 A1 | 5/2006 | Ben | |
| 2006/0135961 A1 | 6/2006 | Rosenman et al. | |
| 2006/0245959 A1 | 11/2006 | LaRose et al. | |
| 2007/0100435 A1 | 5/2007 | Case et al. | |
| 2007/0162103 A1 | 7/2007 | Case et al. | |
| 2007/0208291 A1 | 9/2007 | Patel | |
| 2007/0213690 A1 * | 9/2007 | Phillips | A61M 1/3653 604/533 |
| 2007/0260327 A1 | 11/2007 | Case et al. | |
| 2007/0293808 A1 | 12/2007 | Williams et al. | |
| 2008/0103591 A1 | 5/2008 | Siess | |
| 2008/0114339 A1 | 5/2008 | Mcbride et al. | |
| 2008/0132748 A1 | 6/2008 | Shifflette | |
| 2008/0154236 A1 | 6/2008 | Elkins et al. | |
| 2008/0183280 A1 | 7/2008 | Agnew et al. | |
| 2009/0024195 A1 | 1/2009 | Rezai et al. | |
| 2009/0062597 A1 | 3/2009 | Shifflette | |
| 2009/0093796 A1 | 4/2009 | Pfeffer et al. | |
| 2009/0131785 A1 | 5/2009 | Lee et al. | |
| 2009/0264991 A1 | 10/2009 | Paul et al. | |
| 2009/0287299 A1 | 11/2009 | Tabor et al. | |
| 2009/0318857 A1 | 12/2009 | Goodson et al. | |
| 2010/0030259 A1 | 2/2010 | Pavcnik et al. | |
| 2010/0130810 A1 | 5/2010 | Mohl | |
| 2011/0004046 A1 | 1/2011 | Campbell et al. | |
| 2011/0106244 A1 | 5/2011 | Ferrari et al. | |
| 2011/0152999 A1 | 6/2011 | Hastings et al. | |
| 2011/0190874 A1 | 8/2011 | Celermajer et al. | |
| 2011/0213408 A1 | 9/2011 | Gross et al. | |
| 2011/0230949 A1 | 9/2011 | Haverkost et al. | |
| 2011/0257462 A1 | 10/2011 | Rodefeld et al. | |
| 2011/0264075 A1 | 10/2011 | Leung et al. | |
| 2011/0282128 A1 | 11/2011 | Reitan et al. | |
| 2011/0282274 A1 | 11/2011 | Fulton | |
| 2011/0301662 A1 | 12/2011 | Bar-yoseph et al. | |
| 2011/0319906 A1 | 12/2011 | Rudakov et al. | |
| 2012/0022579 A1 | 1/2012 | Fulton | |
| 2012/0059460 A1 | 3/2012 | Reitan | |
| 2012/0089047 A1 | 4/2012 | Ryba et al. | |
| 2012/0116382 A1 | 5/2012 | Ku et al. | |
| 2012/0130469 A1 | 5/2012 | Cragg et al. | |
| 2012/0172654 A1 | 7/2012 | Bates | |
| 2012/0224970 A1 | 9/2012 | Schumacher et al. | |
| 2012/0232457 A1 | 9/2012 | Kandarpa | |
| 2012/0237357 A1 | 9/2012 | Schumacher et al. | |
| 2012/0301318 A1 | 11/2012 | Er | |
| 2012/0328460 A1 | 12/2012 | Horvath et al. | |
| 2013/0053623 A1 | 2/2013 | Evans et al. | |
| 2013/0053732 A1 | 2/2013 | Heuser | |
| 2013/0079874 A1 | 3/2013 | Doss et al. | |
| 2013/0177409 A1 | 7/2013 | Schumacher et al. | |
| 2013/0177432 A1 | 7/2013 | Toellner et al. | |
| 2013/0237744 A1 | 9/2013 | Pfeffer et al. | |
| 2014/0018840 A1 | 1/2014 | Morgan et al. | |
| 2014/0025041 A1 | 1/2014 | Fukuoka et al. | |
| 2014/0051908 A1 | 2/2014 | Khanal et al. | |
| 2014/0128659 A1 | 5/2014 | Heuring et al. | |
| 2014/0275722 A1 | 9/2014 | Zimmermann et al. | |
| 2014/0275726 A1 | 9/2014 | Zeng | |
| 2014/0350658 A1 | 11/2014 | Benary et al. | |
| 2015/0018597 A1 | 1/2015 | Fierens et al. | |
| 2015/0119633 A1 | 4/2015 | Haselby et al. | |
| 2015/0141739 A1 | 5/2015 | Hsu et al. | |
| 2015/0157777 A1 | 6/2015 | Tuval et al. | |
| 2015/0164662 A1 | 6/2015 | Tuval | |
| 2015/0176582 A1 | 6/2015 | Liebing | |
| 2015/0343136 A1 | 12/2015 | Nitzan et al. | |
| 2015/0343186 A1 | 12/2015 | Nitzan et al. | |
| 2016/0022890 A1 | 1/2016 | Schwammenthal et al. | |
| 2016/0051741 A1 | 2/2016 | Schwammenthal et al. | |
| 2016/0053768 A1 | 2/2016 | Schumacher et al. | |
| 2016/0136343 A1 | 5/2016 | Anagnostopoulos | |
| 2016/0184500 A1 | 6/2016 | Zeng | |
| 2016/0279310 A1 | 9/2016 | Scheckel et al. | |
| 2017/0049946 A1 * | 2/2017 | Kapur | A61B 17/1204 |
| 2017/0071769 A1 | 3/2017 | Mangiardi | |
| 2017/0100527 A1 | 4/2017 | Schwammenthal et al. | |
| 2017/0197021 A1 | 7/2017 | Nitzan et al. | |
| 2018/0096531 A1 | 4/2018 | Greenhalgh et al. | |
| 2018/0126130 A1 | 5/2018 | Nitzan et al. | |

(56) References Cited

U.S. PATENT DOCUMENTS

| | | |
|---|---|---|
| 2018/0149165 A1 | 5/2018 | Siess et al. |
| 2018/0169313 A1 | 6/2018 | Schwammenthal et al. |
| 2018/0303993 A1 | 10/2018 | Schwammenthal et al. |
| 2019/0046702 A1 | 2/2019 | Siess et al. |
| 2019/0175340 A1 | 6/2019 | Tuval |
| 2019/0175806 A1 | 6/2019 | Tuval et al. |
| 2019/0209758 A1 | 7/2019 | Tuval et al. |
| 2019/0239998 A1 | 8/2019 | Tuval et al. |
| 2019/0269840 A1 | 9/2019 | Tuval et al. |
| 2020/0069857 A1 | 3/2020 | Schwammenthal et al. |
| 2020/0254162 A1 | 8/2020 | Schwammenthal et al. |
| 2020/0288988 A1 | 9/2020 | Goldvasser |
| 2021/0236797 A1 | 8/2021 | D'ambrosio et al. |
| 2021/0268261 A1 | 9/2021 | Tuval et al. |
| 2022/0218976 A1 | 7/2022 | Friedland et al. |
| 2023/0233837 A1 | 7/2023 | Schwammenthal et al. |
| 2023/0233841 A1 | 7/2023 | Tuval et al. |
| 2024/0225814 A1 | 7/2024 | Schwammenthal et al. |

FOREIGN PATENT DOCUMENTS

| | | |
|---|---|---|
| CA | 2701809 A1 | 4/2009 |
| CN | 1219136 A | 6/1999 |
| DE | 1033690 B | 7/1958 |
| DE | 10336902 B3 | 8/2004 |
| EP | 1339443 A1 | 9/2003 |
| EP | 1651290 A1 | 5/2006 |
| EP | 1827531 A1 | 9/2007 |
| EP | 1871441 A2 | 1/2008 |
| EP | 2047872 A1 | 4/2009 |
| EP | 2047873 A1 | 4/2009 |
| EP | 2217300 A1 | 8/2010 |
| EP | 2218469 A1 | 8/2010 |
| EP | 2234658 A2 | 10/2010 |
| EP | 2282070 A1 | 2/2011 |
| EP | 2298374 A1 | 3/2011 |
| EP | 2299119 A1 | 3/2011 |
| EP | 2301598 A1 | 3/2011 |
| EP | 2308524 A1 | 4/2011 |
| EP | 2314331 A1 | 4/2011 |
| EP | 2345440 A1 | 7/2011 |
| EP | 2366412 A2 | 9/2011 |
| EP | 2376788 A1 | 10/2011 |
| EP | 2408489 A1 | 1/2012 |
| EP | 2424587 A1 | 3/2012 |
| EP | 2475415 A1 | 7/2012 |
| EP | 2607712 A1 | 6/2013 |
| EP | 2040639 B1 | 2/2014 |
| EP | 2662099 B1 | 9/2014 |
| EP | 2427230 B1 | 12/2014 |
| EP | 2396050 B1 | 1/2015 |
| EP | 2835141 A1 | 2/2015 |
| EP | 2840954 A1 | 3/2015 |
| EP | 2841122 A1 | 3/2015 |
| EP | 2841124 A1 | 3/2015 |
| EP | 2860849 A1 | 4/2015 |
| EP | 2868331 A2 | 5/2015 |
| EP | 2868332 A1 | 5/2015 |
| EP | 2999496 A2 | 3/2016 |
| EP | 3000492 A1 | 3/2016 |
| EP | 3000493 A1 | 3/2016 |
| EP | 3055922 A1 | 8/2016 |
| EP | 3062730 A1 | 9/2016 |
| EP | 3108909 A1 | 12/2016 |
| EP | 3127562 A1 | 2/2017 |
| EP | 3216467 A1 | 9/2017 |
| EP | 3222302 A1 | 9/2017 |
| EP | 3287154 A1 | 2/2018 |
| EP | 3287155 A1 | 2/2018 |
| EP | 3326567 A1 | 5/2018 |
| EP | 3329951 A1 | 6/2018 |
| EP | 3338825 A1 | 6/2018 |
| EP | 3205360 B1 | 8/2018 |
| EP | 3359214 A1 | 8/2018 |
| EP | 3359215 A1 | 8/2018 |
| EP | 3398624 A1 | 11/2018 |
| EP | 3398625 A1 | 11/2018 |
| EP | 3407930 A1 | 12/2018 |
| EP | 3446729 A1 | 2/2019 |
| EP | 3446730 A1 | 2/2019 |
| EP | 3606575 A1 | 2/2020 |
| EP | 3737436 A1 | 11/2020 |
| EP | 3897814 A1 | 10/2021 |
| JP | 2012505038 A | 3/2012 |
| JP | 2016509950 A | 4/2016 |
| WO | 90/13321 | 11/1990 |
| WO | 1994/01148 A1 | 1/1994 |
| WO | 9744071 A1 | 11/1997 |
| WO | 9934847 A2 | 7/1999 |
| WO | 0107787 A1 | 2/2001 |
| WO | 2002/070039 A2 | 3/2001 |
| WO | 0183016 A2 | 11/2001 |
| WO | 2002/038085 | 5/2002 |
| WO | 03/006096 | 1/2003 |
| WO | 03/103745 A2 | 12/2003 |
| WO | 2004073796 A2 | 9/2004 |
| WO | 2005020848 A2 | 3/2005 |
| WO | 2007112033 A2 | 10/2007 |
| WO | 2007127477 A2 | 11/2007 |
| WO | 2008005747 A2 | 1/2008 |
| WO | 2008055301 A1 | 5/2008 |
| WO | 2009010963 A2 | 1/2009 |
| WO | 2009091965 A1 | 7/2009 |
| WO | 2009129481 A1 | 10/2009 |
| WO | 2010133567 A1 | 11/2010 |
| WO | 2010150208 A2 | 12/2010 |
| WO | 2011035926 A1 | 3/2011 |
| WO | 2011047884 A1 | 4/2011 |
| WO | 2011076441 A1 | 6/2011 |
| WO | 2012007141 A1 | 1/2012 |
| WO | 2013032849 A1 | 3/2013 |
| WO | 2013148697 A1 | 10/2013 |
| WO | 2013183060 A2 | 12/2013 |
| WO | 2014141284 A2 | 9/2014 |
| WO | 2015063277 A2 | 5/2015 |
| WO | 2015177793 A2 | 11/2015 |
| WO | 2016185473 A1 | 11/2016 |
| WO | 2017053361 A1 | 3/2017 |
| WO | 2017081561 A1 | 5/2017 |
| WO | 2018033920 A1 | 2/2018 |
| WO | 2018061001 A2 | 4/2018 |
| WO | 2018061002 A1 | 4/2018 |
| WO | 2018078615 A1 | 5/2018 |
| WO | 2018096531 A1 | 5/2018 |
| WO | 2018158636 A1 | 9/2018 |
| WO | 2018172848 A2 | 9/2018 |
| WO | 2018220589 A1 | 12/2018 |
| WO | 2019079342 A1 | 4/2019 |
| WO | 2019125899 A1 | 6/2019 |
| WO | 2019138350 A2 | 7/2019 |
| WO | 2019158996 A1 | 8/2019 |
| WO | 2020234785 A1 | 11/2020 |
| WO | 2021159147 A1 | 8/2021 |

OTHER PUBLICATIONS

Final Office Action for U.S. Appl. No. 18/510,983 mailed Oct. 29, 2024.

Issue Notification for U.S. Appl. No. 17/608,312 mailed Oct. 9, 2024.

Issue Notification for U.S. Appl. No. 18/130,698 mailed Oct. 16, 2024.

Non-Final Office Action for U.S. Appl. No. 18/388,383 mailed Nov. 18, 2024.

Notice of Allowance for U.S. Appl. No. 18/130,698 mailed Aug. 21, 2024.

Notice of Allowance for U.S. Appl. No. 17/608,312 mailed Sep. 3, 2024.

Notice of Allowance for U.S. Appl. No. 18/388,383 mailed Apr. 7, 2025.

Office Action for Australian Application No. 2020277752 mailed Oct. 23, 2024.

(56)          References Cited

OTHER PUBLICATIONS

Office Action for Canadian Application No. 3,192,217 mailed Aug. 26, 2024.
Office Action for Chinese Application No. 202080038424.0 mailed Aug. 27, 2024.
Office Action for Japanese Application No. 2024-002419 mailed Sep. 30, 2024.
U.S. Appl. No. 16/750,354, filed Jan. 23, 2020.
U.S. Appl. No. 17/608,312, filed Nov. 2, 2021.
U.S. Appl. No. 62/851,769, filed May 23, 2019.
U.S. Appl. No. 62/870,822, filed Jul. 5, 2019.
U.S. Appl. No. 62/890,177, filed Aug. 22, 2019.
U.S. Appl. No. 62/983,786, filed Mar. 2, 2020.
U.S. Appl. No. 18/888,529, filed Sep. 18, 2024.
Advisory Action for U.S. Appl. No. 15/888,771 mailed May 4, 2022.
Corrected Notice of Allowance for U.S. Appl. No. 15/312,034 mailed Feb. 12, 2020.
Corrected Notice of Allowance for U.S. Appl. No. 15/423,368 mailed Apr. 17, 2019.
Corrected Notice of Allowance for U.S. Appl. No. 18/130,534 mailed Nov. 24, 2023.
European Search Report for European Application No. 13800935 mailed Jan. 12, 2016.
European Search Report for European Application No. 14762232.8 mailed Sep. 28, 2016.
Examination Report for Indian Application No. 201917018650 mailed Dec. 9, 2021.
Extended European Search Report for European Application No. 19212211.7 mailed Mar. 31, 2020.
Extended European Search Report for European Application No. 19215724.6 mailed Apr. 1, 2020.
Extended European Search Report for European Application No. 19216488.7 mailed Apr. 1, 2020.
Extended European Search Report for European Application No. 19216593.4 mailed Apr. 6, 2020.
Extended European Search Report for European Application No. 20179137.3 mailed Oct. 9, 2020.
Extended European Search Report for European Patent Application No. 23174906.0 mailed Aug. 21, 2023.
Final Office Action for U.S. Appl. No. 14/931,363 mailed Jun. 1, 2017.
Final Office Action for U.S. Appl. No. 15/312,034 mailed Jan. 17, 2019.
Final Office Action for U.S. Appl. No. 15/574,948 mailed Aug. 26, 2020.
Final Office Action for U.S. Appl. No. 15/888,771 mailed Apr. 28, 2020.
Final Office Action for U.S. Appl. No. 15/888,771 mailed Dec. 9, 2021.
Final Office Action for U.S. Appl. No. 16/273,898 mailed Nov. 5, 2020.
Final Office Action for U.S. Appl. No. 16/278,323 mailed May 22, 2020.
Final Office Action for U.S. Appl. No. 16/859,100 mailed Jul. 13, 2022.
International Search Report and Written Opinion from International Application No. PCT/IB2020/054759 mailed Nov. 13, 2020.
International Search Report and Written Opinion from International Application No. PCT/IL2015/050532 mailed Jan. 27, 2016.
International Search Report and Written Opinion from International Application No. PCT/IL2016/050525 mailed Oct. 14, 2016.
International Search Report and Written Opinion from International Application No. PCT/IL2017/051092 mailed Jan. 16, 2018.
International Search Report and Written Opinion from International Application No. PCT/IL2017/051273 mailed Apr. 17, 2018.
International Search Report and Written Opinion from International Application No. PCT/IL2019/050334 mailed Jun. 17, 2019.
International Search Report and Written Opinion from International Application No. PCT/IL2013/050495 mailed Nov. 22, 2013.

International Search Report and Written Opinion from International Application No. PCT/IL2014/050289 mailed Sep. 11, 2014.
Invitation to Pay Additional Fees for International Application No. PCT/IB2020/054759 mailed Jul. 30, 2020.
Invitation to Pay Additional Fees for International Application No. PCT/IL2015/050532 mailed Nov. 17, 2015.
Issue Notification for U.S. Appl. No. 14/931,363 mailed Feb. 21, 2018.
Issue Notification for U.S. Appl. No. 15/312,034 mailed Feb. 19, 2020.
Issue Notification for U.S. Appl. No. 15/423,368 mailed May 8, 2019.
Issue Notification for U.S. Appl. No. 15/574,948 mailed Mar. 16, 2022.
Issue Notification for U.S. Appl. No. 15/888,771 mailed Oct. 12, 2022.
Issue Notification for U.S. Appl. No. 16/022,445 mailed Jul. 10, 2019.
Issue Notification for U.S. Appl. No. 16/035,871 mailed Dec. 29, 2020.
Issue Notification for U.S. Appl. No. 16/273,898 mailed Oct. 13, 2021.
Issue Notification for U.S. Appl. No. 16/278,323 mailed Nov. 24, 2020.
Issue Notification for U.S. Appl. No. 16/281,385 mailed Jun. 16, 2021.
Issue Notification for U.S. Appl. No. 16/335,786 mailed Jun. 2, 2021.
Issue Notification for U.S. Appl. No. 16/345,389 mailed May 26, 2021.
Issue Notification for U.S. Appl. No. 16/677,893 mailed Jan. 10, 2024.
Issue Notification for U.S. Appl. No. 16/682,016 mailed Mar. 23, 2022.
Issue Notification for U.S. Appl. No. 16/682,269 mailed Mar. 23, 2022.
Issue Notification for U.S. Appl. No. 16/859,100 mailed Apr. 26, 2023.
Issue Notification for U.S. Appl. No. 16/859,492 mailed Apr. 26, 2023.
Issue Notification for U.S. Appl. No. 17/320,742 mailed Apr. 26, 2023.
Issue Notification for U.S. Appl. No. 17/487,145 mailed Nov. 22, 2023.
Issue Notification for U.S. Appl. No. 18/130,534 mailed Dec. 6, 2023.
Non-Final Office Action for U.S. Appl. No. 14/405,144 mailed Feb. 22, 2016.
Non-Final Office Action for U.S. Appl. No. 14/405,144 mailed Jul. 14, 2016.
Non-Final Office Action for U.S. Appl. No. 14/567,439 mailed Nov. 16, 2016.
Non-Final Office Action for U.S. Appl. No. 14/774,081 mailed May 24, 2017.
Non-Final Office Action for U.S. Appl. No. 14/774,081 mailed Oct. 12, 2017.
Non-Final Office Action for U.S. Appl. No. 14/931,363 mailed Feb. 15, 2017.
Non-Final Office Action for U.S. Appl. No. 14/931,363 mailed Oct. 3, 2016.
Non-Final Office Action for U.S. Appl. No. 15/423,368 mailed Jun. 6, 2018.
Non-Final Office Action for U.S. Appl. No. 15/574,948 mailed Jan. 13, 2020.
Non-Final Office Action for U.S. Appl. No. 15/888,771 mailed Jun. 1, 2021.
Non-Final Office Action for U.S. Appl. No. 15/888,771 mailed May 25, 2022.
Non-Final Office Action for U.S. Appl. No. 15/888,771 mailed Oct. 4, 2019.
Non-Final Office Action for U.S. Appl. No. 16/022,445 mailed Aug. 9, 2018.

(56)        References Cited

OTHER PUBLICATIONS

Non-Final Office Action for U.S. Appl. No. 16/035,871 mailed Jan. 22, 2020.

Non-Final Office Action for U.S. Appl. No. 16/242,797 mailed Nov. 16, 2021.

Non-Final Office Action for U.S. Appl. No. 16/273,898 mailed Feb. 17, 2021.

Non-Final Office Action for U.S. Appl. No. 16/273,898 mailed Jun. 18, 2020.

Non-Final Office Action for U.S. Appl. No. 16/278,323 mailed May 22, 2020.

Non-Final Office Action for U.S. Appl. No. 16/281,385 mailed Oct. 14, 2020.

Non-Final Office Action for U.S. Appl. No. 16/335,786 mailed Sep. 17, 2020.

Non-Final Office Action for U.S. Appl. No. 16/345,389 mailed Oct. 26, 2020.

Non-Final Office Action for U.S. Appl. No. 16/677,893 mailed Dec. 28, 2022.

Non-Final Office Action for U.S. Appl. No. 16/677,893 mailed Jan. 11, 2022.

Non-Final Office Action for U.S. Appl. No. 16/677,893 mailed Jul. 1, 2022.

Non-Final Office Action for U.S. Appl. No. 16/677,893 mailed May 9, 2023.

Non-Final Office Action for U.S. Appl. No. 16/682,016 mailed Sep. 20, 2021.

Non-Final Office Action for U.S. Appl. No. 16/682,269 mailed Sep. 20, 2021.

Non-Final Office Action for U.S. Appl. No. 16/859,100 mailed Apr. 29, 2022.

Non-Final Office Action for U.S. Appl. No. 16/859,492 mailed Oct. 14, 2022.

Non-Final Office Action for U.S. Appl. No. 17/320,742 mailed Dec. 7, 2022.

Non-Final Office Action for U.S. Appl. No. 17/487,145 mailed Mar. 1, 2023.

Non-Final Office Action for U.S. Appl. No. 18/130,205 mailed Dec. 20, 2023.

Non-Final Office Action for U.S. Appl. No. 18/130,698 mailed Dec. 15, 2023.

Non-Final Office Action for U.S. Appl. No. 18/510,983 mailed Jun. 5, 2024.

Notice of Acceptance for Australian Application No. 2017364359 mailed Nov. 17, 2022.

Notice of Allowance for U.S. Appl. No. 14/567,439 mailed Jun. 2, 2017.

Notice of Allowance for U.S. Appl. No. 14/774,081 mailed Apr. 11, 2018.

Notice of Allowance for U.S. Appl. No. 14/931,363 mailed Dec. 12, 2017.

Notice of Allowance for U.S. Appl. No. 14/931,363 mailed Oct. 12, 2017.

Notice of Allowance for U.S. Appl. No. 15/312,034 mailed Jan. 15, 2020.

Notice of Allowance for U.S. Appl. No. 15/312,034 mailed Jun. 27, 2019.

Notice of Allowance for U.S. Appl. No. 15/423,368 mailed Apr. 4, 2019.

Notice of Allowance for U.S. Appl. No. 15/423,368 mailed Nov. 13, 2018.

Notice of Allowance for U.S. Appl. No. 15/574,948 mailed Jan. 27, 2022.

Notice of Allowance for U.S. Appl. No. 15/574,948 mailed Nov. 18, 2021.

Notice of Allowance for U.S. Appl. No. 15/888,771 mailed Jun. 28, 2022.

Notice of Allowance for U.S. Appl. No. 16/022,445 mailed Mar. 18, 2019.

Notice of Allowance for U.S. Appl. No. 16/035,871 mailed Aug. 28, 2020.

Notice of Allowance for U.S. Appl. No. 16/035,871 mailed Dec. 4, 2020.

Notice of Allowance for U.S. Appl. No. 16/273,898 mailed Jun. 30, 2021.

Notice of Allowance for U.S. Appl. No. 16/278,323 mailed Oct. 29, 2020.

Notice of Allowance for U.S. Appl. No. 16/281,385 mailed Mar. 8, 2021.

Notice of Allowance for U.S. Appl. No. 16/335,786 mailed Feb. 22, 2021.

Notice of Allowance for U.S. Appl. No. 16/345,389 mailed Feb. 16, 2021.

Notice of Allowance for U.S. Appl. No. 16/677,893 mailed Oct. 19, 2023.

Notice of Allowance for U.S. Appl. No. 16/682,016 mailed Feb. 23, 2022.

Notice of Allowance for U.S. Appl. No. 16/682,269 mailed Feb. 23, 2022.

Notice of Allowance for U.S. Appl. No. 16/859,100 mailed Mar. 7, 2023.

Notice of Allowance for U.S. Appl. No. 16/859,492 mailed Mar. 15, 2023.

Notice of Allowance for U.S. Appl. No. 17/320,742 mailed Mar. 22, 2023.

Notice of Allowance for U.S. Appl. No. 17/487,145 mailed Aug. 15, 2023.

Notice of Allowance for U.S. Appl. No. 17/608,312 mailed Jun. 21, 2024.

Notice of Allowance for U.S. Appl. No. 18/130,534 mailed Oct. 30, 2023.

Notice of Allowance for U.S. Appl. No. 18/130,698 mailed Apr. 11, 2024.

Office Action for Australian Application No. 2015262870 mailed Apr. 29, 2019.

Office Action for Australian Application No. 2019202647 mailed Jun. 26, 2019.

Office Action for Australian Application No. 2020201055 mailed Sep. 15, 2020.

Office Action for Australian Application No. 2021225141 mailed Oct. 10, 2022.

Office Action for Canadian Application No. 2,948,121 mailed Dec. 15, 2021.

Office Action for Canadian Application No. 2,948,121 mailed Jul. 8, 2021.

Office Action for Canadian Application No. 3,039,302 mailed Mar. 21, 2023.

Office Action for Canadian Application No. 3,080,800 mailed Mar. 21, 2023.

Office Action for Canadian Application No. 3,126,978 mailed May 1, 2023.

Office Action for Canadian Application No. 3,126,978 mailed Nov. 1, 2022.

Office Action for Canadian Application No. 3,137,274 mailed Jan. 15, 2024.

Office Action for Canadian Application No. 3,137,274 mailed Mar. 29, 2023.

Office Action for Chinese Application No. 201380037335.4 mailed Mar. 22, 2017.

Office Action for Chinese Application No. 201380037335.4 mailed Oct. 17, 2016.

Office Action for Chinese Application No. 201380037335.4 mailed Sep. 20, 2017.

Office Action for Chinese Application No. 201780072633.5 mailed May 26, 2021.

Office Action for Chinese Application No. 201810418034.0 mailed Aug. 4, 2020.

Office Action for Chinese Application No. 201810418034.0 mailed Dec. 24, 2020.

Office Action for Chinese Application No. 201810418034.0 mailed Nov. 1, 2019.

(56) References Cited

OTHER PUBLICATIONS

Office Action for Chinese Application No. 201811196500.1 mailed Aug. 28, 2020.
Office Action for Chinese Application No. 201910109564.1 mailed Feb. 1, 2021.
Office Action for Chinese Application No. 202080038424.0 mailed Dec. 18, 2023.
Office Action for Chinese Application No. 202110905794.6 mailed Feb. 1, 2024.
Office Action for European Application No. 13800935 mailed Sep. 30, 2016.
Office Action for European Application No. 15753493.4 mailed Jul. 17, 2019.
Office Action for European Application No. 19216488.7 mailed Oct. 19, 2021.
Office Action for European Application No. 20179137.3 mailed Jan. 5, 2023.
Office Action for European Application No. 20179137.3 mailed Nov. 9, 2021.
Office Action for Indian Application No. 201917018650 mailed Dec. 9, 2021.
Office Action for Japanese Application No. 2015-562562 mailed Jan. 29, 2019.
Office Action for Japanese Application No. 2015-562562 mailed Jun. 13, 2018.
Office Action for Japanese Application No. 2015-562562 mailed Oct. 27, 2017.
Office Action for Japanese Application No. 2016-568548 mailed Mar. 18, 2019.
Office Action for Japanese Application No. 2019-520097 mailed Oct. 26, 2021.
Office Action for Japanese Application No. 2020-009045 mailed Feb. 1, 2021.
Office Action for Japanese Application No. 2020-93277 mailed Jun. 23, 2021.
Office Action for Japanese Application No. 2021-563728 mailed Feb. 27, 2024.
Office Action for Japanese Application No. 2022-31553 mailed Dec. 23, 2022.
Restriction Requirement for U.S. Appl. No. 14/567,439 mailed Aug. 23, 2016.
Restriction Requirement for U.S. Appl. No. 14/774,081 mailed Mar. 9, 2017.
Restriction Requirement for U.S. Appl. No. 14/931,363 mailed Jul. 22, 2016.
Restriction Requirement for U.S. Appl. No. 15/888,771 mailed Apr. 15, 2019.
Restriction Requirement for U.S. Appl. No. 16/035,871 mailed Sep. 27, 2019.
Restriction Requirement for U.S. Appl. No. 16/677,893 mailed Sep. 22, 2021.
Restriction Requirement for U.S. Appl. No. 16/859,492 mailed Jul. 28, 2022.
Supplemental Notice of Allowance for U.S. Appl. No. 17/487,145 mailed Nov. 3, 2023.
U.S. Appl. No. 14/405,144, filed Dec. 2, 2014.
U.S. Appl. No. 14/567,439, filed Dec. 11, 2014.
U.S. Appl. No. 14/774,081, filed Sep. 9, 2015.
U.S. Appl. No. 15/312,034, filed Nov. 17, 2016.
U.S. Appl. No. 15/423,368, filed Feb. 2, 2017.
U.S. Appl. No. 15/574,948, filed Nov. 17, 2017.
U.S. Appl. No. 15/888,771, filed Feb. 5, 2018.
U.S. Appl. No. 16/022,445, filed Jun. 28, 2018.
U.S. Appl. No. 16/273,898, filed Feb. 12, 2019.
U.S. Appl. No. 16/275,559, filed Feb. 14, 2019.
U.S. Appl. No. 16/276,965, filed Feb. 15, 2019.
U.S. Appl. No. 16/277,411, filed Feb. 15, 2019.
U.S. Appl. No. 16/278,323, filed Feb. 18, 2019.
U.S. Appl. No. 16/281,264, filed Feb. 21, 2019.
U.S. Appl. No. 16/281,385, filed Feb. 21, 2019.

U.S. Appl. No. 16/345,389, filed Apr. 26, 2019.
U.S. Appl. No. 16/677,893, filed Nov. 8, 2019.
U.S. Appl. No. 16/682,016, filed Nov. 13, 2019.
U.S. Appl. No. 16/859,100, filed Apr. 27, 2020.
U.S. Appl. No. 16/859,492, filed Apr. 27, 2020.
U.S. Appl. No. 17/320,742, filed May 14, 2021.
U.S. Appl. No. 17/487,145, filed Sep. 28, 2021.
U.S. Appl. No. 18/130,205, filed Apr. 4, 2023.
U.S. Appl. No. 18/130,534, filed Apr. 4, 2023.
U.S. Appl. No. 18/130,698, filed Apr. 4, 2023.
U.S. Appl. No. 18/388,383, filed Nov. 9, 2023.
U.S. Appl. No. 18/422,309, filed Jan. 25, 2024.
U.S. Appl. No. 18/510,983, filed Nov. 16, 2023.
U.S. Appl. No. 61/656,244, filed Jun. 6, 2012.
U.S. Appl. No. 61/779,803, filed Mar. 13, 2013.
U.S. Appl. No. 61/914,470, filed Dec. 11, 2013.
U.S. Appl. No. 61/914,475, filed Dec. 11, 2013.
U.S. Appl. No. 62/000,192, filed May 19, 2014.
U.S. Appl. No. 62/162,881, filed May 18, 2015.
U.S. Appl. No. 62/401,403, filed Sep. 29, 2016.
U.S. Appl. No. 62/412,631, filed Oct. 25, 2016.
U.S. Appl. No. 62/425,814, filed Nov. 23, 2016.
U.S. Appl. No. 62/543,540, filed Aug. 10, 2017.
U.S. Appl. No. 62/615,538, filed Jan. 10, 2018.
U.S. Appl. No. 62/665,715, filed May 2, 2018.
U.S. Appl. No. 62/681,868, filed Jun. 7, 2018.
U.S. Appl. No. 62/727,605, filed Sep. 6, 2018.
"Compendium of Technical and Scientific Information for the Hemopump Temporary Cardiac Assist System", Johnson & Johnson Interventional Systems, 1988, pp. 1-15.
Achour, et al., "Mechanical Left Ventricular Unloading Prior to Reperfusion Reduces Infarct Size in a Canine Infarction Model", Catheterization and Cardiovascular Interventions 64, 2005, pp. 182-192.
Agarwal, et al., "Newer-generation ventricular assist devices", Best Practice & Research Clinical Anaesthesiology, 2012, pp. 117-130.
Alba, et al., "The future is here: ventricular assist devices for the failing heart", Expert review of cardiovascular therapy, 2009, pp. 1067-1077.
Burnett, et al., "Renal Interstitial Pressure And Sodium Excretion During Renal Vein Constriction", American Physiological Society, 1980, pp. F279-F282.
Butler, et al., "The Hemopump—A New Cardiac Prothesis Device", Reprinted from IEEE Transactions on Biomedical Engineering, vol. 37, No. 2, Feb. 1990, pp. 192-195.
Chan, et al., "Rapid manufacturing techniques in the development of an axial blood pump impeller", Proc. Instn Mech. Engrs vol. 217 Part H: J. Engineering in Medicine, 2003, pp. 469-475.
Coxworth, "Artificial Vein Valve Could Replace Drugs For Treating Common Circulatory Problem", Published on Gizmag website (http://www.gizmag.com/artificial-venous-valve-cvi/21785/), Mar. 9, 2012.
Coxworth, "Artificial vein valve could replace drugs for treating common circulatory problem", Published on Gizmag website (http://www.gizmag.com/artificial-venous-valve-cvi/21785/), Mar. 9, 2012, pp. 2.
Damman, et al., "Decreased Cardiac Output, Venous Congestion And The Association With Renal Impairment In Patients With Cardiac Dysfunction", European Journal of Heart Failure, 2007, pp. 872-878.
Damman, et al., "Increased Central Venous Pressure Is Associated With Impaired Renal Function And Mortality In A Broad Spectrum Of Patients With Cardiovascular Disease", Journal of American College of Cardiology, 2009, pp. 582-588.
Dekker, et al., "Efficacy of a New Intraaortic Propeller Pump vs the Intraaortic Balloon Pump", Chest, vol. 123, Issue 6, Jun. 2003, pp. 2089-2095.
Doty, et al., "Effect of increased renal venous pressure on renal function", The Journal of Trauma: Injury, Infection, and Critical Care, Issue, Dec. 1999, p. 1000.
Doty, et al., "The Effect Of Increased Renal Venous Pressure On Renal Function", The Journal of Trauma,, Dec. 1999, pp. 1000-1003.

(56) References Cited

OTHER PUBLICATIONS

Felker, et al., "Anemia As A Risk Factor And Therapeutic Target In Heart Failure", Journal of the American College of Cardiology, 2004, pp. 959-966.

Firth, et al., "Raised Venous Pressure: A Direct Cause Of Sodium Retention In Oedema?", The Lancet, May 7, 1988, pp. 1033-1036.

Firth, et al., "Raised venous pressure: a direct cause of sodium retention in oedema?", Lancet, 1988, pp. 1033-1035.

Flameng, "Temporary Cardiac Assist with an Axial Pump System", Steinkopff Verlag Darmstadt, 1991, 79 pages.

Forman, et al., "Incidence, Predictors At Admission, And Impact Of Worsening Renal Function Among Patients Hospitalized With Heart Failure", Journal of American College of Cardiology, 2004, pp. 61-67.

Fraser, et al., "The use of computational fluid dynamics in the development of ventricular assist devices", Medical engineering & physics, 2011, pp. 263-280.

Frazier, et al., "First Human Use of the Hemopump, a Catheter-Mounted Ventricular Assist Device", Annual of Thoracic Surgeons, vol. 49, 1990, pp. 299-304.

Frazier, et al., "Treatment of Cardiac Allograft Failure by use of an IntraAortic Axial Flow Pump", Journal of Heart Transplantation, St. Louis, vol. 9, No. 4, pp. 408-414, Jul. 1990.

Gomes, et al., "Heterologous valve implantation in the infra-renal vena cava for treatment of the iliac venous valve regurgitation disease", experimental study; Rev Bras Cir Cardiovasc, 2002, pp. 367-369.

Gunther, et al., "Experimentelle Radiologie", Life Sciences, Berichte Aus Der Rheinischwestfälischen Technischen Hochschule Aachen Ausgabe Feb. 2002.

Haddy, et al., "Effect Of Elevation Of Intraluminal Pressure On Renal Vascular Resistance", Circulation Research Journal Of The American Heart Association, 1956, pp. 659-663.

Heywood, et al., "High prevalence of renal dysfunction and its impact on outcome in 118,465 patients hospitalized with acute decompensated heart failure", a report from the ADHERE database. J Cardiac Fail, 2007, pp. 422-430.

Heywood, et al., "High Prevalence Of Renal Dysfunction And Its Impact On Outcome In 118,465 Patients Hospitalized With Acute Decompensated Heart Failure: A Report From The ADHERE Database", Journal of Cardiac Failure, 2007, pp. 422-430.

Hillege, et al., "Renal Function As A Predictor Of Outcome In A Broad Spectrum Of Patients With Heart Failure", Circulation Journal of the American Heart Association, 2006, pp. 671-678.

Hillege, et al., "Renal Function, Neurohormonal Activation, And Survival In Patients With Chronic Heart Failure", Circulation Journal of the American Heart Association, 2000, pp. 203-210.

Hsu, et al., "Review of recent patents on foldable ventricular assist devices", Recent Patents on Biomedical Engineering, 2012, pp. 208-222.

Ikari, "The Physics Of Guiding Catheter; The IKARI Guiding Catheter In TRI", available at httu:i /www.docstoc.com/docs/148136553/The-[KARI-catheter---anovel-guide-for-TRI--.

Kafagy, et al., "Design of axial blood pumps for patients with dysfunctional fontan physiology: computational studies and performance testing", Artificial organs, 2015, pp. 34-42.

Kang, et al., "Fluid dynamics aspects of miniaturized axial-flow blood pump", Bio-medical materials and engineering, 2014, pp. 723-729.

Koochaki, et al., "A new design and computational fluid dynamics study of an implantable axial blood pump", Australasian Physical & Engineering Sciences in Medicine, 2013, pp. 417-422.

Lauten, et al., "Heterotopic Transcatheter Tricuspid Valve Implantation: First-In-Man Application Of A Novel Approach To Tricuspid Regurgitation", European Heart Journal, Feb. 15, 2011, pp. 1207-1213.

Ledoux, et al., "Left Ventricular Unloading With Intra-aortic Counter Pulsation Prior to Reperfusion Reduces Myocardial Release of Endothelin-1 and Decreases Infarction Size in a Porcine Ischemia-Reperfusion Model", Catheterization and Cardiovascular Interventions 72, 2008, pp. 513-521.

McAlister, et al., "Renal Insufficiency And Heart Failure: Prognostic And Therapeutic Implications From A Prospective Cohort Study", Circulation Journal of the American Heart Association, 2004, pp. 1004-1009.

Merhige, et al., "Effect of the Hemopump Left Ventricular Assist Device on Regional Myocardial Perfusion and Function", Reduction of Ischemia during Coronary Occlusion, Johnson & Johnson Interventional Systems Supplement 3, Circulation vol. 80, No. 5, Nov. 1989, pp. III-159-III-166.

Mullens, et al., "Elevated Intra-Abdominal Pressure In Acute Decompensated Heart Failure. A Potential Contributor To Worsening Renal Function", Journal of the American College of Cardiology, 2008, pp. 300-306.

Mullens, et al., "Importance Of Venous Congestion For Worsening Of Renal Function In Advanced Decompensated Heart Failure", Journal of American College of Cardiology, 2009, pp. 589-596.

Mullens, et al., "Prompt Reduction In Intra-Abdominal Pressure Following Large-Volume Mechanical Fluid Removal Improves Renal Insufficiency In Refractory Decompensated Heart Failure", Journal of Cardiac Failure, 2008, pp. 508-514.

Notarius, et al., "Central Venous Pressure During Exercise: Role Of Muscle Pump", Canadian Journal of Physiology and Pharmacology, 1996, pp. 647-651.

Park, et al., "Nutcracker Syndrome: Intravascular Stenting Approach", Nephrol Dial Transplant, 2000, pp. 99-101.

Reul, et al., "Blood pumps for circulatory support", Perfusion-Sevenoaks, 2000, pp. 295-312.

Roundtree, et al., "The Hemopump Cardiac Assist System: Nursing Care of the Patient", Reprinted from Critical Care Nurse, Apr. 1991.

Schmitz-Rode, et al., "An Expandable Percutaneous Catheter Pump For Left Ventricular Support", Journal of the American College of Cardiology, vol. 45, No. 11, 2005, pp. 1856-1861.

Scholz, et al., "Mechanical left Ventricular Unloading During High Risk Coronary Angioplasty: First Use of a New Percutaneous Transvalvular Left Ventricular Assist Device", Catheterization and Cardiovascular Diagnosis 31, 1994, pp. 61-69.

Semple, et al., "Effect Of Increased Renal Venous Pressure On Circulatory "Autoregulation" Of Isolated Dog Kidneys", Circulation Research Journal of The American Heart Association, 1959, pp. 643-648.

Siess, "System Analysis and Development of Intravascular Rotation Pumps for Cardiac Assist", Helmholtz-Institute—Chapter 3, Jun. 1998, 17 pages.

Smalling, et al., "Improved Regional Myocardial Blood Flow, Left Ventricular Unloading, and Infarct Salvage Using an Axial-Flow, Transvalvular Left Ventricular Assist Device", A Comparison With Intra-Aortic Balloon Counterpulsation and Reperfusion Alone in a Canine Infarction Model, Presented in part at the American College of Cardiology 38th Annual Scientific Session, Mar. 1990, pp. 1152-1160.

Smalling, et al., "The Hemopump: A transvalvular, axial flow, left ventricular assist device", Coronary Artery Disease, Circulatory support devices in clinical cardiology, vol. 2 No. 6, pp. 666-671, Aug. 1991.

Smalling, et al., "Transvalvular Left Ventricular Assistance in Cardiogenic Shock Secondary to Acute Myocardial Infarction", Evidence for Recovery From Near Fatal Myocardial Stunning, JACC vol. 23, No. 3, pp. 637-644, Mar. 1, 1994.

Song, et al., "Axial flow blood pumps", ASAIO journal, 2003, pp. 355-364.

Tamareille, et al., "Left ventricular unloading before reperfusion reduces endothelin-1 release and calcium overload in porcine myocardial infarction", Cardiopulmonary Support and Physiology, The Journal of Thoracic and Cardiovascular Surgery, vol. 136, No. 2, 2008, pp. 343-351.

Tang, et al., "Anemia In Chronic Heart Failure: Prevalence, Etiology, Clinical Correlates, And Treatment Options", Circulation Journal of the American Heart Association, 2006, pp. 2454-2461.

(56) References Cited

OTHER PUBLICATIONS

Throckmorton, et al., "Design of a protective cage for an intra vascular axial flow blood pump to mechanically assist the failing Fontan", Artificial organs, 2009, pp. 611-621.

Thunberg, et al., "Ventricular assist devices today and tomorrow", Journal of cardiothoracic and vascular anesthesia, 2010, pp. 656-680.

Timms, "A review of clinical ventricular assist devices", Medical engineering & physics, 2011, pp. 1041-1047.

Uthoff, et al., "Central venous pressure at emergency room presentation predicts cardiac rehospitalization in patients with decompensated heart failure", European Journal of Heart Failure, 2010, pp. 469-476.

Uthoff, et al., "Central Venous Pressure At Emergency Room Presentation Predicts Cardiac Rehospitalization In Patients With Decompensated Heart Failure", European Journal of Heart Failure, Mar. 11, 2010, 8 Pages.

Wampler, "Newspaper Articles", Captain Hemo, 1988, 6 pages.

Wampler, "Newsweek", Captain Hemo, May 16, 1988, 3 pages.

Wampler, "THI Today", Captain Hemo, Summer 1988, 2 pages.

Wampler, "Time Magazine", Captain Hemo, May 1988, 2 pages.

Wampler, et al., "Treatment of Cardiogenic Shock With the Hemopump Left Ventricular Assist Device", Annual of Thoracic Surgery, vol. 52, pp. 560-513, 1991.

Wampler, "U.S. News & World Report", Captain Hemo, pp. 1-2, May 16, 1988.

Wencker, "Acute Cardio-Renal Syndrome: Progression From Congestive Heart Failure To Congestive Kidney Failure", Current Heart Failure Reports, 2007, pp. 134-138.

Winton, "The Control Of Glomerular Pressure By Vascular Changes Within The Mammalian Kidney, Demonstrated By The Actions Of Adrenaline", Journal of Physiology, Nov. 1931, pp. 151-162.

Winton, "The Influence Of Venous Pressure On The Isolated Mammalian Kidney", Journal of Physiology, Jun. 6, 1931, pp. 49-61.

Wood, "The Mechanism Of The Increased Venous Pressure With Exercise In Congestive Heart Failure", Journal of Clinical Investigation, 1962, pp. 2020-2024.

Wu, et al., "Design and simulation of axial flow maglev blood pump", International Journal of Information Engineering and Electronic Business, 2011, p. 42.

Yancy, et al., "Clinical Presentation, Management, And In-Hospital Outcomes Of Patients Admitted With Acute Decompensated Heart Failure With Preserved Systolic Function. A Report From The Acute Decompensated Heart Failure National Registry (ADHERE) Database", Journal of the American College of Cardiology, 2006, pp. 76-84.

Examination Report for European Application No. 19716995.6 mailed Mar. 1, 2024.

Final Office Action for U.S. Appl. No. 18/130,205 mailed Jul. 16, 2024.

Office Action for Japanese Application No. 2021-563728 mailed Jul. 10, 2024.

Examination Report for European Application No. 23174906.0 mailed Oct. 9, 2025.

Issue Notification for U.S. Appl. No. 18/388,383 mailed Sep. 3, 2025.

Notice of Allowance for U.S. Appl. No. 18/510,983 mailed Aug. 1, 2025.

* cited by examiner

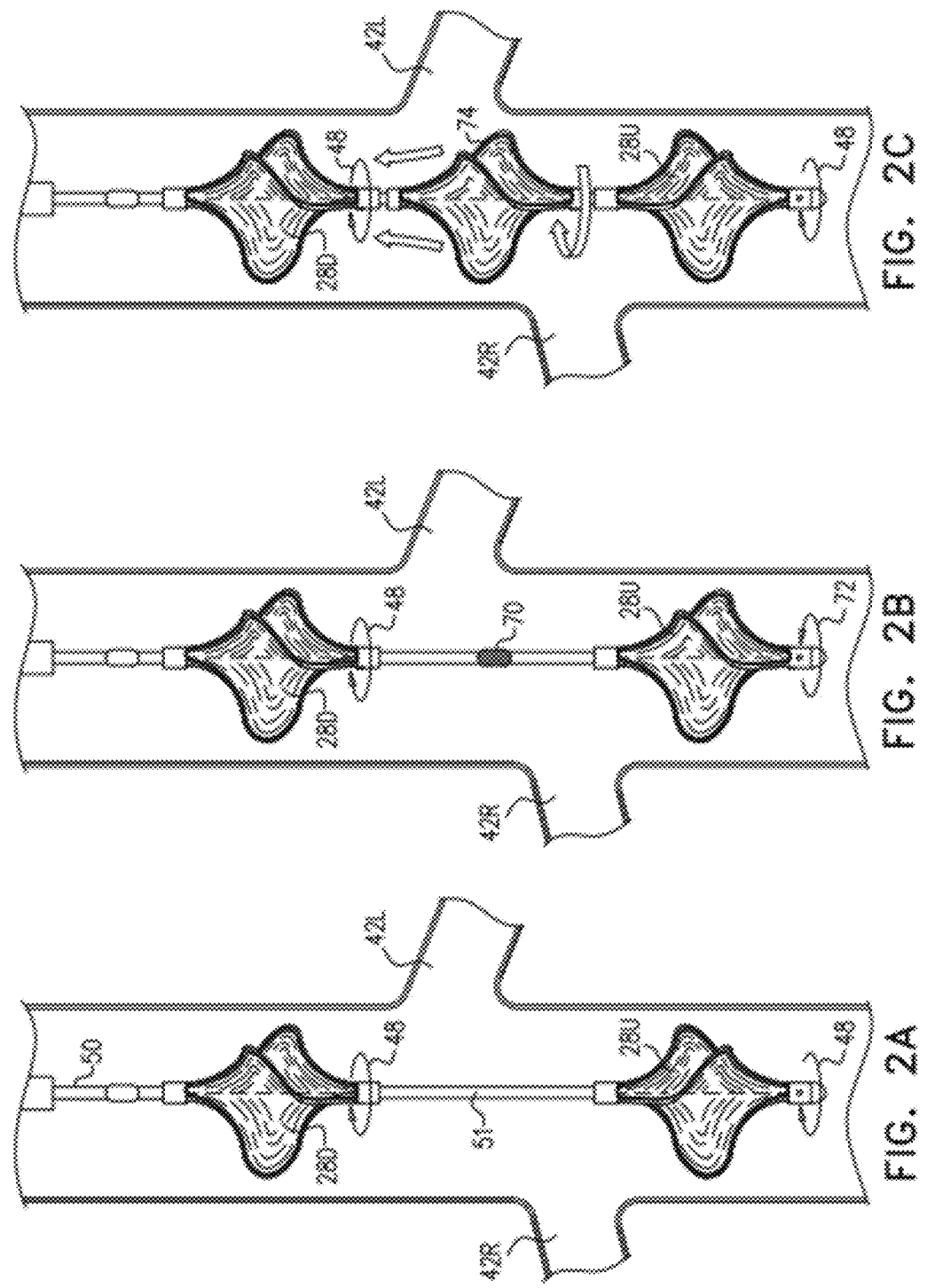

VENA CAVAL OCCLUSION

CROSS-REFERENCES TO RELATED APPLICATIONS

The present application is a continuation of U.S. application Ser. No. 18/130,698 to Tuval (published as US 2023/0233841), filed Apr. 4, 2023, which is a continuation of U.S. application Ser. No. 17/320,742 to Tuval (issued as U.S. Pat. No. 11,648,392), filed May 14, 2021, which is a continuation of U.S. application Ser. No. 16/345,389 to Tuval (issued as U.S. Pat. No. 11,033,727), which is the US national phase application of PCT Application No. PCT/IL/2017/051273 to Tuval (published as WO 18/096531), filed Nov. 21, 2017, which claims priority from U.S. Provisional Patent App. No. 62/425,814 to Tuval, filed Nov. 23, 2016, entitled "Blood pumps," which is incorporated herein by reference.

FIELD OF EMBODIMENTS OF THE INVENTION

Some applications of the present invention generally relate to medical apparatus. Specifically, some applications of the present invention relate to apparatus and methods associated with placing a pump in one or more of a subject's renal veins, and/or in the subject's vena cava.

BACKGROUND

It is common for cardiac dysfunction or congestive heart failure to develop into kidney dysfunction, which, in turn, causes congestive heart failure symptoms to develop or worsen. Typically, systolic and/or diastolic cardiac dysfunction causes systemic venous congestion, which gives rise to an increase in renal venous and interstitial pressure. The increase in the pressure causes fluid retention by the body to increase due both to kidney dysfunction and renal neuro-hormonal activation, both of which typically develop as a result of the increase in renal venous and interstitial pressure. The resulting fluid retention causes congestive heart failure to develop or worsen, by causing a blood volume overload at the heart and/or by increasing systemic resistance. Similarly, it is common for kidney dysfunction and/or renal neurohormonal activation to develop into cardiac dysfunction and/or congestive heart failure. This patho-physiological cycle, in which cardiac dysfunction and/or congestive heart failure leads to kidney dysfunction and/or renal neurohormonal activation, or in which kidney dysfunction and/or renal neurohormonal activation leads to cardiac dysfunction and/or congestive heart failure, each dysfunction leading to deterioration in the other dysfunction, is called the cardio-renal syndrome.

Increased renal venous pressure has been experimentally shown to cause azotemia, and a reduction in glomerular filtration rate, renal blood flow, urine output, and sodium excretion. It has also been shown to increase plasma renin and aldosterone, and protein excretion. Venous congestion may also contribute to anemia via three different pathways: A reduction in the kidney's erythropoietin production, hemodilution by fluid retention, and an inflammatory response leading to a reduced gastro-intestinal iron uptake.

Mechanistically, increased renal venous pressure may cause intracapsular pressure and, subsequently, interstitial peritubular pressure, to rise. A rise in peritubular pressure may impact tubular function (reduce sodium excretion), as well as diminish glomerular filtration, by raising the pressure in the Bowman capsule.

In heart failure patients, increased renal venous pressure may not only result from increased central venous (right atrial) pressure, but also from intraperitoneal fluid accumulations (ascites) exerting direct pressure on the renal veins. Reduction of intraabdominal pressure in heart failure patients by removal of fluid (e.g., via paracentesis, and/or ultrafiltration), has been shown to reduce plasma creatinine levels.

Increased venous return resulting from activation of the "leg muscle pump" during physical activity such as walking may raise systemic venous pressure, particularly in heart failure patients, and may result in reflux into the renal veins.

Typically, in patients suffering from acute heart failure, elevated systemic venous pressures cause increased renal parenchymal pressure and increased intraabdominal pressure, factors that can contribute to deterioration of renal perfusion and function. In addition, high systemic venous pressures may impede lymphatic drainage of pulmonary interstitial fluid resulting in aggravation and prolongation of pulmonary congestion in patients with acute pulmonary edema.

SUMMARY OF EMBODIMENTS

In accordance with some applications of the present invention, a blood pump is placed inside a blood vessel of a subject, the blood pump including (a) an impeller configured to pump blood by rotating, and (b) a support cage that is shaped to define (i) a narrow portion that is configured to be disposed around the impeller, and to maintain a separation between a wall of the blood vessel and the impeller, and (ii) a radial extension from the narrow portion of the support cage that extends radially outward with respect to the narrow portion of the support cage, the extension being configured to substantially maintain a longitudinal axis of the impeller in alignment with a local longitudinal axis of the blood vessel by contacting the wall of the blood vessel. For some applications, the narrow portion and the radial extension of the support cage are two separately-formed components. Alternatively, the narrow portion and the radial extension of the support cage are separate portions of a single integrated component. In accordance with respective applications, the radial extension includes radially-protruding support arms, a bulbous extension that constitutes a radial extension from the narrow portion of the cage, and/or a frustoconical support cage that constitutes a radial extension from the narrow portion of the cage.

Typically, such applications are used with an impeller that is undersized with respect to the vessel in which it is placed. Such an impeller may be used, for example, in cases in which a larger impeller would undergo a substantial amount of vibration while rotating. Alternatively or additionally, such an impeller may be used in cases in which, if the portion of the cage that is configured to separate between the impeller and the vessel wall was larger, there would be a risk that the portion of the cage would become radially compressed by the walls of the vessel, which may result in the impeller becoming deformed (e.g., by the upstream and downstream ends of the impeller axis becoming misaligned), and/or in the impeller becoming misaligned with the local longitudinal axis of the vessel. Typically, for such applications, a narrow portion of the cage surrounds the impeller and is configured to maintain a separation between a wall of the blood vessel and the impeller, for example, in case the vessel narrows, such that, in the absence of the narrow portion of the cage, the walls of the vessel would collapse onto the impeller. The radial extension is typically configured to anchor the blood pump within the vessel by exerting an outward radial force upon the vessel wall, and to substantially maintain a longitudinal axis of the impeller in alignment with a local longitudinal axis of the blood vessel by contacting the wall of the blood vessel. Typically, a stiffness of the narrow portion of the cage is greater than that of the radial extension, such that the narrow portion of the cage is configured to maintain the separation between the wall of the blood vessel and the impeller, even if the wall of the vessel exerts pressure upon the support cage that causes the radial extension to deform.

For some applications, material (e.g., blood-impermeable material) is disposed on the support cage. Typically, the material is coupled to the support cage such as to contact the vessel wall and to occlude the blood vessel in the region of the blood vessel that surrounds the impeller. The material typically defines a hole therethrough in a central region of the vessel, in a vicinity of the impeller. The material is configured to occlude backflow of blood around the outside of the impeller, but such as to allow antegrade blood flow in the central region of the vessel in the vicinity of the impeller.

For some applications, such a blood pump is configured to be placed within a subject's renal vein and to pump blood from the subject's renal vein into the subject's vena cava, e.g., as described herein with reference to FIGS. 13A-B. For some applications, such a blood pump is configured to be placed within a subject's vena cava upstream of the junctions of the vena cava with all of the subject's renal veins, and to pump blood in a retrograde (i.e., upstream) direction, e.g., as described herein with reference to FIG. 22B. Alternatively or additionally, such a blood pump is configured to be placed within a subject's vena cava downstream of the junctions of the vena cava with all of the subject's renal veins, and to pump blood in an antegrade (i.e., downstream) direction, e.g. as described herein with reference to FIG. 22C. For some such applications, an occlusion element is configured to be placed within the subject's vena cava upstream of the junctions of the vena cava with all of the subject's renal veins, and to partially occlude the vena cava, e.g., as described herein with reference to FIG. 22C. For some applications, upstream and downstream blood pumps are disposed on a single catheter, e.g., as described herein with reference to FIGS. 1A-C. Alternatively, an upstream occlusion element, and a downstream blood pump are disposed on a single catheter, e.g., as described herein with reference to FIGS. 5A-B, 16, and 22C. In accordance with some applications, the catheter is introduced into the vena cava from a vein that is above the inferior vena cava (e.g., the jugular vein or the subclavian vein), in which case the upstream pump or occlusion element is disposed upon the catheter distally with respect to the downstream blood pump, as described herein with reference to FIGS. 1A and 3. Alternatively, the catheter is introduced into the vena cava from a vein that is below the junctions of the vena cava with the subject's renal veins (e.g., the femoral vein), in which case the upstream pump or occlusion element is disposed upon the catheter proximally with respect to the downstream blood pump, e.g., as described herein with reference to FIG. 4.

For some applications, an occlusion element and/or a blood pump is placed in a subject's infra-renal vena cava (i.e., within the vena cava, upstream of junctions of the vena cava with all of a subject's renal veins). Typically, the occlusion element and/or blood pump is inserted into the vena cava of a subject suffering from acute heart failure. Typically, in patients suffering from acute heart failure, elevated systemic venous pressures cause increased renal parenchymal pressure and increased intraabdominal pressure, factors that can contribute to deterioration of renal perfusion and function. In addition, high systemic venous pressures may impede lymphatic drainage of pulmonary interstitial fluid resulting in aggravation and prolongation of pulmonary congestion in patients with acute pulmonary edema. For some applications, the occlusion element is configured to cause partial occlusion of the infra-renal vena cava, and/or the blood pump is used to pump blood in a retrograde direction within the infra-renal vena cava. Typically, use of the occlusion element and/or the blood pump in this manner reduces cardiac preload, by causing lower body venous pooling. Typically, reducing cardiac preload ameliorates pulmonary congestion and/or improve cardiac loading conditions and function.

Typically, an indication of cardiac preload is measured, for example, by measuring central venous pressure, renal venous pressure, cardiac diameter and/or cardiac volume. Further typically, an indication of cardiac output and/or arterial pressure is measured, for example, by measuring arterial blood flow, minute flow, arterial flow velocity, and/or arterial blood pressure. For some applications, a control unit monitors the indication of cardiac preload, and modulates the extent to which the occlusion element occludes the infra-renal vena cava, and/or the rate at which the blood pump pumps blood, in response thereto. For some applications, the control unit sets the extent to which the occlusion element occludes the infra-renal vena cava, and/or the rate at which the blood pump pumps blood, by determining the highest degree of obstruction, or reverse blood flow, attainable without decreasing cardiac output and/or arterial pressure by more than a given threshold.

For some applications, a downstream pump is placed downstream of the junctions of the vena cava with all of the subject's renal veins, and pumps blood through the vena cava, in the downstream direction, away from the junctions of the vena cava with the renal veins. Furthermore, an occlusion element is placed upstream of the junctions of the vena cava with all of the subject's renal veins and is configured to partially occlude the subject's vena cava upstream of the junctions of the vena cava with the subject's renal veins. The occlusion element is configured to partially occlude the subject's vena cava such that, in response to the pumping of the downstream blood pump, there is not a substantial increase of blood flow from the subject's lower body toward the subject heart, but such that a region of low pressure within the vena cava is generated, between the occlusion element and the downstream blood pump, within which the blood pressure is lower than the subject's central venous pressure. Typically, by generating a region of low pressure, blood flow from the renal veins into the vena cava increases, thereby lowering renal blood pressure and enhancing renal perfusion. For some applications, the combination of the downstream pump and the upstream occlusion element is configured such that the overall effect of the downstream pump and the upstream occlusion element is that (a) central venous pressure is lowered relative to lower body venous pressure (e.g., by the pumping of the downstream pump not fully compensating for the reduction in pressure caused by the occlusion of the vena cava by the upstream occlusion element), and (b) renal venous pressure is lowered relative to lower body venous pressure and central venous pressure, due to the region of low pressure being generated within the vena cava, between the occlusion element and the downstream blood pump.

For some applications, a control unit controls the extent to which the occlusion element occludes the vena cava and the rate at which the pump pumps blood, responsively to one or more of the parameters detected by sensors. For example, based upon the parameters detected by the sensors, the control unit may control the extent to which the occlusion element occludes the vena cava and the rate at which the pump pumps blood, such that the ratio between renal venous pressure and lower body pressure is a first ratio, and such that the ratio between central venous pressure and lower body pressure is a second ratio, which is different from the first ratio. Typically, the first ratio is designated based upon the extent to which it is desirable to decrease the subject's renal venous pressure, such as to increase renal perfusion, in accordance with the techniques described herein. Further typically, the second ratio is designated based upon the extent to which it is desirable to decrease the subject's cardiac preload, in accordance with the techniques described herein.

In general, in the specification and in the claims of the present application, the term "proximal" and related terms, when used with reference to a device or a portion thereof, should be interpreted to mean an end of the device or the portion thereof that, when inserted into a subject's body, is typically closer to a location through which the device is inserted into the subject's body. The term "distal" and related terms, when used with reference to a device or a portion thereof, should be interpreted to mean an end of the device or the portion thereof that, when inserted into a subject's body, is typically further from the location through which the device is inserted into the subject's body.

In general, in the specification and in the claims of the present application, the term "downstream" and related terms, when used with reference to a blood vessel, or with reference to a portion of a device that is configured to be placed inside a blood vessel, should be interpreted to mean a location within the blood vessel, or a portion of the device that is intended for placement at a location within the blood vessel, that is downstream, with respect to the direction of antegrade blood flow through the blood vessel, relative to a different location within the blood vessel. The term "upstream" and related terms, when used with reference to a blood vessel, or with reference to a portion of a device that is configured to be placed inside a blood vessel, should be interpreted to mean a location within the blood vessel, or a portion of the device that is intended for placement at a location within the blood vessel, that is upstream with respect to the direction of antegrade blood flow through the blood vessel, relative to a different location within the blood vessel.

There is therefore provided, in accordance with some applications of the present invention, apparatus including:

a blood pump configured to be placed inside a blood vessel of a subject, the blood pump including:
an impeller configured to pump blood by rotating; and
a support cage that is shaped to define:
a narrow portion that is configured to be disposed around the impeller, and to maintain a separation between a wall of the blood vessel and the impeller, and
a radial extension from the narrow portion of the support cage that extends radially outward with respect to the narrow portion of the support cage, the radial extension being configured to substantially maintain a longitudinal axis of the impeller in alignment with a local longitudinal axis of the blood vessel by contacting the wall of the blood vessel.

For some applications, the narrow portion of the support cage and the radial extension include a single integrated component. For some applications, the narrow portion of the support cage and the radial extension include respective components that are formed separately from each other.

For some applications, the radial extension includes a plurality of radially-protruding support arms that protrude from the narrow portion of the support cage. For some applications, the radial extension includes a frustoconical cage that is disposed around the narrow portion of the support cage.

For some applications, a stiffness of the narrow portion of the support cage is greater than a stiffness of the radial extension, such that the narrow portion of the cage is configured to maintain the separation between the wall of the blood vessel and the impeller, even if the wall of the vessel exerts pressure upon the support cage that causes the radial extension to deform.

For some applications, the apparatus further includes a material coupled to the support cage, the material defining a hole therethrough in a vicinity of the impeller, the material being configured to occlude backflow of blood around an outside of the impeller, and to allow antegrade blood flow in the vicinity of the impeller.

For some applications, the blood pump is configured to be placed within a renal vein of the subject and to pump blood from the subject's renal vein into a vena cava of the subject.

For some applications, the blood pump is configured to be placed within a vena cava of the subject upstream of junctions of the vena cava with all renal veins of the subject, the pump being configured to pump blood through the vena cava in a retrograde direction.

For some applications, the blood pump is configured to be placed within a vena cava of the subject downstream of junctions of the vena cava with all renal veins of the subject, the pump being configured to pump blood through the vena cava in an antegrade direction.

For some applications, the apparatus further includes an additional blood pump, the additional blood pump being configured to be placed within the subject's vena cava upstream of junctions of the vena cava with all renal veins of the subject, the additional blood pump being configured to pump blood through the vena cava in a retrograde direction.

For some applications, the apparatus further includes an occlusion element configured to be placed within the subject's vena cava upstream of junctions of the vena cava with all renal veins of the subject, the occlusion element being configured to partially occlude blood flow through the vena cava upstream of junctions of the vena cava with all renal veins of the subject.

For some applications, the radial extension includes a bulbous extension that extends radially and distally from the narrow portion of the support cage. For some applications, a maximum diameter of the bulbous extension, when the bulbous extension is in a radially non-constrained configuration thereof, is at least 1.1 times greater than a maximum diameter of the narrow portion of the support cage, when the narrow portion is in a radially non-constrained configuration thereof.

There is further provided, in accordance with some applications of the present invention method including:

inserting a blood pump into a blood vessel of a subject, the blood pump including:

an impeller configured to pump blood by rotating; and a support cage that is shaped to define:

a narrow portion that is configured to be disposed around the impeller, and to maintain a separation between a wall of the blood vessel and the impeller, and a radial extension from the narrow portion of the support cage that extends radially outward with respect to the narrow portion of the support cage, the extension being configured to substantially maintain a longitudinal axis of the impeller in alignment with a local longitudinal axis of the blood vessel by contacting the wall of the blood vessel; and pumping blood through the blood vessel, by rotating the impeller, by operating the blood pump.

There is further provided, in accordance with some applications of the present invention, a method including:

identifying a subject as suffering from acute heart failure;

in response thereto, reducing cardiac preload of the subject by partially occluding a vena cava of the subject at an infra-renal location;

monitoring one or more physiological parameters of the subject selected from the group consisting of: lower body venous pressure, central venous pressure, central venous blood flow, renal venous pressure, cardiac diameter, cardiac volume, arterial pressure, and arterial blood flow; and modulating an extent to which the vena cava is occluded at the infra-renal location, responsively to the one or more physiological parameters.

There is further provided, in accordance with some applications of the present invention, a method including:

identifying a subject as suffering from acute heart failure;

in response thereto, reducing cardiac preload of the subject by pumping blood in a retrograde direction at an infra-renal location within a vena cava of the subject;

monitoring one or more physiological parameters of the subject selected from the group consisting of: lower body venous pressure, central venous pressure, central venous blood flow, renal venous pressure, cardiac diameter, cardiac volume, arterial pressure, and arterial blood flow; and modulating a rate at which the blood is pumped in the retrograde direction at the infra-renal location, responsively to the one or more physiological parameters.

There is further provided, in accordance with some applications of the present invention, apparatus including:

an occlusion element configured to reduce cardiac preload of a subject by being placed in a vena cava of the subject at an infra-renal location, and to partially occlude the subject's vena cava at the infra-renal location;

one or more sensors configured to monitor one or more physiological parameters of the subject selected from the group consisting of: lower body venous pressure, central venous pressure, central venous blood flow, renal venous pressure, cardiac diameter, cardiac volume, arterial pressure, and arterial blood flow; and a computer processor configured to modulate an extent to which the occlusion element occludes the vena cava at the infra-renal location, responsively to the one or more physiological parameters.

For some applications, the occlusion element includes a balloon configured to be inflated at the infra-renal location, and the computer processor is configured to modulate the extent to which the occlusion element occludes the vena cava at the infra-renal location by modulating an extent to which the balloon is inflated.

For some applications, the occlusion element includes an expandable frame having material covered thereto, and the computer processor is configured to modulate the extent to which the occlusion element occludes the vena cava at the infra-renal location by modulating an extent to which the frame is expanded.

For some applications, the occlusion element includes a nozzle, and the computer processor is configured to modulate the extent to which the occlusion element occludes the vena cava at the infra-renal location by modulating a diameter of an opening of the nozzle.

For some applications, the one or more sensors are configured to monitor a parameter of the subject that is indicative of cardiac output of the subject, and the computer processor is configured to modulate the extent to which the occlusion element occludes the vena cava at the infra-renal location responsively to the parameter that is indicative of the cardiac output.

For some applications, the one or more sensors include a thermodilution catheter configured to monitor the parameter that is indicative of the cardiac output.

For some applications, the one or more sensors are further configured to monitor a parameter of the subject that is indicative of cardiac preload of the subject, and the computer processor is configured to modulate the extent to which the occlusion element occludes the vena cava at the infra-renal location responsively to the parameter that is indicative of the cardiac output in combination with the parameter that is indicative of the cardiac preload.

For some applications, the one or more sensors are configured to monitor a parameter of the subject that is indicative of arterial blood pressure of the subject, and the computer processor is configured to modulate the extent to which the occlusion element occludes the vena cava at the infra-renal location responsively to the parameter that is indicative of the arterial blood pressure.

For some applications, the one or more sensors are further configured to monitor a parameter of the subject that is indicative of cardiac preload of the subject, and the computer processor is configured to modulate the extent to which the occlusion element occludes the vena cava at the infra-renal location responsively to the parameter that is indicative of the arterial blood pressure in combination with the parameter that is indicative of the cardiac preload.

For some applications, the apparatus further includes a blood pump configured to be placed at a location within the vena cava that is downstream of junctions of the vena cava with all renal veins of the subject, the blood pump being configured to reduce the subject's renal venous pressure relative to the subject's central venous pressure by pumping blood in an antegrade direction through the vena cava from the location.

For some applications, the computer processor is further configured to modulate a rate at which the blood pump pumps blood in the antegrade direction, responsively to the one or more physiological parameters.

For some applications, the computer processor is configured to modulate the rate at which the blood pump pumps blood in the antegrade direction responsively to the one or more physiological parameters in coordination with modulating the extent to which the vena cava is occluded at the infra-renal location responsively to the one or more physiological parameters, such as to:

maintain a first ratio between the subject's renal venous pressure and the subject's lower body venous pressure, and maintain a second ratio between the subject's central venous pressure and the subject's lower body venous pressure, the second ratio being different from the first ratio.

There is further provided, in accordance with some applications of the present invention, apparatus including:

a blood pump configured to reduce cardiac preload of a subject by being placed at an infra-renal location within a vena cava of the subject, and pumping blood in a retrograde direction from the location;

one or more sensors configured to monitor one or more physiological parameters of the subject selected from the group consisting of: lower body venous pressure, central venous pressure, central venous blood flow, renal venous pressure, cardiac diameter, cardiac volume, arterial pressure, and arterial blood flow; and a computer processor configured to modulate a rate at which the blood pump pumps blood in the retrograde direction, responsively to the one or more physiological parameters.

For some applications, the one or more sensors are configured to monitor a parameter of the subject that is indicative of cardiac output of the subject, and the computer processor is configured to modulate the rate at which the blood pump pumps blood in the retrograde direction responsively to the parameter that is indicative of the cardiac output.

For some applications, the one or more sensors include a thermodilution catheter configured to monitor the parameter that is indicative of the cardiac output.

For some applications, the one or more sensors are further configured to monitor a parameter of the subject that is indicative of cardiac preload of the subject, and the computer processor is configured to modulate at which the blood is pumped includes modulating the rate at which the blood pump pumps blood in the retrograde direction responsively to the parameter that is indicative of the cardiac output in combination with the parameter that is indicative of the cardiac preload.

For some applications, the one or more sensors are configured to monitor a parameter of the subject that is indicative of arterial blood pressure of the subject, and the computer processor is configured to modulate the rate at which the blood pump pumps blood in the retrograde direction responsively to the parameter that is indicative of the arterial blood pressure.

For some applications, the one or more sensors are further configured to monitor a parameter of the subject that is indicative of cardiac preload of the subject, and the computer processor is configured to modulate at which the blood is pumped includes modulating the rate at which the blood pump pumps blood in the retrograde direction responsively to the parameter that is indicative of the arterial blood pressure in combination with the parameter that is indicative of the cardiac preload.

For some applications, the apparatus further includes a second blood pump configured to be placed at a downstream location within the vena cava that is downstream of junctions of the vena cava with all renal veins of the subject, the second blood pump being configured to reduce the subject's renal venous pressure relative to the subject's central venous pressure by pumping blood in an antegrade direction through the vena cava from the location that is downstream of junctions of the vena cava with all renal veins of the subject.

For some applications, the computer processor is further configured to modulate a rate at which the second blood pump pumps blood in the antegrade direction from the downstream location, responsively to the one or more physiological parameters.

For some applications, the computer processor is configured to modulate the rate at which the second blood pump pumps blood in the antegrade direction from the downstream location responsively to the one or more physiological parameters by modulating the rate at which the blood is pumped in the antegrade direction through the vena cava from the downstream location in coordination with modulating the rate at which blood is pumped in the retrograde direction at the infra-renal location within the subject's vena cava, such as to:

maintain a first ratio between the subject's renal venous pressure and the subject's lower body venous pressure, and maintain a second ratio between the subject's central venous pressure and the subject's lower body venous pressure, the second ratio being different from the first ratio.

The present invention will be more fully understood from the following detailed description of embodiments thereof, taken together with the drawings, in which:

BRIEF DESCRIPTION OF THE DRAWINGS

FIGS. 2A, 2B, 2C, 2D, and 2E are schematic illustrations of arrangements of impellers that are configured to pump blood in opposite directions from one another, in accordance with some applications of the present invention;

DETAILED DESCRIPTION OF EMBODIMENTS

Figure 1A:
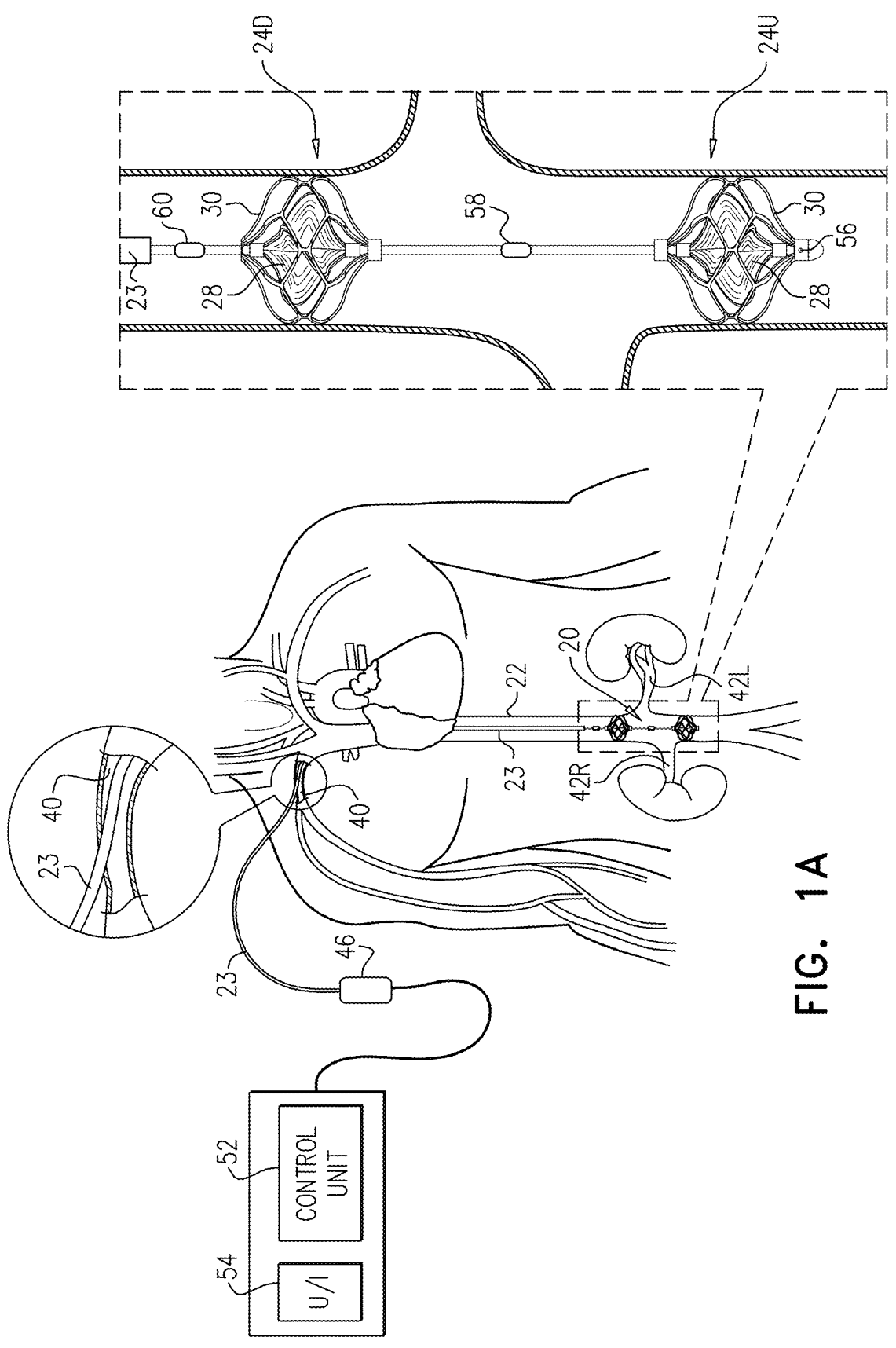
FIGS. 1A, 1B, and 1C are schematic illustrations of a blood-pump catheter placed within a subject's vena cava, an upstream pump being disposed upon the catheter, distally to a downstream pump, in accordance with some applications of the present invention.
Figure 1B:
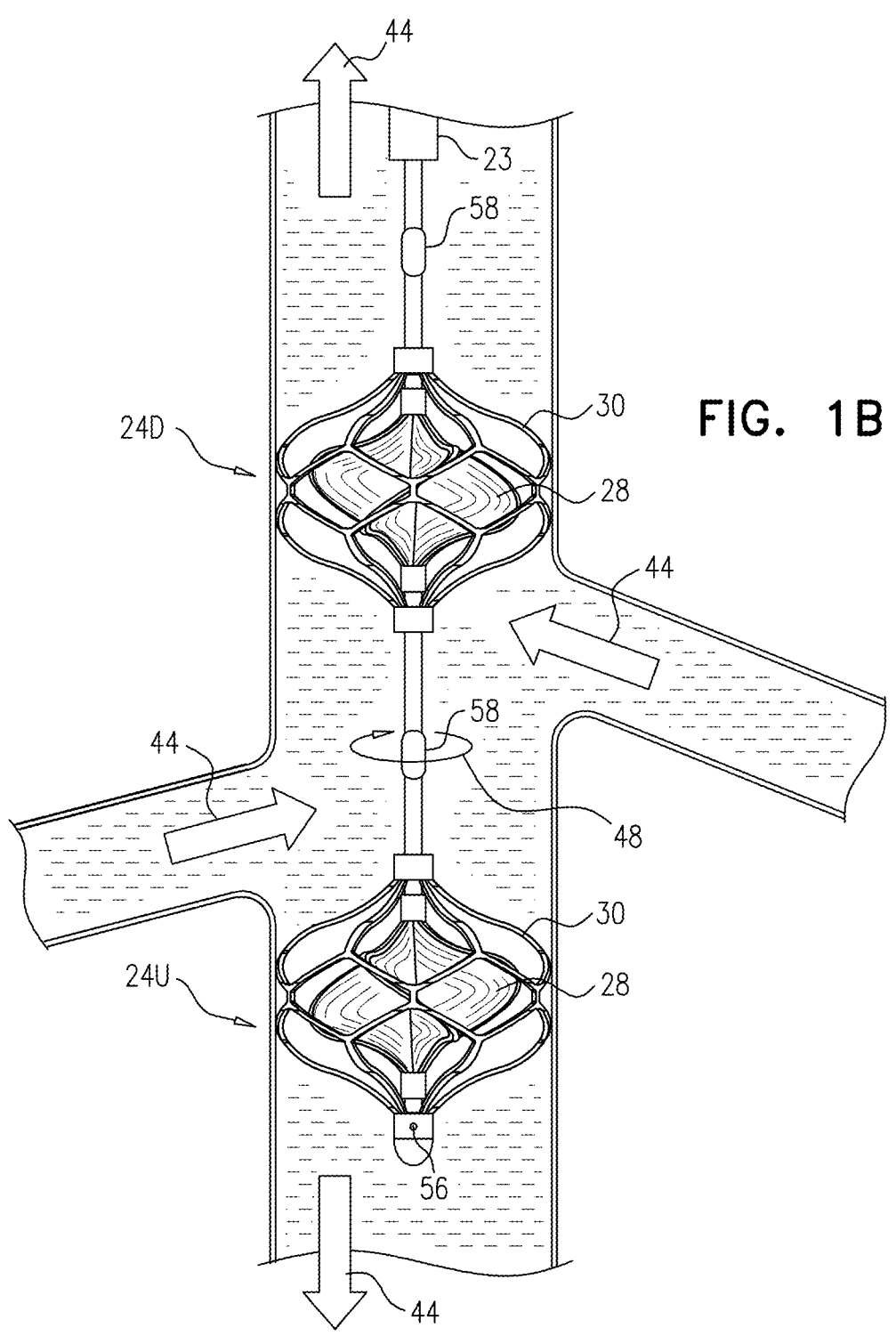
Figure 1C:
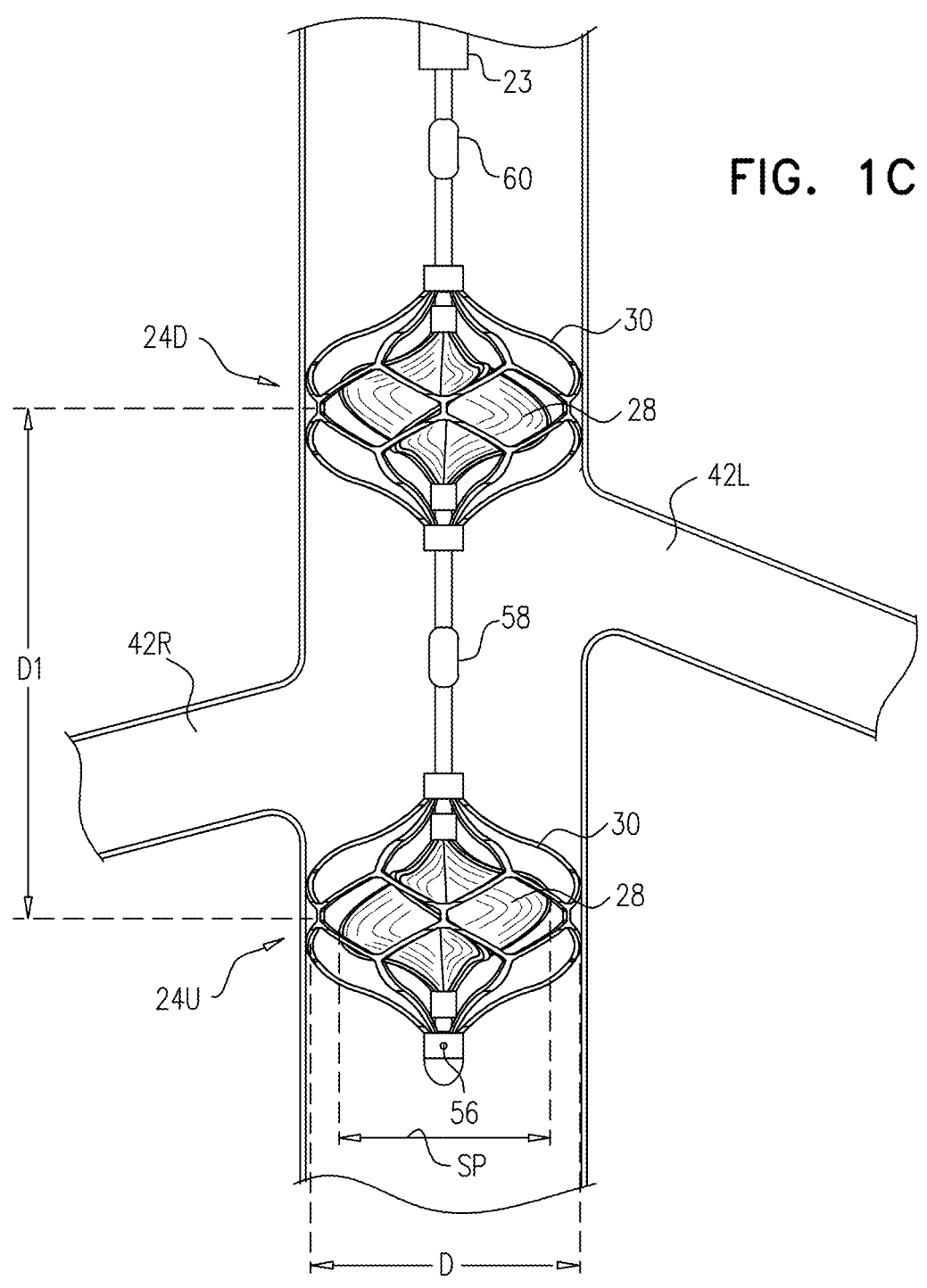

Reference is made to FIGS. 1A-C, which are schematic illustrations of a blood-pump catheter 20 placed within a subject's vena cava 22, via a guide catheter 23, an upstream pump 24U being disposed upon the catheter, distally to a downstream pump 24D, in accordance with some applications of the present invention. Typically, the distal portion of blood-pump catheter 20 is configured to be straight, when the catheter is in a non-constrained state, such that both the upstream and the downstream pumps are disposed along the axis of the catheter, within the vena cava.

Each of the upstream and downstream pumps 24U and 24D typically includes a radially-expandable impeller 28 disposed inside a radially-expandable impeller cage 30. Typically, impeller 28 and impeller cage 30 are shape-set such as to assume radially expanded configurations thereof in the absence of any radially constraining force acting upon the impeller and the cage. The blood pumps are inserted into the subject's vena cava, while the blood pumps are in radially constrained configurations inside the guide catheter, and are configured to assume substantially radially non-constrained configurations by being released from the guide catheter inside the subject's vena cava. (It is noted that, for some applications, in the vena cava, the blood pumps may not be fully radially non-constrained, due to the walls of the vena cava applying a radially compressive force to the blood pumps.) For some applications, an engagement mechanism engages the impeller and the cage with respect to one another, such that in response to the cage becoming radially constrained, the impeller becomes radially constrained, e.g., in accordance with apparatus and methods described in described in US 2016/0022890 to Schwammenthal, which is incorporated herein by reference.

It is noted that the term "impeller" is generally used herein to denote a bladed rotor, as shown in FIGS. 1A-C, for example. When the bladed rotor is placed inside a blood vessel (such as vena cava 22) and rotated, the bladed rotor functions as an impeller, by modifying the flow of blood through the blood vessel, and/or by generating a pressure difference between the upstream end and the downstream end of the impeller.

It is noted that reference numeral 24 is generally used to denote a blood pump in the present application. When a pump that is placed upstream is being referred to, reference numeral 24U is used, and when a pump that is placed downstream is being referred to, reference numeral 24D is used. Similarly, reference numeral 28 is generally used to denote an impeller in the present application. When an impeller that is placed upstream is being referred to, reference numeral 28U is used, and when an impeller that is placed downstream is being referred to, reference numeral 28D is used.

Blood-pump catheter 20 is typically placed inside the subject's vena cava 22, and operated therein, in order to provide acute treatment of a subject suffering from cardiac dysfunction, congestive heart failure, low renal blood flow, high renal vascular resistance, arterial hypertension, diabetes, and/or kidney dysfunction. For example, the blood-pump catheter may be placed inside the subject's vena cava, and operated therein, for a period of more than one hour (e.g., more than one day), less than one week (e.g., less than four days), and/or between one hour and one week (e.g., between one day and four days). For some applications, the blood-pump catheter is chronically placed inside the subject's vena cava in order to provide chronic treatment of a subject suffering from cardiac dysfunction, congestive heart failure, low renal blood flow, high renal vascular resistance, arterial hypertension, diabetes, and/or kidney dysfunction. For some applications, a course of treatment is applied to a subject over several weeks, several months, or several years, during which the blood-pump catheter is intermittently placed inside the subject's vena cava, and the subject is intermittently treated in accordance with the techniques described herein. For example, the subject may be intermittently treated at intervals of several days, several weeks, or several months.

For some applications, blood-pump catheter 20 is inserted into vena cava 22, via the subject's subclavian vein 40, as shown in FIG. 1A. Typically, the blood-pump catheter is inserted under fluoroscopic imaging. Alternatively, the blood-pump catheter is inserted under ultrasound imaging, such as to reduce exposure of the subject to radiation and/or contrast agent. The catheter is placed into the vena cava such that upstream pump 24U is disposed upstream of the junctions of the vena cava and all of the subject's renal veins 42, and such that downstream pump 24D is disposed downstream of the junctions of the vena cava and all of the subject's renal veins. Typically, the upstream pump is configured to pump blood through the vena cava in the upstream direction, away from the renal veins, and the downstream pump is configured to pump blood through the vena cava in the downstream direction, away from the renal veins.

The effect of both of pumps 24U and 24D pumping blood in the above-described manner is that, between the pumps, and adjacent to the junctions of the vena cava with the renal veins, there is a low-pressure region of the vena cava, within which blood pressure is lower than the subject's central venous pressure. Functionally, this region may be viewed as a compartment within the vena cava within which blood pressure is controlled (by controlling pumps 24U and 24D), regardless of the blood pressure elsewhere within the vena cava. This typically increases blood flow from the renal veins into the vena cava, lowers pressure within the subject's renal veins, and causes renal perfusion to increase. The effect of pumps 24U and 24D on blood flow through the renal veins and the vena cava is indicated by arrows 44 in FIG. 1B.

As described hereinabove, the effect of operating blood pumps 24U and 24D is that between the pumps there is a low-pressure region of the vena cava. However, typically, the pumps are operated simultaneously such that the pressure within other portions of the vena cava is substantially unchanged relative to when blood-pump catheter 20 is not in operation. For example, the pumps are typically operated simultaneously such that the pressure within the vena cava downstream of downstream pump 24D is not substantially increased relative to when blood-pump catheter 20 is not in operation. Similarly, the pumps are typically operated simultaneously such that the pressure within the vena cava upstream of upstream pump 24U is not substantially increased relative to when blood-pump catheter 20 is not in operation. This is because the pumps are typically operated simultaneously such that outside of the region between the two pumps, the effects of the pumping by the upstream and downstream pumps cancel each other with respect to pressure. It is noted that there is likely to be some increase in the pressure within the vena cava downstream of downstream pump and upstream of upstream pump due to the increased blood flow from the renal veins into the vena cava.

Similarly, the pumps are typically operated simultaneously such that venous return to the vena cava from regions upstream of the upstream pump and downstream from the downstream pump is substantially unchanged relative to when blood-pump catheter 20 is not in operation. In this manner, the pumps are typically operated simultaneously such as to have a generally synergistic effect on pressure and flow in the region between the pumps, but to have an antagonistic effect on pressure and flow outside of the region, such that, outside of the region, the effects of the two pumps typically substantially cancel each other out.

Typically, blood-pump catheter 20 pumps blood in a manner that enhances the rate of blood flow through the renal veins and into the vena cava, but does not cause a substantial change in the direction of the blood flow relative to the natural direction of flow through the renal veins, or from the renal veins to the vena cava (i.e., relative to blood flow in the absence of pumping by the blood-pump catheter). That is to say, the blood-pump catheter pumps blood in the downstream direction through the renal veins and then directly into the portion of the vena cava that is adjacent to the renal veins, rather than, for example, pumping the blood from the renal veins into a different portion of the subject's veins (such as, an upstream location within the vena cava). It is noted that, due to the pumping of the downstream pump in the downstream direction, there is likely to be some blood flow from the renal veins to the portion of the vena cava that is below the renal veins. Further typically, blood-pump catheter 20 enhances blood flow through the renal veins without removing blood from the subject's venous system into a non-venous receptacle, such as an artificial lumen of a blood pump.

As described hereinabove, typically blood-pump catheter 20 is placed inside the vena cava of a subject suffering from cardiac dysfunction, congestive heart failure, low renal blood flow, high renal vascular resistance, arterial hypertension, diabetes, and/or kidney dysfunction. Typically, operating the blood-pump catheter in the vena cava of such a subject causes a lowering and flattening of the subject's renal vein pressure profile, even though the subject's central venous pressure is elevated and has additional effects, e.g., as described with reference to FIG. 4B of US 2016/0022890 to Schwammenthal, which is incorporated herein by reference.

Typically, each of upstream and downstream pumps 24U and 24D includes an impeller 28, for example, any one of the impellers described in US 2016/0022890 to Schwammenthal, which is incorporated herein by reference. In accordance with respective applications, impeller 28 may have a single blade, two blades (e.g., as described in US 2016/0022890 to Schwammenthal, which is incorporated herein by reference), three blades (e.g., as described in US 2016/

0022890 to Schwammenthal), or more than three blades. For some applications, one or both of blood pumps 24U and 24D includes more than one impeller. Typically, ceteris paribus, by using more than one impeller in at least one of the pumps, in order to generate a given flow of blood with the pump, the force that impacts each of the impellers within the pump is smaller than if a single impeller were to be used in the pump.

For some applications, one or both of the pumps includes radially expandable impeller cage 30. For some applications, impeller cage 30 is configured to hold open the inner wall of the vena cava and to separate the inner wall of the vena cava from the impeller, such that the vena cava does not become injured by the impeller. Alternatively, the impeller cage is sized such that the cage is not used to hold open the inner wall of the vena cava (the diameter of the cage being less than that of the vena cava, at least in some subjects). Even in such cases, the cage typically functions to separate the inner wall of the vena cava from the impeller, for example, in case the walls of the vena cava at least partially collapse inwardly, such that the vena cava does not become injured by the impeller. Such applications are described with reference to FIGS. 9A-B, for example.

As described hereinabove, typically, impeller 28 and cage 30 are shape-set such as to assume radially expanded configurations thereof in the absence of any radially con-straining force acting upon the impeller and/or the cage. For some applications, an engagement mechanism engages the impeller and the cage with respect to one another, such that in response to the cage becoming radially constrained the impeller becomes radially constrained, e.g., in accordance with apparatus and methods described in described in US 2016/0022890 to Schwammenthal, which is incorporated herein by reference. For some applications, the stiffness of cage 30 is sufficiently great that pressure exerted upon the cage by the inner wall of the vena cava does not deform the cage. The cage thereby protects the impeller from being deformed by pressure from the inner wall of the vena cava. Such applications are described hereinbelow, with reference to FIGS. 9A-B, for example.

Referring now to FIG. 1C, typically, when blood-pump catheter 20 is placed inside vena cava 22, impeller 28 and impeller cage 30 are substantially radially non-constrained, due to the relatively low radial force exerted by the vena cava wall on the cage. (It is noted that, for some applications, in the vena cava, the impeller and/or impeller cage may not be fully radially non-constrained, due to the walls of the vena cava applying a radially compressive force to the blood pumps.) For some applications, the impeller cage is config-ured to come into contact with the inner wall of the vena cava, when the impeller cage assumes its radially non-constrained configuration inside the vena cava, e.g., as shown in FIG. 1C. For such applications, a span SP of impeller 28, when the impeller is in a non-constrained configuration thereof inside the vena cava is more than 14 mm (e.g., more than 16 mm), and/or less than 28 mm (e.g., less than 22 mm), e.g., 14-28 mm, or 16-22 mm. Typically, for such applications, a diameter D of cage 30, when the cage is in a non-constrained configuration thereof inside the vena cava is more than 14 mm (e.g., more than 16 mm), and/or less than 40 mm (e.g., less than 35 mm), e.g., 14-40 mm, or 16-35 mm. Further typically, when blood-pump catheter 20 is used to enhance blood flow from the renal veins into the subject's vena cava, as described herein, a longitudinal distance D1 between centers of the impellers of the upstream and downstream pumps, measured along the longitudinal axis of the catheter, is typically more than 3 cm (e.g., more than 6 cm), and/or less than 18 cm (e.g., less than 14 cm), e.g., 3-18 cm, or 6-14 cm. For some applications, distance D1 is adjustable and is set based upon measure-ments that are performed upon a subject.

Figures 9A, 9B:
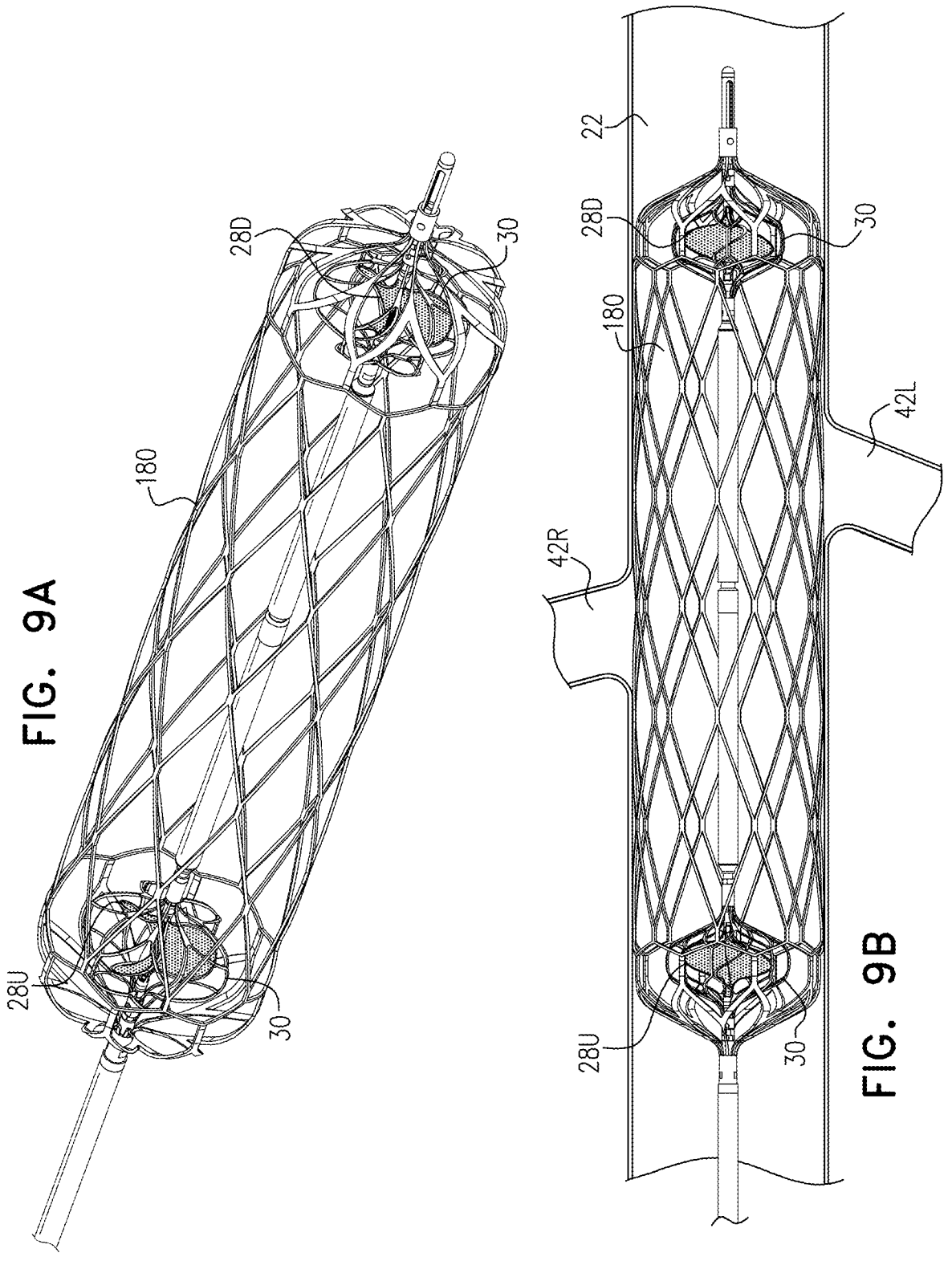
FIGS. 9A and 9B are schematic illustrations of a blood-pump catheter for placing within a subject's vena cava, an upstream impeller being disposed upon the catheter, proximally to a downstream impeller, the upstream and downstream impellers being disposed within a support cage that supports the walls of a portion of the vena cava between the upstream and downstream impellers, in accordance with some applications of the present invention.

For some applications, impeller cage 30 is configured such that in its radially non-constrained configuration, the cage has a diameter that is less than that of the vena cava at least in some subjects, for example, as described hereinbe-low with reference to FIGS. 9A-B.

For some applications, impellers 28 of upstream and downstream pumps 24U and 24D are rotated at respective rotation rates, in order to cause the pumping of blood in the upstream and downstream directions to be performed at respective rates. Alternatively, the impellers are rotated at the same rotation rate (and, typically, in the same direction), but the impellers are sized, shaped, and/or oriented such that the rate at which blood is pumped, respectively, in the upstream and downstream directions, by the respective impellers, is not equal.

Typically, a control unit 52 and a user interface 54 are disposed outside the subject's body. Further typically, the control unit receives inputs from one or more pressure sensors 56, 58, and/or 60, e.g., as shown in FIGS. 1A-C.

In accordance with some applications:
   (a) a pressure sensor 56 is disposed on the upstream side of upstream blood pump 24U and is configured to measure pressure within the vena cava upstream of the low-pressure region of the vena cava, which is typically indicative of venous pressure within the subject's lower body;
   (b) a pressure sensor 58 disposed between the two blood pumps, and is configured to measure pressure within the low-pressure region of the vena cava between the two blood pumps, which is typically indicative of blood pressure within the subject's renal veins; and/or
   (c) a pressure sensor 60 is disposed on the downstream side of downstream blood pump 24D and is configured to measure pressure within the vena cava downstream of the low-pressure region of the vena cava, which is typically indicative of the subject's central venous pressure close to the subject's right heart.

For some applications, blood-pump catheter 20 includes pressure sensor 58 disposed between the two blood pumps, and is configured to measure pressure within the low-pressure region of the vena cava between the two blood pumps, which is typically indicative of blood pressure within the subject's renal veins, and the blood-pump cath-eter does not include pressure sensor 56, or pressure sensor 60.

For some applications, control unit 52 controls pumps 24U and 24D, e.g., by controlling rotation of impellers 28, responsively to one or more of the above-described inputs. Typically, user interface 54 displays the subject's current lower-body venous pressure, renal venous pressure, and/or central venous pressure, based upon the signals generated by sensors 56, 58, and/or 60. Typically, based upon the current values of the subject's lower-body venous pressure, renal venous pressure, and/or central venous pressure, a user (such as a healthcare professional) inputs a target value for the subject's renal venous pressure, via the user interface. In response thereto, control unit 52 controls the speed of the rotation of the impellers, such that the impellers pump blood away from the renal veins at a flow rate that is such as to reduce the renal venous pressure toward the target level, as indicated by the user. For some applications, in response to a signal received from sensor 60 indicating that the central venous pressure is at the target renal venous pressure, the control unit stops the impellers rotating. For some applications, the control unit receives an input from an additional sensor (such as a flow sensor and/or an oxygen-saturation sensor, and/or a thermal flow sensor, e.g., as described with reference to FIGS. 22Ai-22Cii of US 2016/0022890 to Schwammenthal, which is incorporated herein by reference), and the control unit controls the speed of the rotation of the impellers responsively to an input from the additional sensor.

It is noted that control unit 52 typically includes a computer processor that comprises circuitry and that is configured to execute the actions described herein. Typically, the operations described herein that are performed by the computer processor transform the physical state of a memory, which is a real physical article that is in communication with the computer processor, to have a different magnetic polarity, electrical charge, or the like, depending on the technology of the memory that is used. Control unit 52 is typically a hardware device programmed with computer program instructions to produce a special-purpose computer. For example, when programmed to perform the techniques described herein, control unit 52 typically acts as a special-purpose, renal-venous-pressure-modulating computer processor.

It is further noted that user interface 54 typically includes any type of user interface configured to receive inputs from a user and/or to provide outputs to the user. For example, the user interface may include one or more input devices (such as a keyboard, a mouse, a trackball, a joystick, a touchscreen monitor, a touchpad, a voice-command interface, a smartphone, a tablet computer, and/or other types of input devices that are known in the art), and/or one or more output devices (such as a monitor, an audio output device, a smartphone, a tablet computer, and/or other types of output devices that are known in the art).

Reference is now made to FIGS. 2A, 2B, 2C, 2D, and 2E, which are schematic illustrations of arrangements of impellers 28U and 28D that are configured to pump blood in opposite directions from one another, in accordance with some applications of the present invention. (For illustrative purposes, FIGS. 2A-E show the impellers in the absence of impeller cages, although typically, the impellers are used together with impeller cages 30, as described hereinabove.)

Typically, impellers of pumps 24U and 24D are coupled to one or more motors 46 (FIG. 1A), which impart rotational motion to the impellers, via one or more rotation shafts, the shaft(s) being housed inside blood-pump catheter 20. In accordance with respective applications, the motors are disposed outside of the subject's body (as shown), or are placed inside the subject's body (not shown).

Referring now to FIG. 2A, for some applications, impellers 28 of upstream and downstream pumps 24U and 24D are rotated in the same rotational direction as one another, as viewed from an external reference point (e.g., in the direction of arrow 48 (i.e., clockwise), or counterclockwise), but the impellers are disposed on the catheter such that the rotation of the impellers in this direction of rotation causes the impellers to pump blood in respective, opposite directions. It is noted that the rotational direction of the impellers "as viewed from an external reference point" should be interpreted to mean the direction of rotational motion of the impellers as observed from any point that is not undergoing the same rotational motion as either of the impellers.

Typically, for such applications, a single motor is used to rotate both of the impellers. A shaft 50 is used to impart the rotational motion from the motor to the proximal impeller. An additional shaft 51, which is in series with shaft 50, couples the proximal impeller to the distal impeller and imparts the rotational motion from the proximal impeller to the distal impeller. For some applications, by using a single series of shafts to impart rotation to impellers 28 of both upstream and downstream pumps 24U and 24D, the diameter of blood-pump catheter 20 is reduced relative to if parallel shafts were used, in order to impart rotation to the upstream and downstream impellers.

For some applications, the angles and/or orientations of the impeller blades of impellers 28 of upstream and downstream pumps 24U and 24D may be such as to cause the impellers to pump blood in respective, opposite directions. For some applications, as shown in FIG. 2A, each impeller is shaped and/or oriented in the mirror image of the other, the axis of reflection being orthogonal to the longitudinal axes of the impellers. For such applications, the upstream and downstream impellers are of opposing handedness to one another, a first one of the impellers being a left-handed impeller, and the other one of the impellers being a right-handed impeller. It is generally the case that impellers of opposing handedness that are positioned parallel to one another, facing the same direction as one another, and rotating in opposite rotational directions from one another, generate flow in the same direction as one another. In accordance with some applications of the present invention, the upstream and downstream impellers are disposed upon shaft 51 such that the impellers are facing in opposite directions to one another. As described hereinabove, for such applications, the impellers are typically rotated in the same rotational direction as one another, as viewed from an external reference point. The result of the impellers (a) being of opposing handedness to one another, and (b) facing in opposite directions, is that, when the impellers are rotated in the same direction as one another about an axis defined by shaft 51, the impellers pump blood in opposite directions from one another.

Typically, the blades of the downstream impeller are oriented such that, as the downstream impeller rotates in the direction of arrow 48, the downstream impeller pumps in the downstream direction. The blades of the upstream impeller are oriented such that, as the upstream impeller rotates in the direction of arrow 48, the upstream impeller pumps in the upstream direction.

Referring now to FIG. 2B, for some applications, the upstream impeller 28U and the downstream impeller 28D are rotated in opposite directions from one another, as viewed from an external reference point, in order to generate blood flow in opposite directions from one another. For example, impellers that are of the same handedness as one another and that are facing the same direction as one another may be used. For some such applications, a single motor is used to rotate both of the impellers. Shaft 50 is used to impart the rotational motion from the motor to the proximal impeller. Additional shaft 51, which is in series with shaft 50, couples the proximal impeller to the distal impeller and imparts the rotational motion from the proximal impeller to the distal impeller. A gear mechanism 70 is disposed between the proximal impeller and the distal impeller (e.g., along shaft 51, as shown), and is configured to reverse the direction of rotational motion that is imparted from the proximal impeller to the distal impeller, such that the distal impeller rotates in an opposite direction of rotation to the direction of rotation of the proximal impeller. For example, as shown in FIG. 2B, the downstream impeller (which in this case is the proximal impeller) rotates in the direction of arrow 48, while the upstream impeller rotates in the direction of arrow 72 (i.e., the opposite direction to that of arrow 48).

Figure 2E:
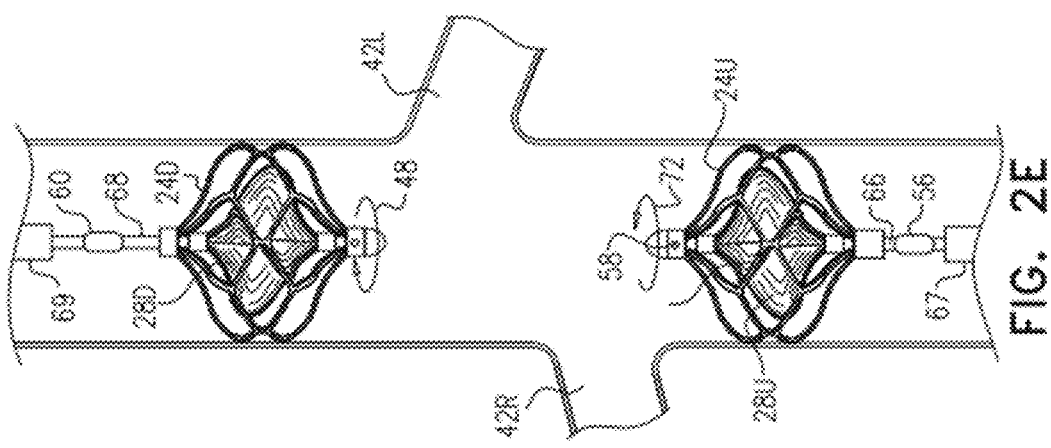

For some applications, it is advantageous to rotate the downstream impeller in the opposite direction from the upstream impeller (e.g., as shown in FIG. 2B), rather than rotating the downstream impellers in the same direction as the upstream impeller (e.g., as shown in FIG. 2A). For some applications, if the downstream impeller rotates in the same direction as the upstream impeller, then blood flowing through the vena cava that impacts the downstream impeller is already at least partially undergoing rotational motion in the direction of rotation of the downstream impeller (by virtue of the rotational motion imparted to the blood flow by the upstream impeller). Due to the blood already undergoing rotational motion in the same direction as the downstream impeller, the effect of the rotational motion of the downstream impeller upon the blood flow is less than if the blood flow had not already been undergoing the rotational motion in the same direction as the downstream impeller, or if the blood had been undergoing rotational motion in the opposite direction to that of the downstream impeller. Therefore, for some applications, the upstream and downstream impellers are configured to pump blood in opposite directions from one another by rotating in opposite directions from one another, e.g., using techniques described with reference to any one of FIG. 2B, 2D, or 2E.

Referring now to FIG. 2C, for some applications, impellers 28 of upstream and downstream pumps 24U and 24D are rotated in the same rotational direction as one another, as viewed from an external reference point (e.g., in the direction of arrow 48 (i.e., clockwise), or counterclockwise), but the impellers are disposed on the catheter such that the rotation of the impellers in this direction of rotation causes the impellers to pump blood in respective, opposite directions. The configuration shown in FIG. 2C is generally similar to that of FIG. 2A, with the impellers being of opposing handedness to one another, and facing in opposite directions to one another. However, in the configuration shown in FIG. 2C, an additional impeller 74 is disposed between the upstream and the downstream impellers. Impeller 74 is configured not to be actively rotated. As indicated by the two-dimensional arrows indicating the direction of blood flow, blood that is rotated by the upstream impeller impacts impeller 74, causing the rotational motion of the blood flow to be at least partially reduced. Due to the reduction in the rotational motion of the blood flow, the effect of the rotation of the downstream impeller upon the blood flow is greater than it would be in the absence of impeller 74.

Figure 2D:
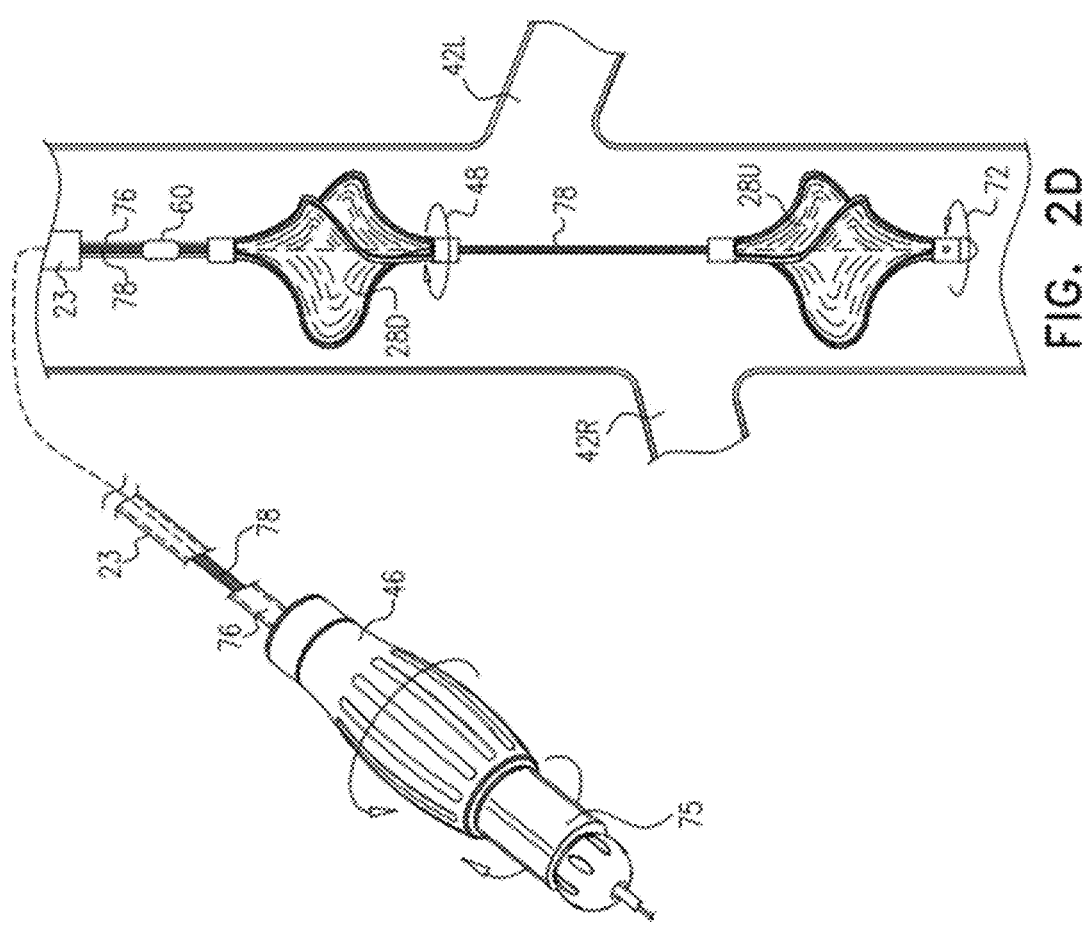

Referring now to FIG. 2D, for some applications, motor 46 is used to rotate a first one of the impellers in a first direction. For example, as shown in FIG. 2D, motor 46 is used to rotate downstream impeller 28D in the direction of arrow 48 (i.e., clockwise). A second motor 75 is used to rotate the second one of the impellers in the opposite direction to the first direction. For example, as shown in FIG. 2D, motor 75 is used to rotate upstream impeller 28U in the direction of arrow 72 (i.e., counterclockwise). A first rotation shaft 76 extends from first motor 46 to the first impeller and imparts the rotational motion in the first direction to the first impeller. A second rotation shaft 78 extends from second motor 75 to the second impeller and imparts the rotational motion in the opposite direction to the first direction to the second impeller. Typically, within blood-pump catheter 20, first rotation shaft 76 and second rotation shaft 78 are coaxial with one another, as shown. For some such applications, impellers that are of the same handedness as one another are used as the upstream impeller 28U and the downstream impeller 28D.

Reference is now made to FIG. 2E, which is a schematic illustration of upstream and downstream pumps 24U and 24D being disposed on respective catheters 66 and 68, in accordance with some applications of the present invention. For some applications, a first catheter 66 is inserted into vena cava 22 through a guide catheter 67 that is inserted via the subject's femoral vein, or via another vein that is below the subject's inferior vena cava. Upstream blood pump 24U is disposed on the first catheter, and is configured to be placed within the vena cava upstream of the junctions of the vena cava with all of the subject's renal veins, and to pump blood through the vena cava in the manner described hereinabove. A second catheter 68 is inserted into the vena cava through a guide catheter 69 that is inserted via the subject's jugular vein, subclavian vein, or via a different vein that is above the subject's inferior vena cava. Downstream blood pump 24D is disposed on the second catheter, and is configured to be placed within the vena cava downstream of the junctions of the vena cava with all of the subject's renal veins, and to pump blood through the vena cava in the manner described hereinabove.

For applications in which the upstream and downstream blood pumps include impellers, typically, respective motors 46 and 75 (e.g., as shown FIG. 2D) are used to control rotation of the impellers. For some applications, as described hereinabove with reference to FIG. 2D, motor 46 rotates the downstream pump in a first direction (e.g., the direction of arrow 48), and motor 75 rotates the upstream pump in the opposite direction (e.g., the direction of arrow 72). Further typically, control unit 52 (FIG. 1A) controls both pumps (e.g., by controlling the rates of rotation of the impellers). For some applications, pressure sensors 56, 58 and 60 are disposed upon the first and/or second catheters, and are configured to detect indications of, respectively, lower body venous pressure, renal venous pressure, and central venous pressure. The control unit is configured to control the operation of the upstream and downstream pumps responsively to the detected indications, in accordance with the techniques described hereinabove.

For some applications, the impellers of the upstream and downstream pumps are configured to pump blood in the same direction as one another, e.g., in the antegrade direction to enhance blood flow through a vessel.

Figure 3:
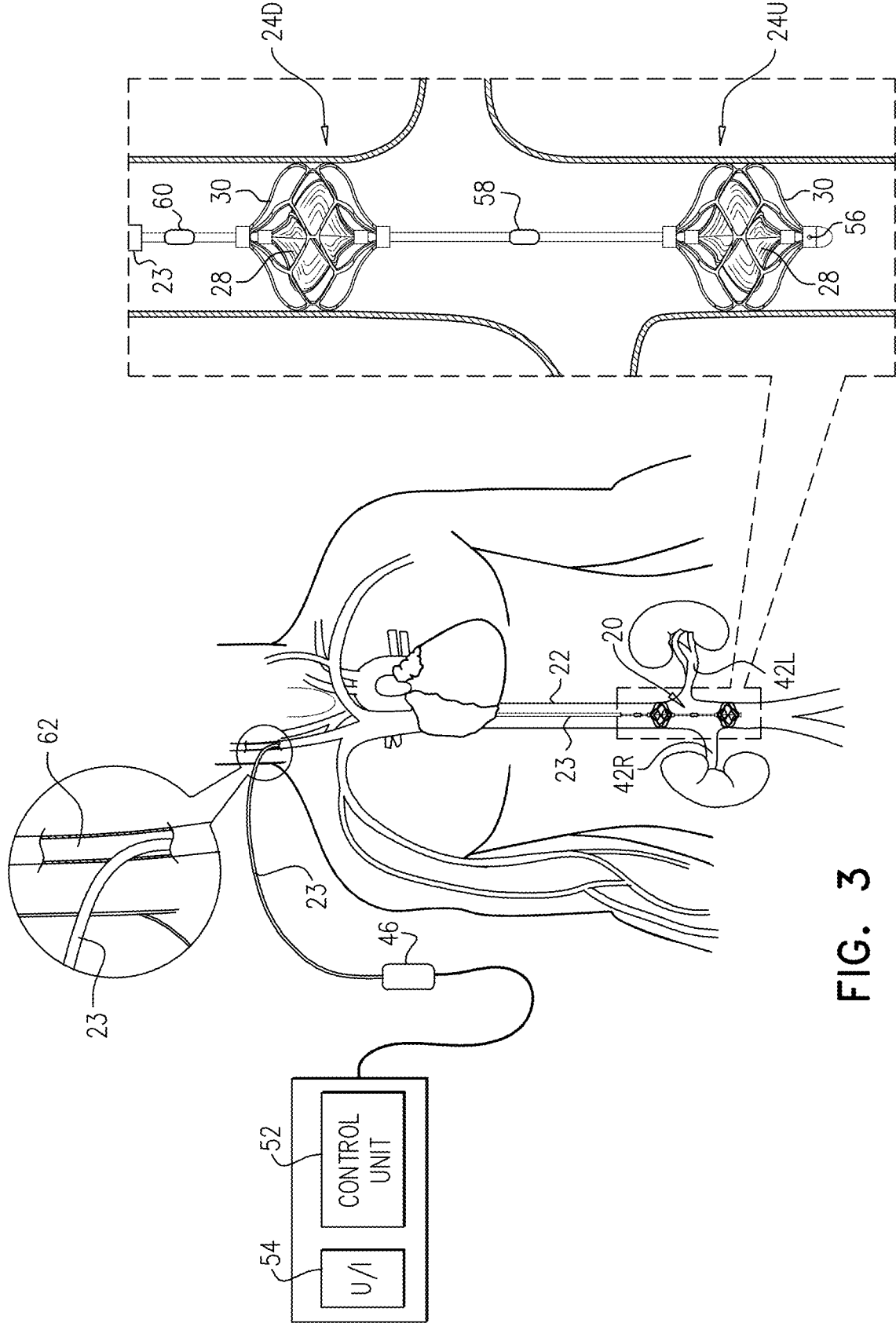
FIG. 3 is a schematic illustration of the catheter of FIGS. 1A, 1B, and 1C inserted into the subject's vena cava via the subject's right jugular vein, in accordance with some applications of the present invention.

Reference is now made to FIG. 3, which is a schematic illustration of blood-pump catheter 20 being inserted into the subject's vena cava 22 via the subject's right jugular vein 62 (through guide catheter 23), in accordance with some applications of the present invention. For some applications, instead of being inserted via the subclavian vein (as shown in FIG. 1A, for example), blood-pump catheter 20 is inserted into the vena cava via the subject's right jugular vein, or via another vein that is above the subject's inferior vena cava. In all other aspects, blood-pump catheter 20 and the functioning thereof are generally as described with reference to FIGS. 1A-C.

Figure 4:
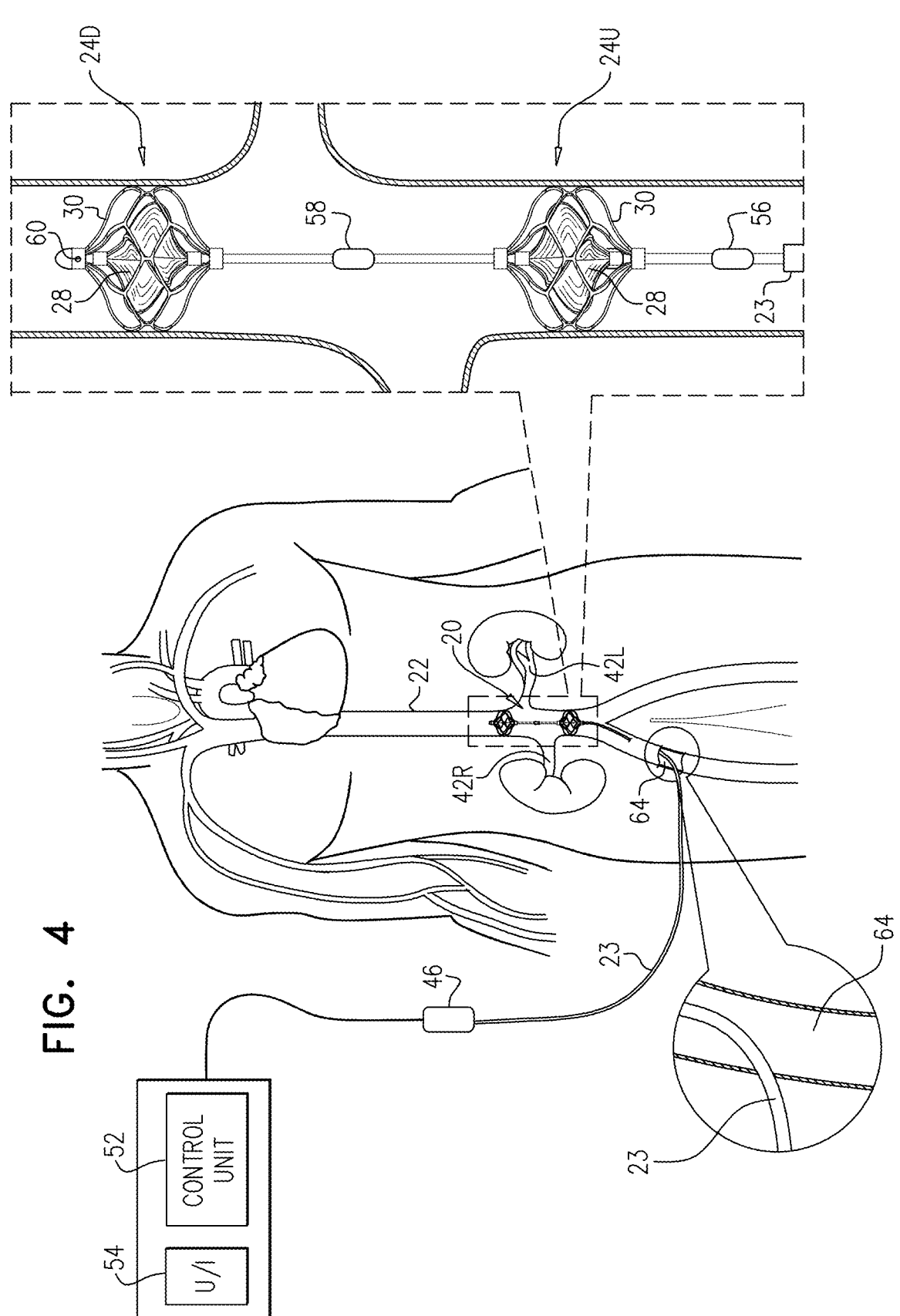
FIG. 4 is a schematic illustration of a blood-pump catheter inserted into a subject's vena cava via the subject's femoral vein, a downstream pump being disposed upon the catheter distally to an upstream pump, in accordance with some applications of the present invention.

Reference is now made to FIG. 4, which is a schematic illustration of blood-pump catheter 20 being inserted into the subject's vena cava 22 via the subject's femoral vein 64 (through guide catheter 23), downstream pump 24D being disposed upon the catheter distally to upstream pump 24U, in accordance with some applications of the present invention. For some applications, instead of being inserted via the subclavian vein (as shown in FIG. 1A, for example), blood-pump catheter 20 is inserted into the vena cava, via the subject's femoral vein 64, or via another vein that is below the subject's inferior vena cava. Typically, downstream blood pump 24D is disposed on blood-pump catheter 20 distally to upstream blood pump 24U. Blood-pump catheter 20 is configured to be placed within the vena cava, such that the upstream pump is disposed upstream of the junctions of the vena cava with all of the subject's renal veins 42, and such that the downstream pump is disposed downstream of the junctions of the vena cava with all of the subject's renal veins. Other than the dispositions of the upstream and downstream blood pumps with respect to blood-pump catheter 20, blood-pump catheter 20, as shown in FIG. 4, and the functioning thereof, is generally similar to that described with reference to blood-pump catheter 20 as shown in FIGS. 1A-C.

Figure 5B:
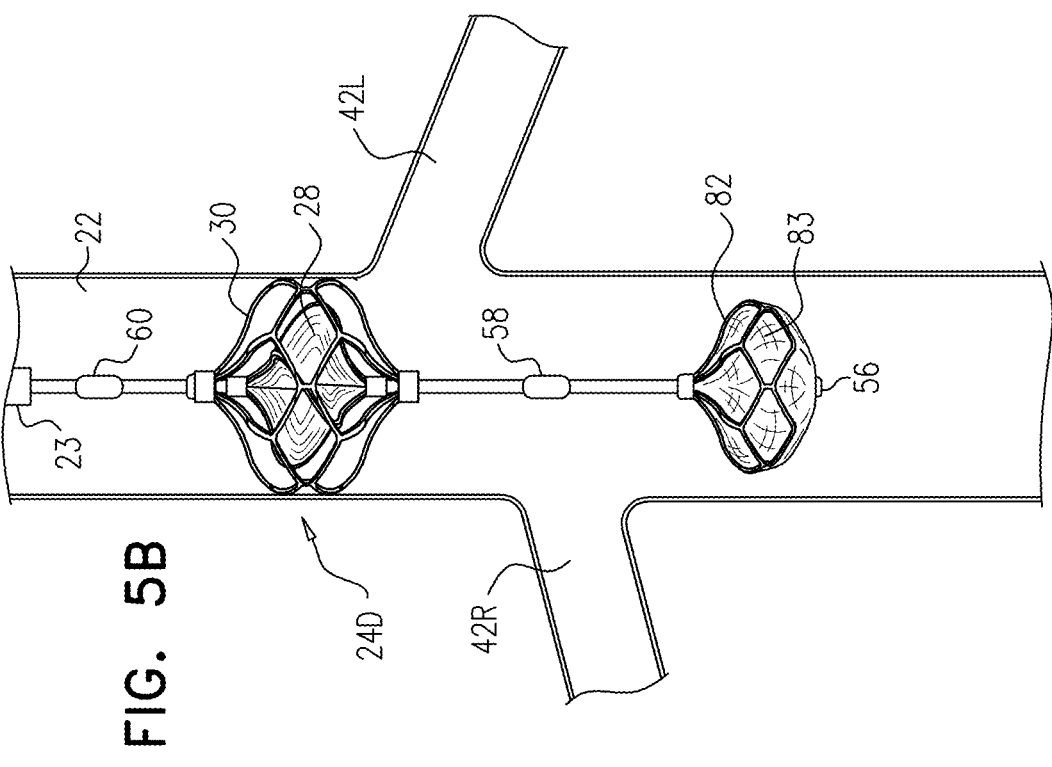
FIGS. 5A and 5B are schematic illustrations of a catheter that includes a downstream pump and an occlusion element, such as a balloon (FIG. 5A), or a covered frame (FIG. 5B), in accordance with some applications of the present invention.
Figure 5A:
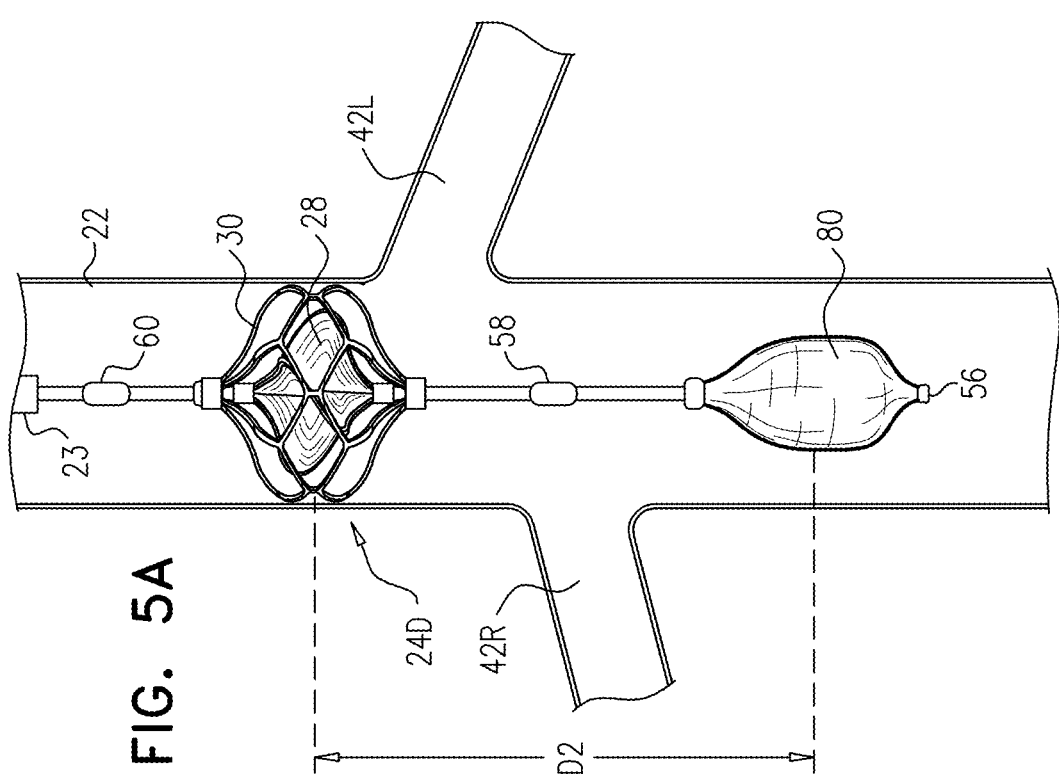

Reference is now made to FIGS. 5A-B, which are schematic illustrations of blood-pump catheter 20, the catheter including downstream pump 24D and an occlusion element, such as a balloon 80 (FIG. 5A), or a covered frame 82 (FIG. 5B), in accordance with some applications of the present invention. For some applications (not shown), a nozzle is used as the upstream occlusion element, e.g., as described in co-pending PCT Patent Application No. PCT/IL2017/051092 to Tuval, filed Sep. 28, 2017, which is incorporated herein by reference. For some applications, downstream pump is placed inside vena cava 22, downstream of the junctions of the vena cava with all of the subject's renal veins. The downstream pump pumps blood through the vena cava, in the downstream direction, away from the junctions of the vena cava with the renal veins, in the manner described hereinabove. As an alternative to, or in addition to, using an upstream pump as described hereinabove, the occlusion element is placed inside the vena cava upstream of the junctions of the vena cava with the subject's renal veins. Typically, the occlusion element is configured to partially occlude the subject's vena cava upstream of the junctions of the vena cava with the subject's renal veins. The occlusion element is configured to partially occlude the subject's vena cava such that, in response to the pumping of the downstream blood pump, there is not a substantial increase of blood flow from the subject's lower body toward the subject heart, but such that a region of low pressure within the vena cava is generated, between the occlusion element and the downstream blood pump, within which the blood pressure is lower than the subject's central venous pressure. Typically, by generating a region of low pressure, blood flow from the renal veins into the vena cava increases, thereby lowering renal blood pressure and enhancing renal perfusion. It is noted that the occlusion element is configured to partially occlude, but not to totally occlude, the vena cava, in such a manner as to generate a region of low pressure within the vena cava, but to allow a substantial flow of blood through the vena cava.

When blood-pump catheter 20 is used to enhance blood flow from the renal veins into the subject's vena cava, as described herein, a longitudinal distance D2 between the longitudinal center of the impeller of the downstream pump and the longitudinal center of the occlusion element, measured along the longitudinal axis of the catheter, is typically more than 3 cm (e.g., more than 6 cm), and/or less than 18 cm (e.g., less than 14 cm), e.g., 3-18 cm, or 6-14 cm.

For some applications, the occlusion element is balloon 80, as shown in FIG. 5A. Alternatively or additionally, the occlusion element is covered frame 82, as shown in FIG. 5B. For example, the frame may be a frame (e.g., a rigid or semi-rigid frame) made of a shape-memory element (such as nitinol) that is covered with a material (e.g., a blood-impermeable material) 83 (e.g., polyester, polyurethane, and/or a different polymer).

As described hereinabove, typically, the occlusion element is configured to partially occlude the vena cava upstream of the junctions of the vena cava with the subject's renal veins. For some applications, the diameter to which the occlusion element is expanded is controllable. For example, inflation of the balloon may be controllable, or the frame may be expandable (e.g., by heating the frame, or by applying an electrical current to the frame). For some applications, the extent to which the occlusion element occludes the vena cava is controlled by a control unit (e.g., control unit 52) responsively to the blood pressure detected by blood pressure sensor 56, 58, and/or 60, in response to an input from a different sensor (such as a flow sensor and/or an oxygen-saturation sensor, and/or a thermal flow sensor, e.g., as described with reference to FIGS. 22Ai-Cii of US 2016/0022890 to Schwammenthal, which is incorporated herein by reference), and/or in response to an input from a user. For some applications, the rate at which pump 24D pumps blood away from the renal veins (e.g., the rate at which impeller 28 of the pump is rotated), and/or the extent to which the occlusion element occludes the vena cava, is controlled by a control unit responsively to the blood pressure detected by blood pressure sensor 56, 58, and/or 60, in response to an input from a different sensor (such as a flow sensor and/or an oxygen-saturation sensor, and/or a thermal flow sensor, e.g., as described with reference to FIGS. 22Ai-Cii of US 2016/0022890 to Schwammenthal, which is incorporated herein by reference), and/or in response to an input from a user.

Although FIGS. 5A and 5B show the downstream blood pump and the occlusion element disposed on a catheter that is inserted into the vena cava from above the junctions of the vena cava with the subject's renal veins (e.g., via the subject's subclavian vein or jugular vein), for some applications, the downstream blood pump and the occlusion element are disposed on a catheter that is inserted into the vena cava from below the junctions of the vena cava with the subject's renal veins (e.g., via the subject's femoral vein), mutatis mutandis. Alternatively or additionally, the occlusion element is disposed on a first catheter which is inserted into the vena cava from below the junctions of the vena cava with the subject's renal veins (e.g., via the subject's femoral vein), and the downstream blood pump is disposed on a second catheter, which inserted into the vena cava from above the junctions of the vena cava with the subject's renal veins (e.g., via the subject's subclavian vein, or jugular vein).

As described hereinabove, for some applications, using impellers that rotate in the same direction as one another for upstream and downstream pumps causes blood flow that impacts the downstream impeller to already be undergoing rotational motion in the same direction as the downstream impeller, which, in turn, may cause the effect of the rotational motion of the downstream impeller upon the blood to be less than if the blood flow had not been undergoing the rotational motion in the same direction as the downstream impeller. For some applications, an occlusion element, such as a balloon 80 (FIG. 5A), covered frame 82 (FIG. 5B), or a nozzle (not shown, e.g., as described in co-pending PCT Patent Application No. PCT/IL2017/051092 to Tuval, filed Sep. 28, 2017, which is incorporated herein by reference) is used instead of an upstream impeller, such that the blood flow that impacts the downstream impeller is not undergoing rotational motion in the same direction as the downstream impeller.

For some applications, an occlusion element is placed within the vena cava upstream of junctions of the vena cava with all of the renal veins even in the absence of a downstream blood pump, for example, as described in further detail hereinbelow with reference to FIG. 22A.

Figure 6:
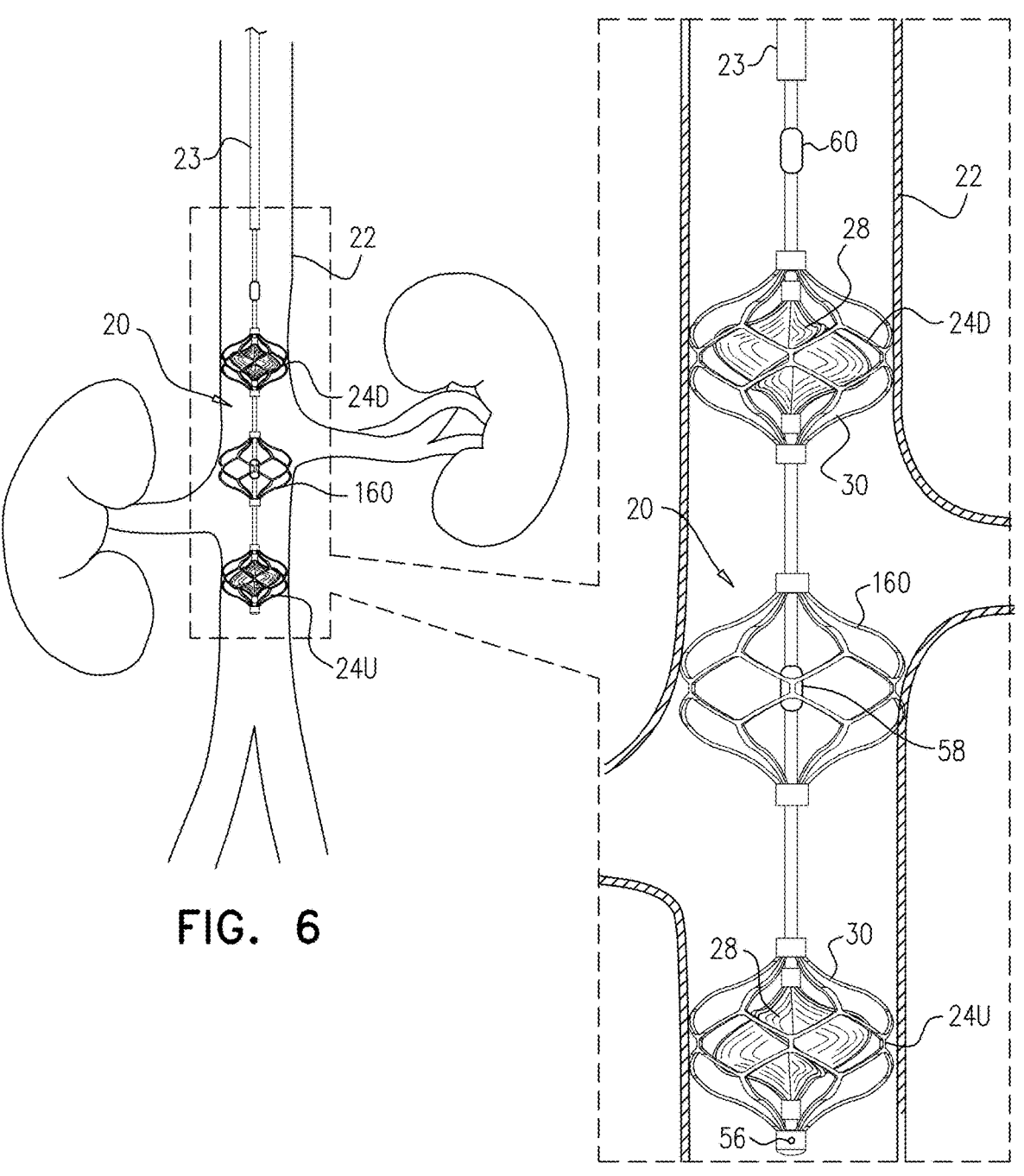
FIG. 6 is a schematic illustration of a blood-pump catheter placed within a subject's vena cava, an upstream pump being disposed upon the catheter, distally to a downstream pump, and a support stent being disposed upon the catheter between the upstream and downstream pumps, in accordance with some applications of the present invention.

Reference is now made to FIG. 6, which is a schematic illustration of blood-pump catheter 20 placed within a subject's vena cava 22, upstream pump 24U being disposed upon the catheter, distally to downstream pump 24D, and a support stent 160 being disposed upon the catheter between the upstream and downstream pumps, in accordance with some applications of the present invention. As described hereinabove, typically during operation of pumps 24U and 24D, a region of low pressure is generated within the vena cava between the two pumps. Typically, stent 160 is configured to support the walls of the vena cava at the low-pressure region, such that the vena cava does not become obstructed at the low-pressure region, due to the walls of the vena cava collapsing. For example, if, due to the pumping of the upstream and downstream pumps, the pressure within the vena cava in the region between the pumps falls below the subject's intraabdominal pressure, then the walls of the vena cava may collapse in the absence of a support structure, such as support stent 160.

For some applications, stent 160 has a generally similar shape to cage 30. Although FIG. 6 shows stent 160 disposed upon a blood-pump catheter, upon which the upstream pump is disposed distally to the downstream pump, for some applications, stent 160 is disposed upon a blood-pump catheter, upon which the downstream pump is disposed distally to the upstream pump, as described hereinabove. Similarly, although FIG. 6 shows stent 160 disposed upon a blood-pump catheter, upon which the upstream pump is disposed distally to the downstream pump, for some applications, stent 160 is disposed upon a blood-pump catheter upon which an occlusion element and a downstream pump are disposed, e.g., as shown in FIGS. 5A-B.

Reference is now made to FIGS. 7A, 7B, 7C, 7D, and 7E, which are schematic illustrations of blood-pump catheter 20 placed within a subject's vena cava 22, upstream impeller 28U being disposed upon the catheter, distally to downstream impeller 28D, the upstream and downstream impellers being disposed within a support cage 170 that supports the walls of a portion of the vena cava between the upstream and downstream impellers, in accordance with some applications of the present invention. Although FIGS. 7A-E shows support cage 170 disposed upon a blood-pump catheter, upon which the upstream pump is disposed distally to the downstream pump, for some applications, support cage 170 is disposed upon a blood-pump catheter, upon which the downstream pump is disposed distally to the upstream pump, as described hereinabove. Similarly, although FIGS. 7A-E shows support cage 170 disposed upon a blood-pump catheter, upon which the upstream pump is disposed distally to the downstream pump, for some applications, support cage 170 is disposed upon a blood-pump catheter upon which an occlusion element and a downstream pump are disposed, e.g., as shown in FIGS. 5A-B.

As described hereinabove, typically during operation of pumps 24U and 24D, a region of low pressure is generated within the vena cava between the two pumps. Typically, support cage 170 is configured to support the walls of the vena cava at the low-pressure region, such that the vena cava does not become obstructed at the low-pressure region, due to the walls of the vena cava collapsing. For example, if, due to the pumping of the upstream and downstream pumps, the pressure within the vena cava in the region between the pumps falls below the subject's intraabdominal pressure, then the walls of the vena cava may collapse in the absence of a support structure, such as support cage 170.

Typically, the support cage is radially expandable and is shaped to assume a radially expanded configuration thereof in the absence of any radially constraining force acting upon the support cage. For example, the support cage may be made of a shape memory material, e.g., a shape memory metal or alloy (such as, nitinol). Typically, the support cage is configured to extend longitudinally along more than 50 percent of a region between the first and second impellers, the support cage being configured to thereby support the inner wall of the vena cava in an open configuration in the region between the first and second impellers. For some applications, support cage is configured to extend at least from the longitudinal center of the downstream impeller to the longitudinal center of the upstream impeller. For some applications, a length L1 (FIG. 7B) of the support cage, when the cage is in a substantially non-constrained configuration thereof inside the vena cava, is more than 3 cm (e.g., more than 6 cm), and/or less than 18 cm (e.g., less than 14 cm), e.g., 3-18 cm, or 6-14 cm. Further typically, a diameter D3 (FIG. 7B) of support cage 170, when the cage is in a substantially non-constrained configuration thereof inside the vena cava, is more than 14 mm (e.g., more than 16 mm), and/or less than 35 mm (e.g., less than 25 mm), e.g., 14-35 mm, or 16-25 mm. It is noted that, for some applications, the support cage may be somewhat radially constrained when disposed within the vena cava due to radial compression of the walls of the vena cava upon the support cage.

Figure 7A:
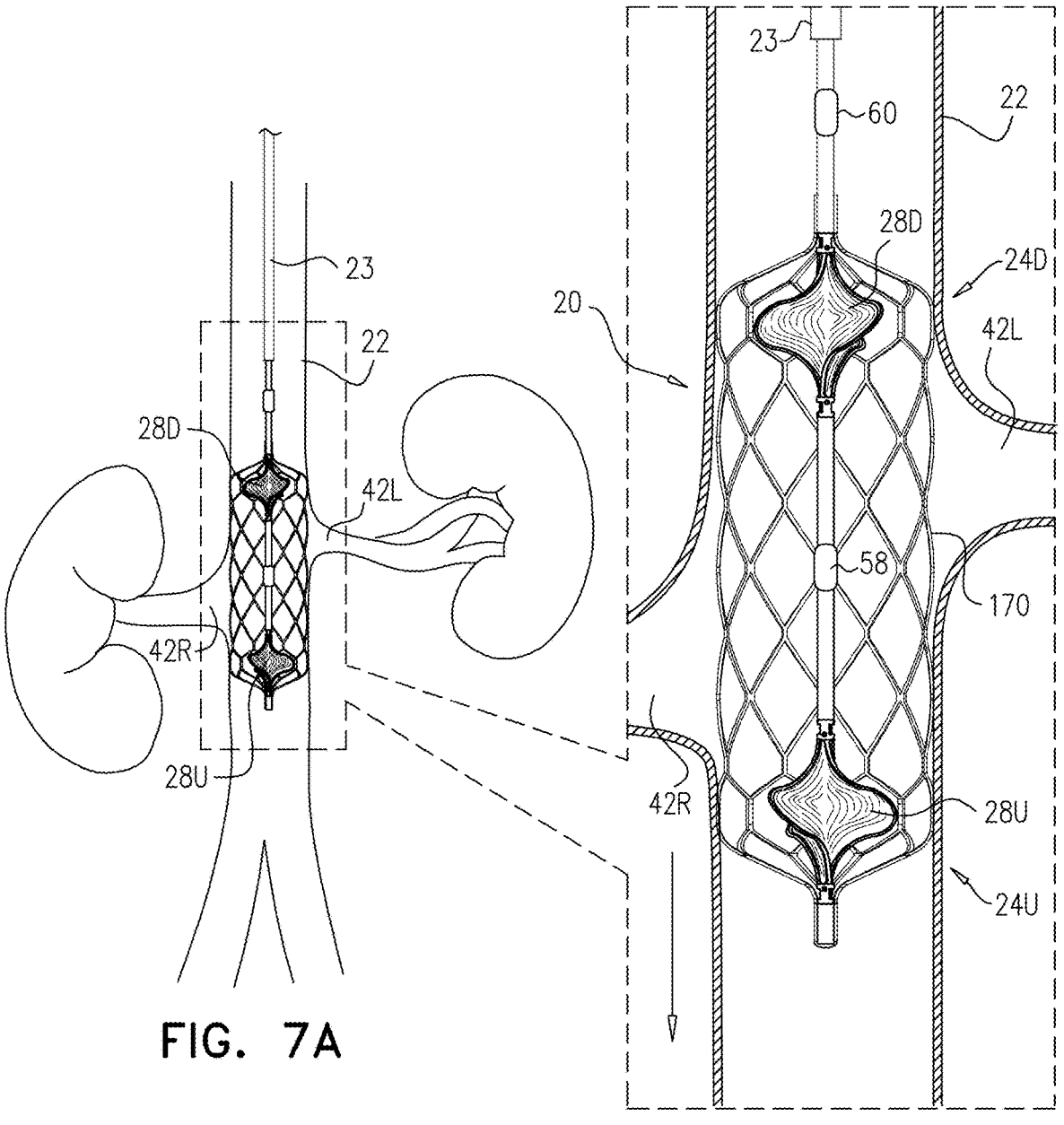
FIGS. 7A, 7B, 7C, 7D, and 7E are schematic illustrations of a blood-pump catheter for placing within a subject's vena cava, an upstream impeller being disposed upon the catheter, distally to a downstream impeller, the upstream and downstream impellers being disposed within a support cage that supports the walls of a portion of the vena cava between the upstream and downstream impellers, in accordance with some applications of the present invention.
Figure 7B:
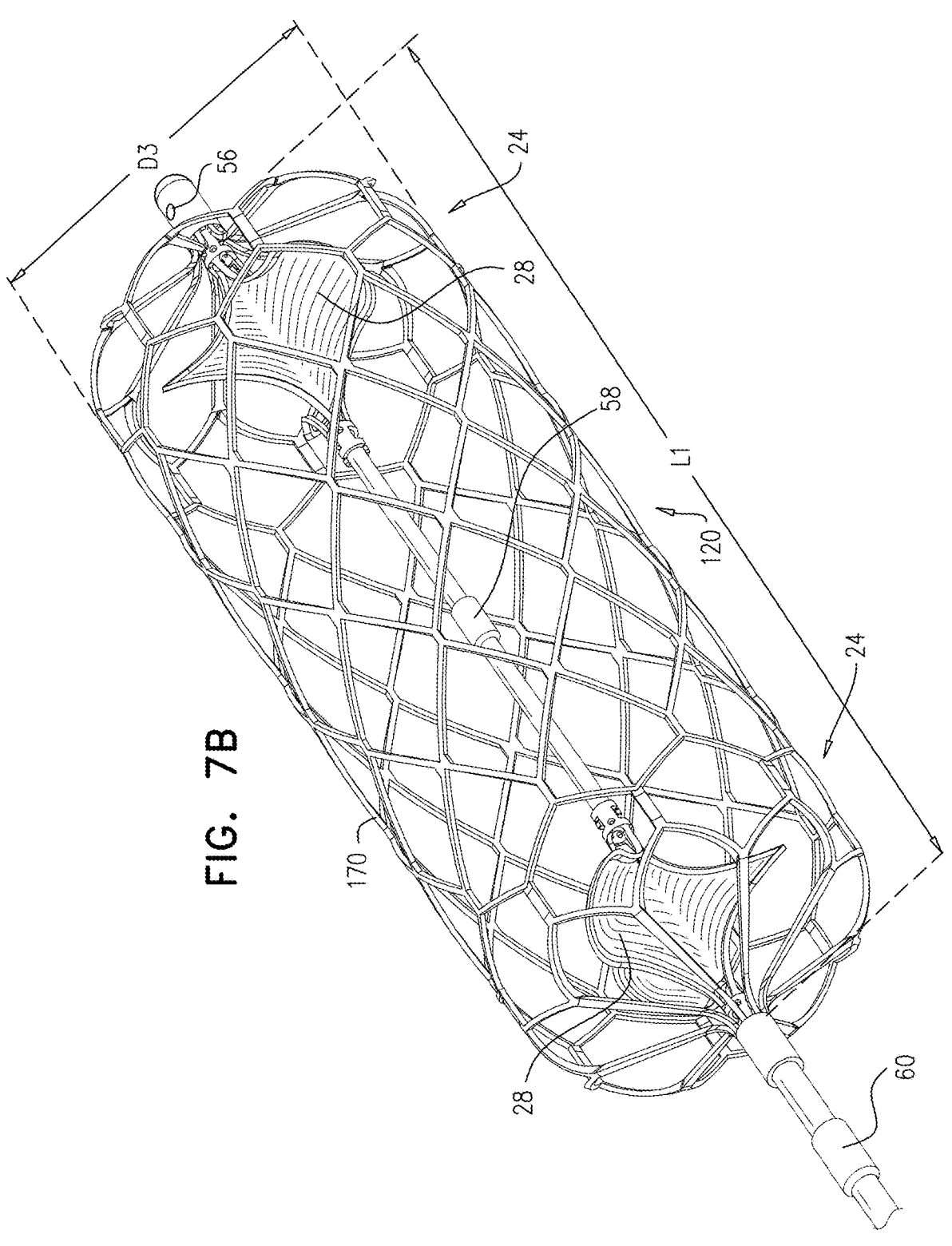
Figure 7C:
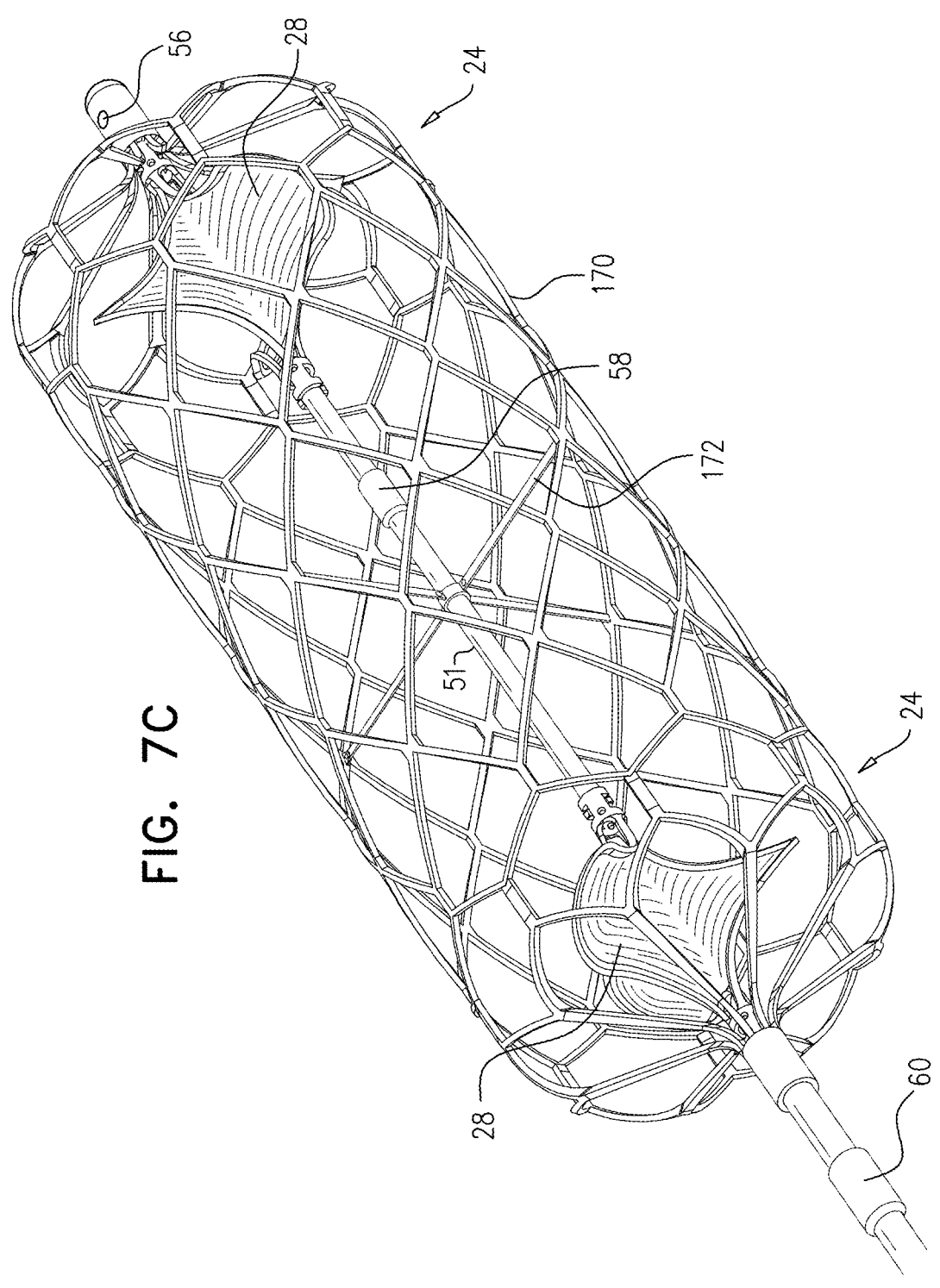

For some applications, as shown in FIGS. 7A-C, the impellers are placed inside support cage 170, in the absence of individual cages that are disposed around the respective impellers. For such applications, the support cage is typically configured to (a) support the walls of the vena cava at the low-pressure region, as described hereinabove, and (b) to maintain a separation between the impellers and the inner wall of the vena cava, in a generally similar manner to that described hereinabove with respect to cage 30.

FIG. 7A shows a blood-pump catheter as described, placed inside the subject's vena cava 22. FIG. 7B shows a three-dimensional view of impellers and support cage 170 as described, in the absence of the subject's anatomy. FIG. 7C shows a three-dimensional view of impellers and support cage 170, in the absence of the subject's anatomy, and with the support cage including support elements 172, in accordance with some applications of the present invention. As described hereinabove, for some applications, an axial shaft 51 is disposed between the proximal and distal impellers and is configured to impart rotational motion from the proximal impeller to the distal impeller. For some applications, support elements 172 extend from the support cage, and are coupled to axial shaft 51, such as to maintain the disposition of shaft 51 along the longitudinal axis of the support cage. In this manner, the disposition of the axial shaft is typically maintained along the longitudinal axis of the vena cava. Further typically, the support elements maintain the longitudinal axes of the proximal and distal impellers in alignment with one another, and in alignment with the longitudinal axis of the vena cava.

Figure 7D:
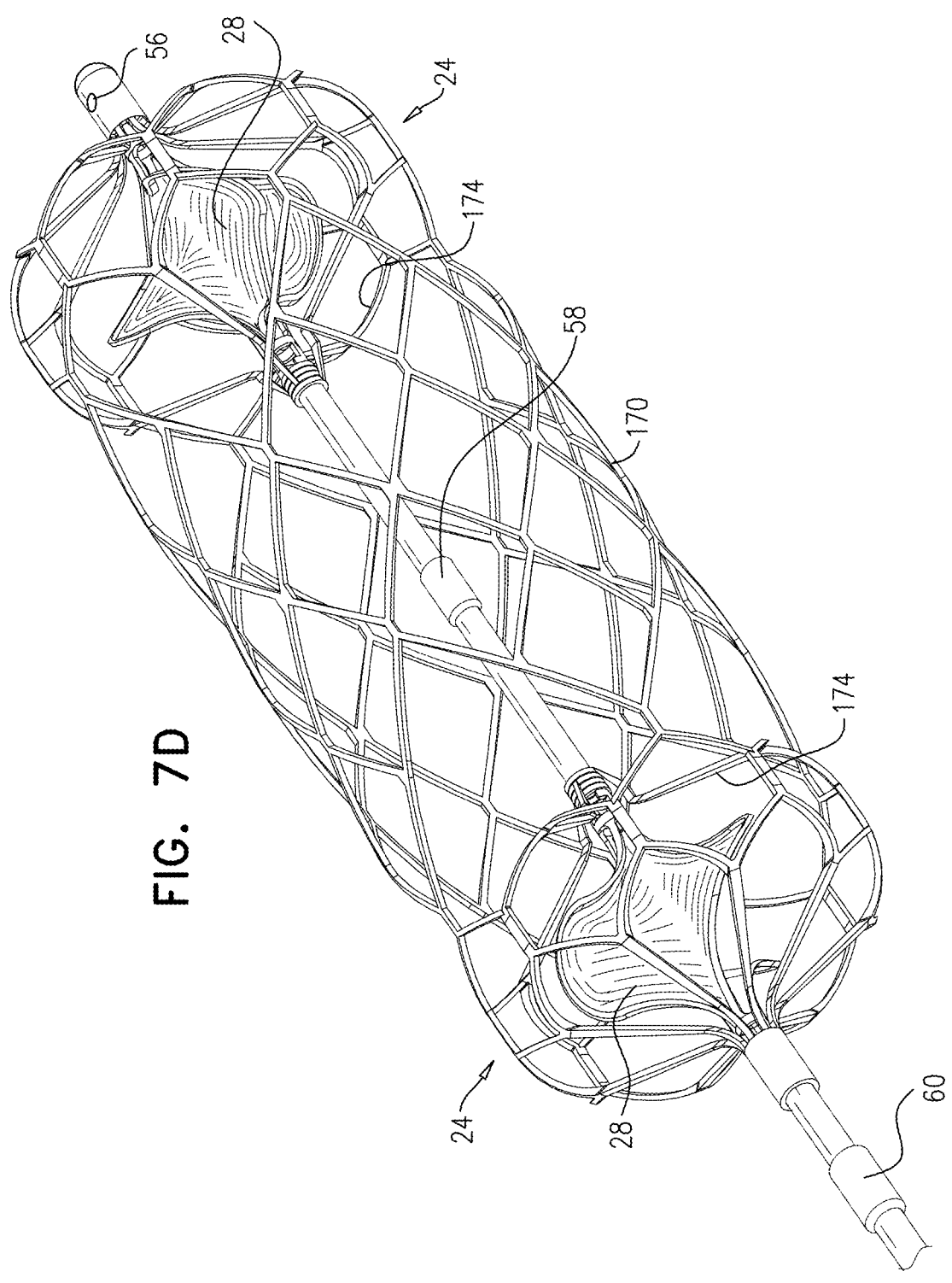
Figure 7E:
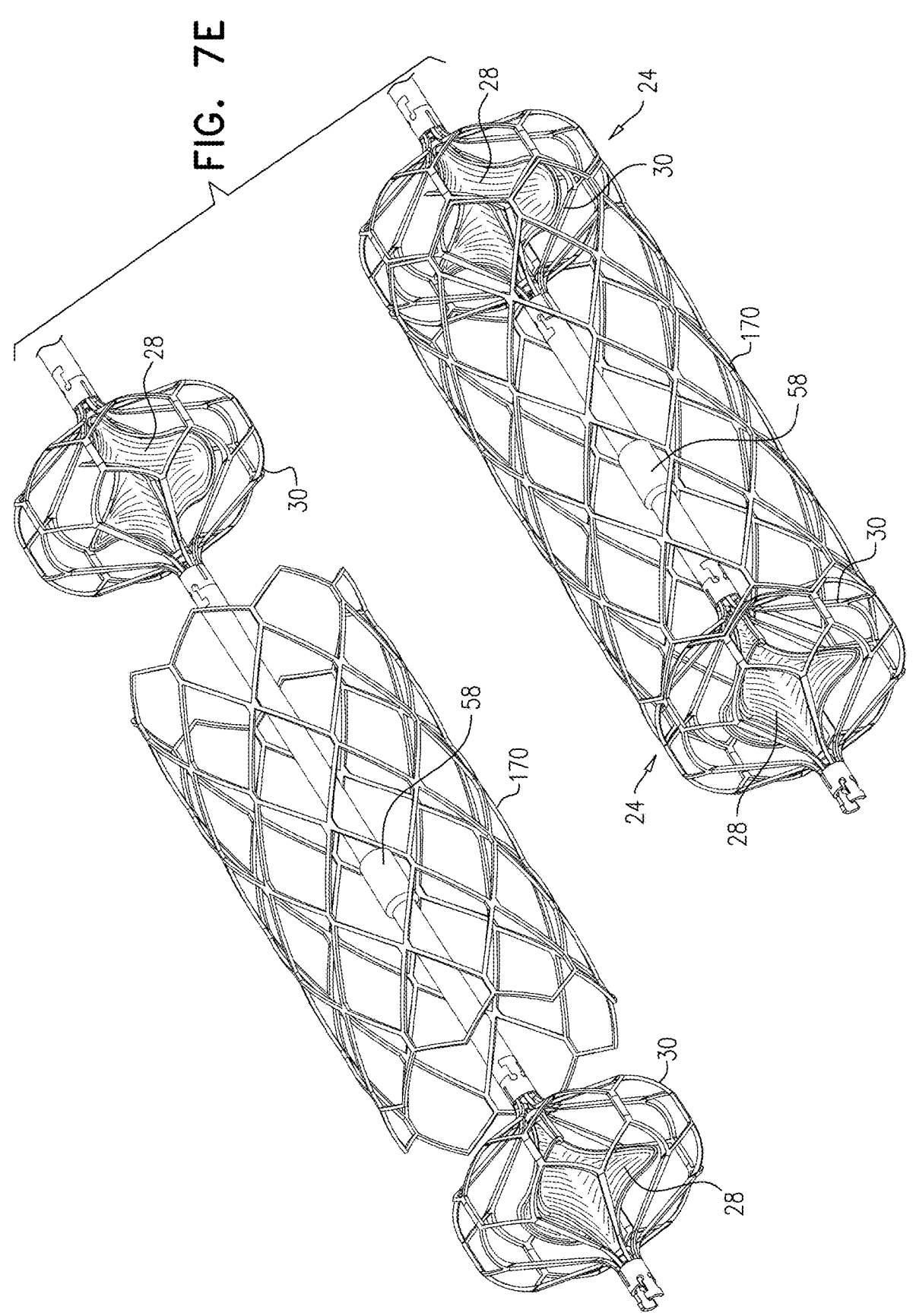

For some applications, as shown in FIGS. 7D-E, impellers 28D and 28U are placed inside support cage 170, in the presence of individual cages that are disposed around the respective impellers. Typically, the individual cages in which the impellers are disposed are generally similar to impeller cage 30, as described hereinabove.

For some applications, support cage 170 is shaped to define individual impeller cages 174, one or more of which are formed as a single integrated structure together with the support cage, as shown in FIG. 7D. For example, one or more of the individual impeller cages and the support cage may be cut from a single piece of a shape memory metal or alloy (e.g., nitinol) using techniques as described hereinbelow with reference to FIGS. 11A-C.

Alternatively, individual impeller cages 30 may be formed separately from support cage 170, as shown in FIG. 7E. For such applications, the impellers may be placed inside individual impeller cages 30, as described hereinabove, and individual impeller cages 30 may then be placed inside support cage 170. For some such applications, individual impeller cages 30 are placed inside support cage 170 inside the subject's body (e.g., inside the subject's vena cava). Alternatively, individual impeller cages 30 are placed inside support cage 170 outside the subject's body (e.g., within guide catheter 23, shown in FIG. 1A), and the individual impeller cages are deployed inside the subject's body (e.g., inside the subject's vena cava) together with the support cage.

In general, FIGS. 6 and FIGS. 7A-E show examples of blood-pump catheter 20 in which the blood-pump catheter includes a support structure (e.g., stent 160, or support cage 170), a longitudinal center of the support structure being disposed between the upstream and downstream blood pumps (e.g., between the upstream and downstream impellers). For some applications, the longitudinal center of the support structure is disposed equidistantly from the upstream and downstream blood pumps (e.g., the upstream and downstream impellers). The support structure is configured to support an inner wall of the vena cava in an open configuration during the pumping of the blood by the first and second pumps. For some applications (not shown), a support structure, such as the structure shown in FIGS. 6, 7A-E, and/or as described hereinbelow with reference to FIGS. 9A-B, 10A-D, and/or 11A-C, is used in conjunction with a blood-pump catheter that includes a downstream pump and an upstream occlusion element (e.g., as shown in FIGS. 5A-B), mutatis mutandis. For such applications, the support structure is configured to support an inner wall of the vena cava in an open configuration during the pumping of the blood by the downstream pump.

Figure 8A:
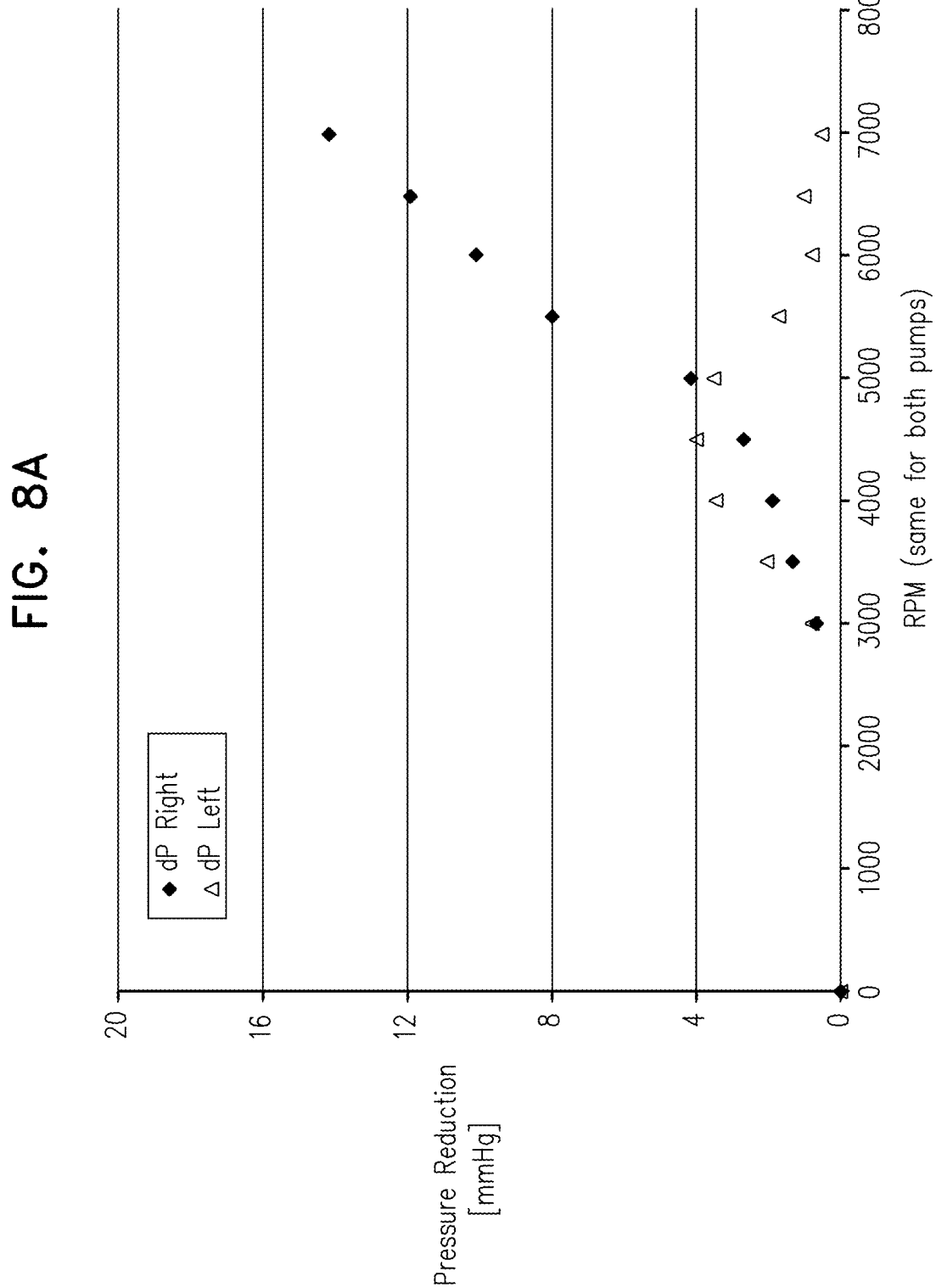
FIGS. 8A, 8B, and 8C are graphs showing the pressure drop recorded in models of a subject's left and right renal veins, during experiments that were conducted using blood pumps, in accordance with some applications of the present invention.
Figure 8B:
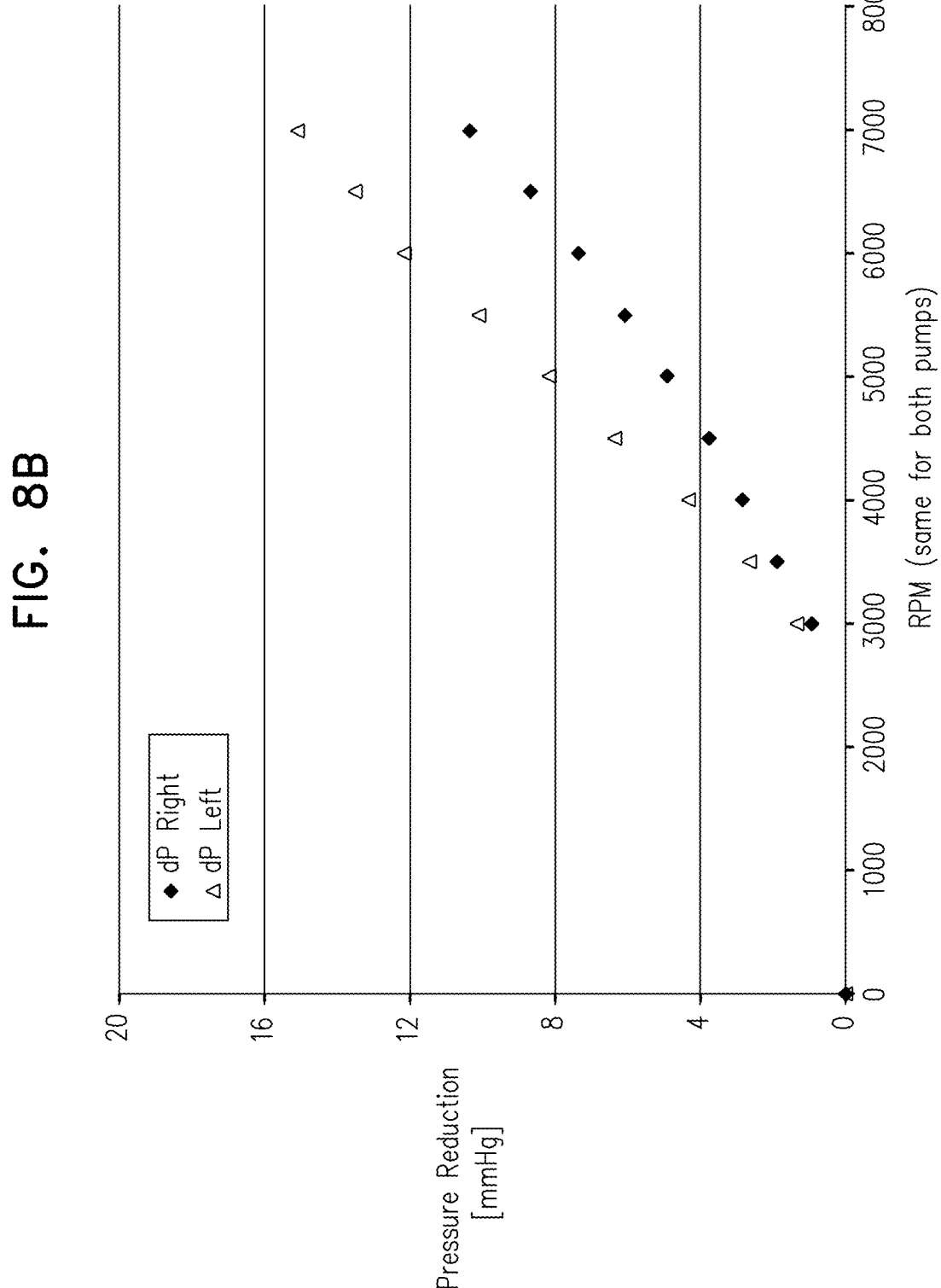
Figure 8C:
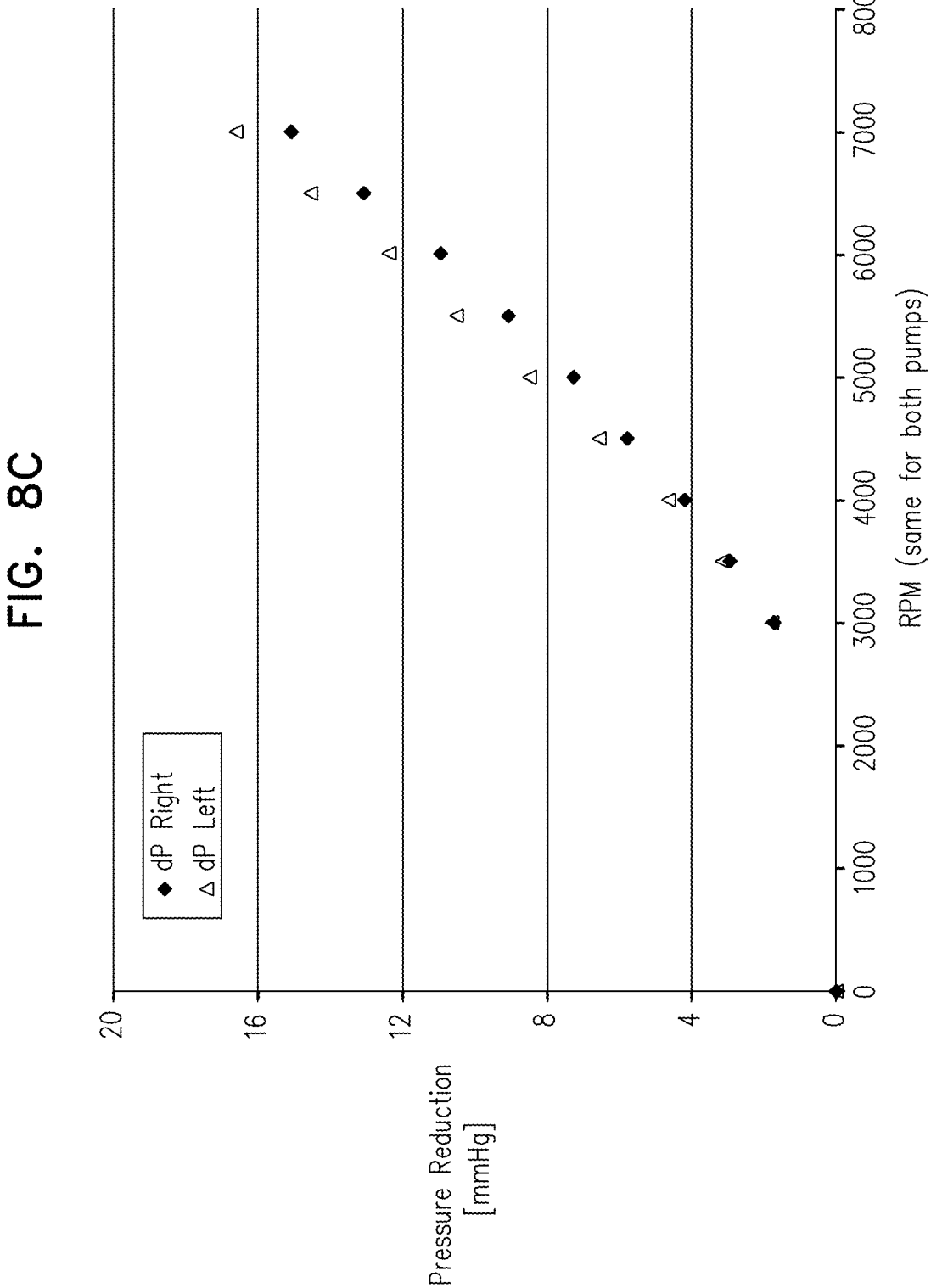

Reference is now made to FIGS. 8A, 8B, and 8C, which are graphs showing the pressure drop recorded in models of a subject's left and right renal veins, during experiments that were conducted using pumps, in accordance with some applications of the present invention.

In the experiments, a model of the vena cava and renal veins was used. The model was made of flexible silicone filled with saline. Upstream and downstream pumps as described herein were placed inside the vena cava, respectively below and above the renal veins. The pumps were activated to pump the saline through the vena cava in the manner described herein, and the drop in pressure in left and right renal veins was measured relative to the pressure in the left and right renal veins before the pumps were activated.

FIG. 8A shows a plot of the measured pressure reduction (dP) in the left and right renal veins for respective rates of revolutions per minute (RPM) of the pumps (which was always the same for both pumps), for when the pumps were placed in the vena cava in the absence of either a support stent (as shown in FIG. 6) or a support cage or sleeve (as shown in FIGS. 7A-E, 9A-B, 10A-D, and/or 11A-C) between the upstream and downstream pumps.

FIG. 8B shows a plot of the measured pressure reduction (dP) in the left and right renal veins for respective rates of revolutions per minute (RPM) of the pumps (which was always the same for both pumps), for when the pumps were placed in the vena cava in the presence of a support stent (as shown in FIG. 6) between the upstream and downstream pumps.

FIG. 8C shows a plot of the measured pressure reduction (dP) in the left and right renal veins for respective rates of revolutions per minute (RPM) of the pumps (which was always the same for both pumps), for when the pumps were placed in the vena cava in the presence of a support cage between the upstream and downstream pumps, the support cage being configured as shown in FIG. 7E.

As may be observed in FIGS. 8A-C, the greatest pressure reduction was achieved when the pumps were used in conjunction with a support cage that extends at least from the longitudinal center of the downstream impeller to the longitudinal center of the upstream impeller (the results of which are shown in FIG. 8C). In addition, the most even pressure reduction of both the left and right renal veins was achieved when the pumps were used in conjunction with a support cage that extends at least from the longitudinal center of the downstream impeller to the longitudinal center of the upstream impeller. When a support stent as shown in FIG. 6 was disposed between the upstream and downstream pumps (the result of which are shown in FIG. 8B), there was still a greater and more even pressure reduction than when the upstream and downstream pumps were used in the absence of any supporting structure between the upstream and downstream pumps (the results of which are shown in FIG. 8A).

Therefore, the results shown in FIGS. 8A-C indicate that the efficacy of the reducing renal venous pressure by pumping blood through the vena cava using upstream and downstream pumps as described herein may be improved by placing a support structure inside the vena cava between the upstream and downstream pumps, in accordance with techniques described herein. Furthermore, the results indicate that the efficacy of the aforementioned technique may be improved by placing a support cage inside the vena cava that extends at least from the longitudinal center of the downstream pump (e.g., the longitudinal center of the impeller of the downstream pump) to the longitudinal center of the upstream pump (e.g., longitudinal center of the impeller of the upstream pump). Therefore, for some applications of the present invention, apparatus and methods as described in FIGS. 6, 7A-E, 9A-B, 10A-D, and/or 11A-C are used.

Reference is now made to FIGS. 9A-B, which are schematic illustrations of blood-pump catheter 20 for placing within a subject's vena cava 22, an upstream impeller 28U being disposed upon the catheter, proximally to a downstream impeller 28D, the upstream and downstream impellers being disposed within a support cage 180 that supports the walls of a portion of the vena cava between the upstream and downstream impellers, in accordance with some applications of the present invention. Support cage 180 is typically generally similar to support cage 170 described hereinabove, except for the differences described hereinbelow.

For some applications, impellers 28 are disposed inside respective impeller cages 30, and the impeller cages are not sized such as to hold open the inner wall of the vena cava under normal conditions, the diameter of the cages being less than that of the vena cava, as shown in FIGS. 9A-B. Even in such cases, impeller cage 30 typically functions to separate the inner wall of the vena cava from the impeller, such that the vena cava does not become injured by the impeller, for example in case intra-abdominal pressure is exerted upon the vena cava, such that the vena cava collapses against the impeller cages. Typically, for such applications, the stiffness of cage 30 is sufficiently great that pressure exerted upon the cage by the inner wall of the vena cava does not deform the cage. The cage thereby protects the impeller from being deformed by pressure from the inner wall of the vena cava.

Typically, support cage 180 is configured to extend longitudinally along more than 50 percent of a region between the first and second impellers, the support cage being configured to thereby support the inner wall of the vena cava in an open configuration in the region between the first and second impellers, e.g., as described hereinabove with reference to support cage 170. For some applications, support cage extends at least from the longitudinal center of the downstream impeller to the longitudinal center of the upstream impeller. For some applications, the support cage extends from the upstream end of the upstream impeller cage to the downstream end of the downstream impeller cage.

Typically, the dimensions of support cage 180 are generally similar to those described hereinabove with reference to support cage 170. Further typically, the maximum diameter of the support cage (i.e., the diameter of the support cage at the longitudinal location(s) at which the diameter of the support cage is at its maximum) when the support cage is in a non-constrained configuration thereof is at least 1.1 times (and, for some applications, at least 1.3 times) greater than maximum diameters of each of the impeller cages 30 (i.e., the diameters of each of the impeller cages at the longitudinal location(s) at which the diameter of each of the impeller cages is at its maximum) when the impeller cages are in non-constrained configurations thereof. For some applications, the maximum diameter of the support cage is approximately 30 mm (e.g., 30 mm plus/minus 3 mm), and the maximum diameter of each of the impeller cages is approximately 20 mm (e.g., 20 mm plus/minus 3 mm).

Typically, for applications as shown in FIGS. 9A-B, the stiffness of each of the impeller cages is at least 1.5 times greater than the stiffness of the support cage. As described hereinabove, the impeller cages are shape set such that the diameters of the impeller cages are less than that of the vena cava. Therefore, the cages are configured to be of sufficient stiffness not to be deformed by pressure from the vena cava walls. By contrast, the support cage is typically shape set such that the diameter of the support cage is greater than the diameter of the vena cava, at least in some subjects. Therefore, the support cage is typically configured to have a stiffness that is such that the support cage is at least partially narrowed by the vena cava in the event that the diameter of the support cage, in its non-constrained configuration, is greater than the diameter of the vena cava. It is noted that, even in such applications, the stiffness of the impeller cage is configured to permit the impeller cage to be inserted into the subject's vena cava by being crimped inside guide catheter 23, and to permit the impeller cage to navigate turns while being advanced through the guide catheter.

Figures 10A, 10B:
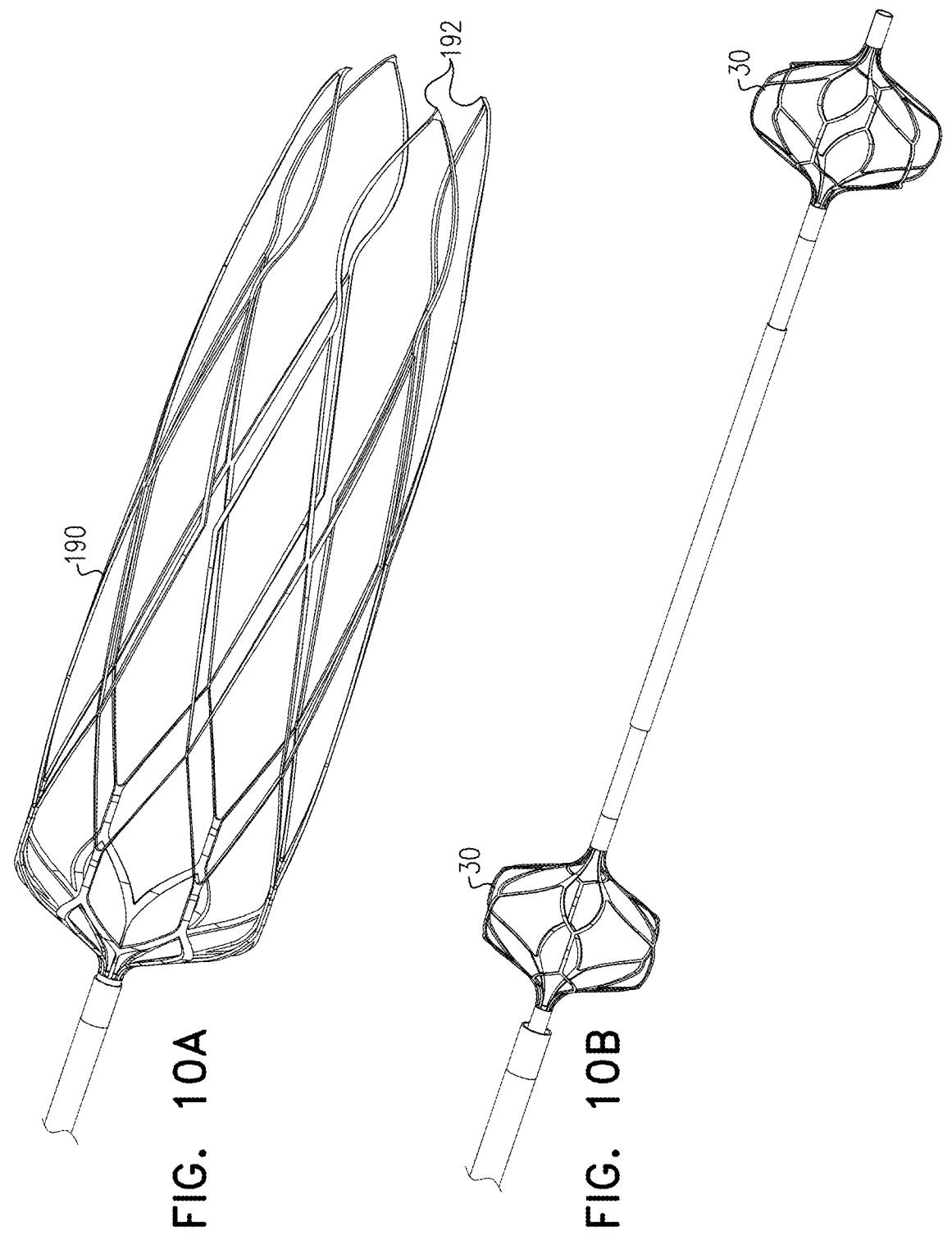
FIGS. 10A, 10B, 10C, and 10D are schematic illustrations of a support sleeve having an open distal end, and/or impeller cages for use therewith, in accordance with some applications of the present invention.
Figures 10C, 10D:
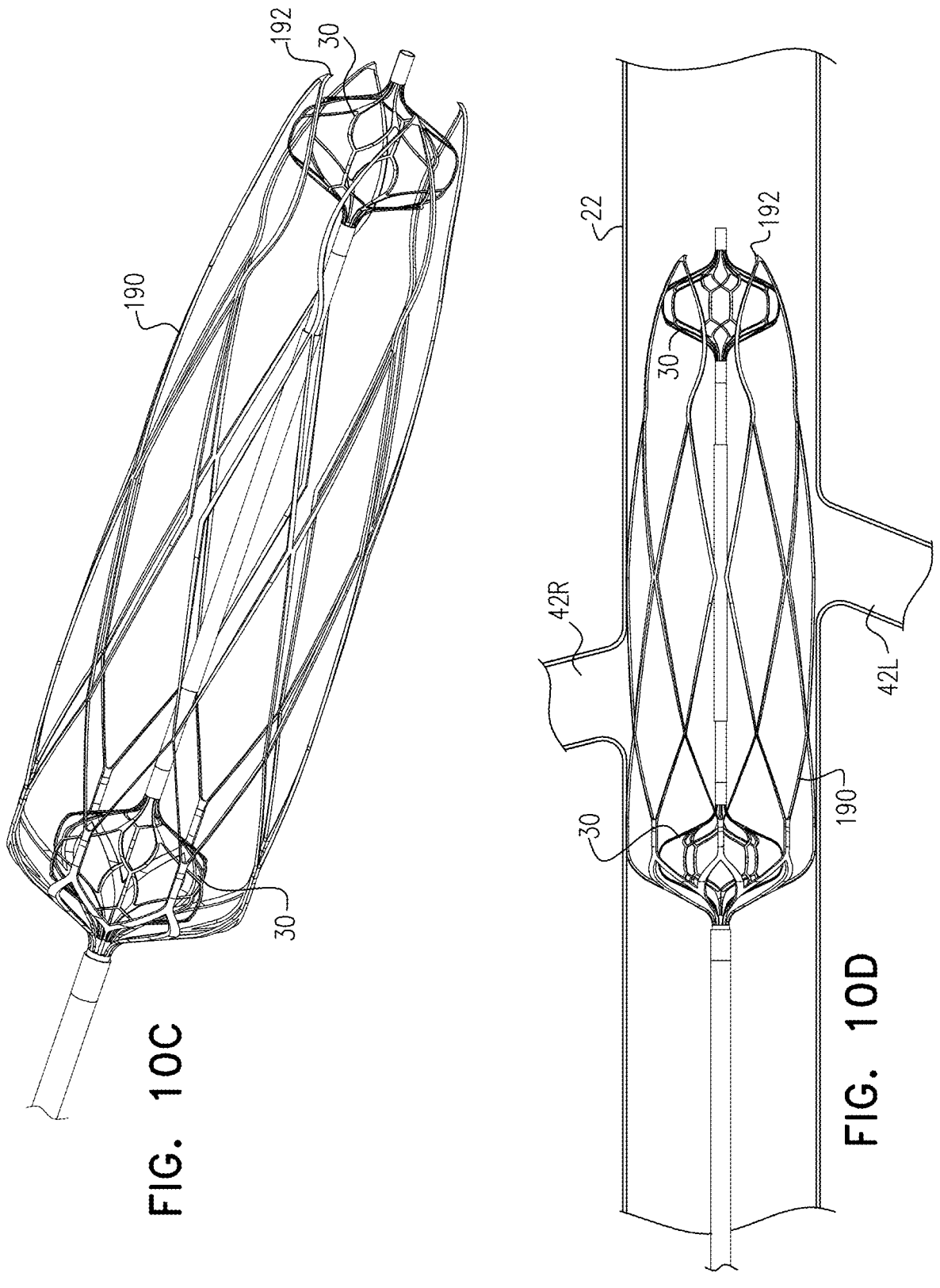

Reference is now made to FIGS. 10A, 10B, 10C, and 10D, which are schematic illustrations of a support sleeve 190 having an open end 192, and impeller cages 30 for use therewith, in accordance with some applications of the present invention. Support sleeve 190 is typically generally similar to support cage 170 described hereinabove, except for the differences described hereinbelow. Support sleeve 190 (shown in FIG. 10A) is typically used with upstream and downstream impellers 28 and impeller cages 30 (shown in FIG. 10B), which are generally as described herein. FIG. 10C shows the impeller cages disposed inside support sleeve 190, and FIG. 10D shows the impeller cages disposed inside the support sleeve within vena cava 22. Typically, by virtue of having open end 192, one of the impeller cages and the corresponding impeller are able to pass through the open end of the support sleeve even when the impeller cage and corresponding impeller are in radially non-constrained configurations thereof. Further typically, the open end of the support sleeve is not fixedly coupled to the impeller cage and/or the impeller that is disposed toward the open end of the support sleeve.

Typically, support sleeve 190 is configured to be disposed around a first one of the impeller cages and to extend longitudinally along more than 50 percent of the region between the first and second impellers, the support sleeve being configured to thereby support the inner wall of the vena cava in an open configuration in the region between the first and second impellers, e.g., as described hereinabove with reference to support cage 170. For some applications, the support sleeve extends at least from the longitudinal center of the downstream impeller to the longitudinal center of the upstream impeller. For some applications, the support sleeve extends from the upstream end of the upstream impeller cage to the downstream end of the downstream impeller cage, e.g., as shown in FIGS. 10C and 10D.

For some applications, support sleeve 190 is released into the subject's vena cava prior to impellers 28 and impeller cages 30 being released into the vena cava. Subsequent to the support sleeve being released and radially expanding inside the vena cava, impellers 28 and impeller cages 30 are released into the vena cava. For some applications, support sleeve 190 is crimped inside guide catheter 23 without the impellers and the impeller cages disposed inside the support sleeve. Alternatively, the impellers and impeller cages are disposed inside the support sleeve when the support sleeve is crimped inside the guide catheter during insertion. As described hereinabove, the open end of the support sleeve is not fixedly coupled to the impeller cage or to the impeller that are disposed toward the open end of the support sleeve. The open end of the support sleeve is thereby able to move longitudinally with respect to the impeller cage and the impeller that are disposed toward the open end of the support sleeve, thereby allowing the support sleeve to become more longitudinally extended (e.g., during crimping) than if the end of the support sleeve were to be fixedly coupled to the impeller and/or to the impeller cage that are disposed toward the open end of the support sleeve.

Figure 11A:
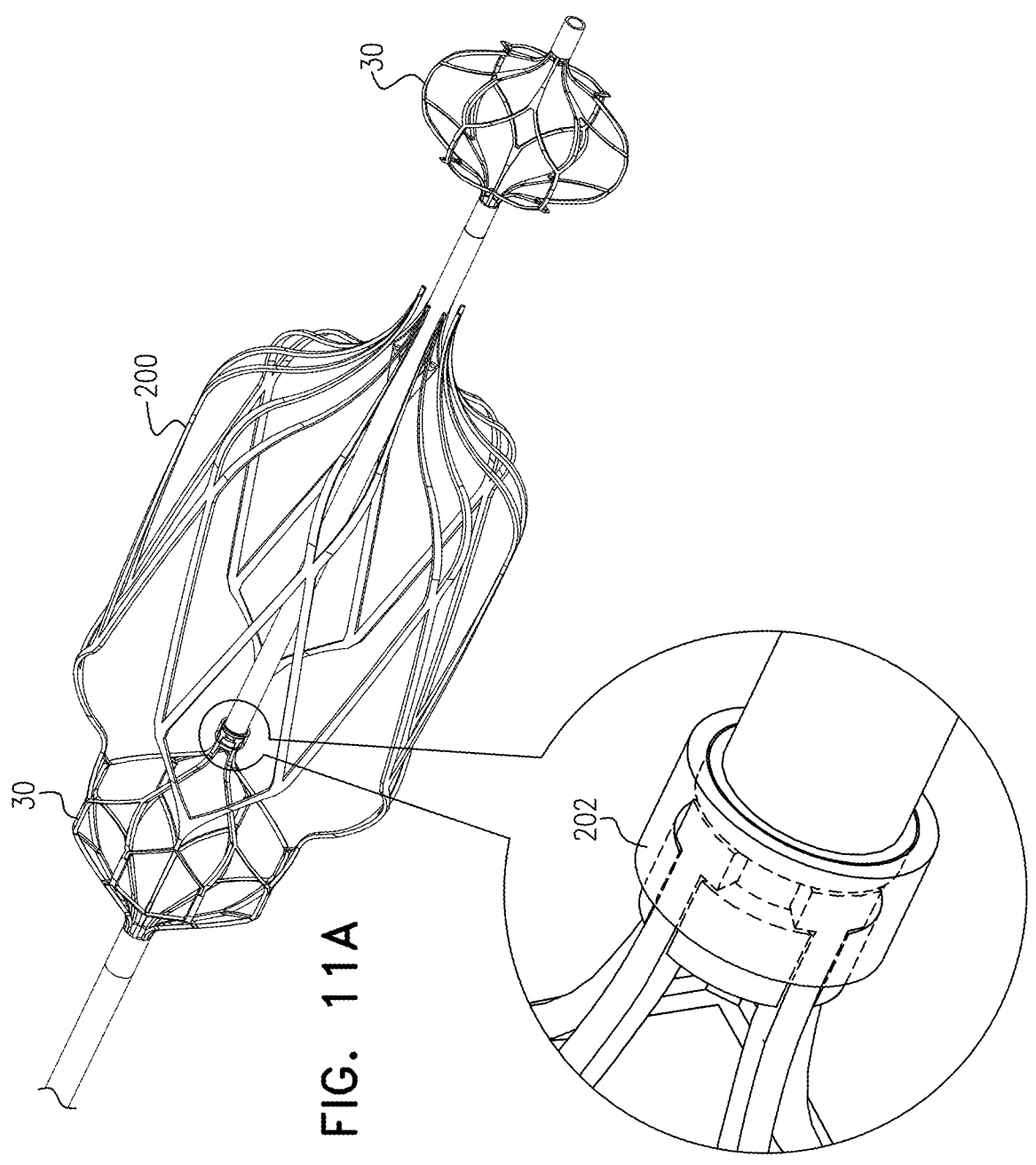
FIGS. 11A, 11B, and 11C are schematic illustrations of an impeller cage and a support sleeve that are formed from a single tube of a shape-memory allow (such as nitinol), and a cage assembly element configured to hold closed one of the ends of the impeller cage, in accordance with some applications of the present invention.
Figure 11B:
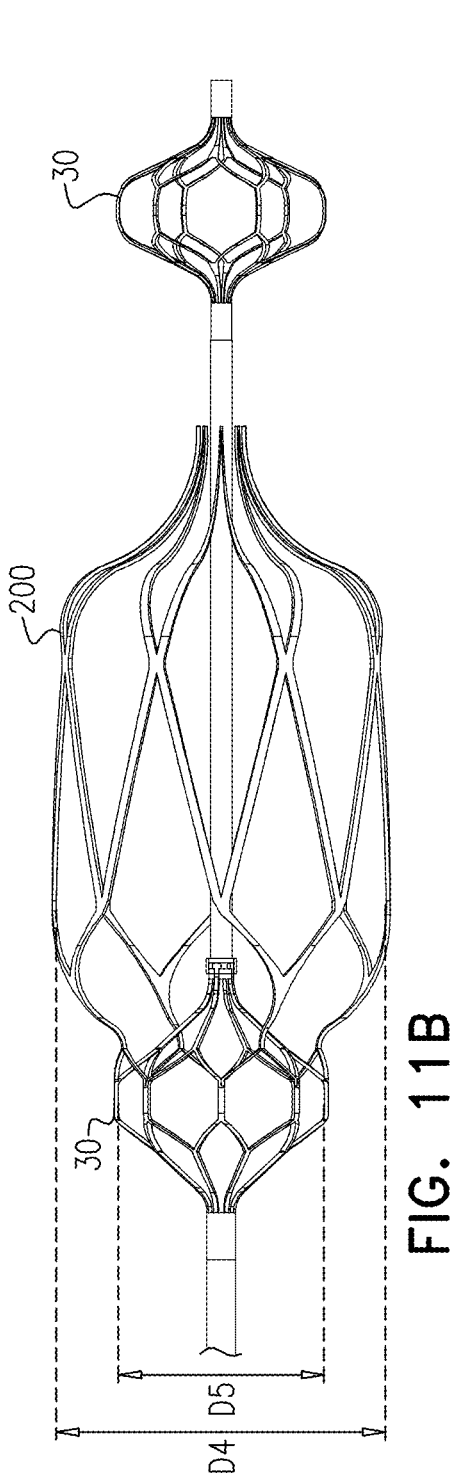
Figure 11C:
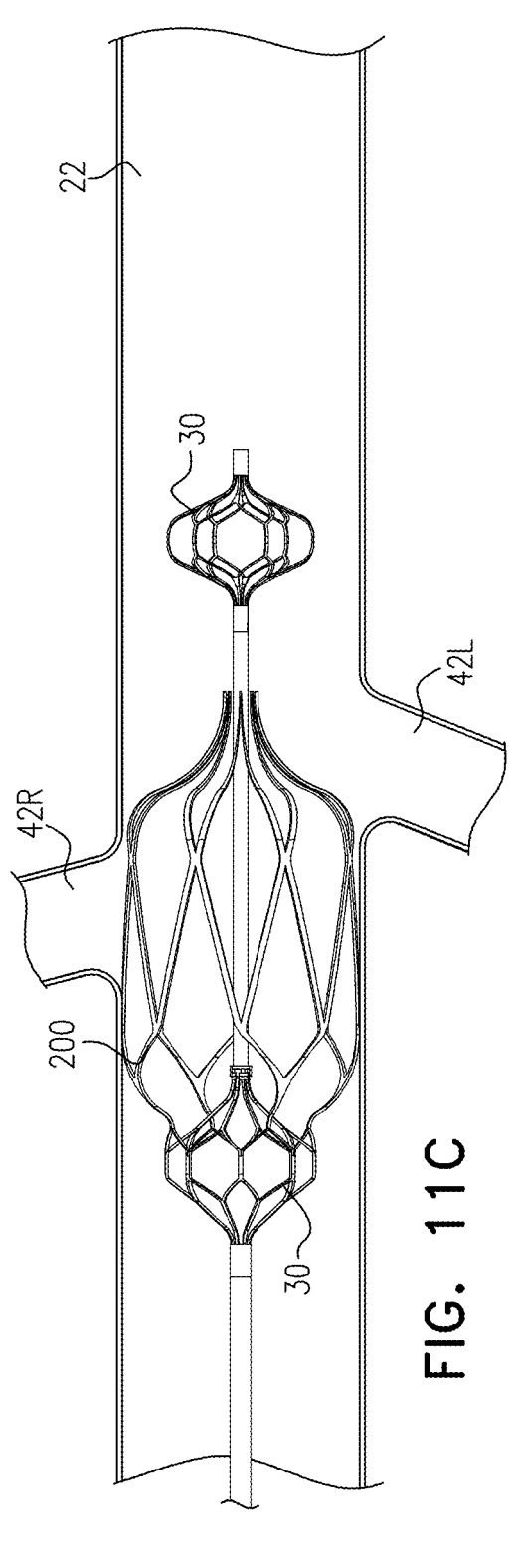

Reference is now made to FIGS. 11A, 11B, and 11C, which are schematic illustrations of an impeller cage 30 and a support sleeve 200 that are formed from a single tube of a shape-memory alloy (such as nitinol), and a cage assembly element 202 configured to hold closed one of the ends of the impeller cage, in accordance with some applications of the present invention. Support sleeve 200 is typically generally similar to support cage 170 described hereinabove, except for the differences described hereinbelow.

For some applications, an impeller cage 30 and support sleeve 200 are formed from a single tube of a shape-memory metal or alloy (such as nitinol), by cutting both the impeller cage and the support sleeve to have one open end. Subsequent to cutting the tube, the open end of the impeller cage is closed using a cage assembly element 202, which may, for example be a ring-shaped fastening element, as shown, and/or a clip, a suture, a tie, adhesive, etc.

For some applications, as described with reference to FIGS. 9A-B, the maximum diameter D4 (FIG. 11B) of the support sleeve (i.e., the diameter of the support sleeve at the longitudinal location(s) at which the diameter of the support sleeve is at its maximum) when the support sleeve is in a non-constrained configuration thereof is at least 1.1 times (and, for some applications, at least 1.3 times) greater than a maximum diameter D5 (FIG. 11B) of each of the impeller cages 30 (i.e., the diameters of each of the impeller cages at the longitudinal location(s) at which the diameter of each of the impeller cages is at its maximum) when the impeller cages are in non-constrained configurations thereof. For some applications, the maximum diameter of the support sleeve is approximately 30 mm (e.g., 30 mm plus/minus 3 mm), and the maximum diameter of each of the impeller cages is approximately 20 mm (e.g., 20 mm plus/minus 3 mm).

For some applications, at one end of support sleeve 200, one of the impellers is fixedly coupled to the support sleeve, by virtue of the impeller and the support sleeve having been formed from a single tube of shape-memory alloy, as described hereinabove. For some applications, at the other end of the support sleeve, the support sleeve is open, and the open end of the support sleeve is not fixedly coupled to the impeller cage or to the impeller that are disposed toward the open end of the support sleeve. Typically, by virtue of having an open end, the impeller cage and the impeller that are disposed toward the open end of the support sleeve are able to pass through the end of the support sleeve even when the impeller cage and the impeller are in radially non-constrained configurations thereof. For some applications, the impeller and impeller cage that are disposed toward the open end of the support sleeve are disposed inside the support sleeve when the support sleeve is crimped inside the guide catheter. As described hereinabove, the open end of the support sleeve is typically not fixedly coupled to the impeller cage or to the impeller that are disposed toward the open end of the support sleeve. The open end of the support sleeve is thereby able to move longitudinally with respect to the impeller cage and the impeller that are disposed toward the open end of the support sleeve, thereby allowing the support sleeve to become more longitudinally extended (e.g., during crimping) than if the end of the support sleeve were to be fixedly coupled to the impeller and/or to the impeller cage that are disposed toward the open end of the support sleeve.

Typically, support sleeve 200 is configured to extend longitudinally from the first impeller and impeller cage along more than 50 percent of the region between the first and second impellers, the support sleeve being configured to thereby support the inner wall of the vena cava in an open configuration in the region between the first and second impellers, e.g., as described hereinabove with reference to support cage 170. For some applications, the support sleeve extends at least from the longitudinal center of the downstream impeller to the longitudinal center of the upstream impeller. For some applications, the support sleeve is configured, such that when the support sleeve radially expands inside the vena cava, the support sleeve does not extend longitudinally to the second impeller cage, e.g., as shown in FIG. 11C.

It is noted that blood pumps 24U and 24D, the catheters upon which the blood pumps are disposed (e.g., blood-pump catheter 20, catheter 66, and catheter 68), and the occlusion elements described with reference to FIGS. 5A-B, and other devices described herein, are generally described as being placed within the subject's vena cava, such that the upstream pump or the occlusion element is disposed upstream of junctions of the vena cava with the subject's renal veins, and the downstream pump is disposed downstream of the junctions of the vena cava with the subject's renal veins. However, it is noted that the scope of the present invention includes placing upstream pump 24U or the occlusion element in any main vein upstream of a tributary venous system, and placing downstream pump 24D downstream of said tributary venous system, and configuring the pump(s) (e.g., via the direction of rotation of impellers of the pumps, or the orientation of the pumps) to generate preferential flow from the tributaries into the main vein, mutatis mutandis. For example, the pump(s) could be used to generate flow from the subject's hepatic veins into the subject's vena cava, in order to increase perfusion of the subject's liver, mutatis mutandis. For some applications, the upstream pump or the occlusion element is placed within a main vein upstream of two or more tributary venous systems into the main vein (e.g., within the vena cava upstream of the renal venous system and the hepatic venous system). The downstream pump is placed downstream of the two or more tributary venous systems. The pump(s) are configured to generate preferential flow from both of the tributary venous systems into the main vein by pumping blood through the main vein, in the manner described herein. For some applications, upstream and downstream pumps 24U and 24D and blood-pump catheter 20 are placed within the subclavian vein or jugular vein at junctions of the vein with a lymph duct and are used to increase flow of lymphatic fluid from the lymph duct into the vein, using the techniques described herein, mutatis mutandis.

For some applications, upstream pump 24U or the occlusion element is placed in a main vein upstream of a tributary venous system, and downstream pump 24D is placed downstream of said tributary venous system, and the pump(s) are configured (e.g., via the direction of rotation of impellers of the pumps, or the orientation of the pumps) to reduce flow from the tributaries into the main vein. For some such applications, the blades of the downstream impeller are oriented such that, as the downstream impeller is rotated, the downstream impeller pumps in the upstream direction (toward the junction between the tributary system and the main vein). The blades of the upstream impeller are oriented such that, as the upstream impeller is rotated, the upstream impeller pumps in the downstream direction (toward the junction between the tributary system and the main vein).

For some applications, the upstream and downstream pumps 24U and 24D, the catheter(s) upon which the blood pumps are disposed (e.g., blood-pump catheter 20, catheter 66, and catheter 68), and/or the occlusion elements described with reference to FIGS. 5A-B, and other devices described herein, are placed within a main artery upstream and downstream of bifurcations of the artery with one or more branching arterial systems that branch from the main artery and supply a given organ, mutatis mutandis. For such applications, the upstream pump is typically configured to pump in the downstream direction (toward the bifurcations) and the downstream pump is configured to pump in the upstream direction (toward the bifurcations), such that blood flow into the branching arterial system is increased, thereby increasing perfusion of the organ. Alternatively or additionally, the occlusion element is placed downstream of the bifurcations of the artery with the one or more arterial systems and is configured to partially occlude the artery downstream of the bifurcations. For example, the upstream pump may be placed in the subject's aorta upstream of the subject's renal arteries and the downstream pump may be placed in the subject's aorta downstream of the subject's renal arteries, the pumps acting to pump blood into the renal arteries and toward the subject's kidneys. For some applications, upstream and downstream pumps, and/or occlusion elements are placed on both the arterial and venous sides of the subject's body in order to increase perfusion of a given organ or set of organs, in the manner described herein.

Figure 12:
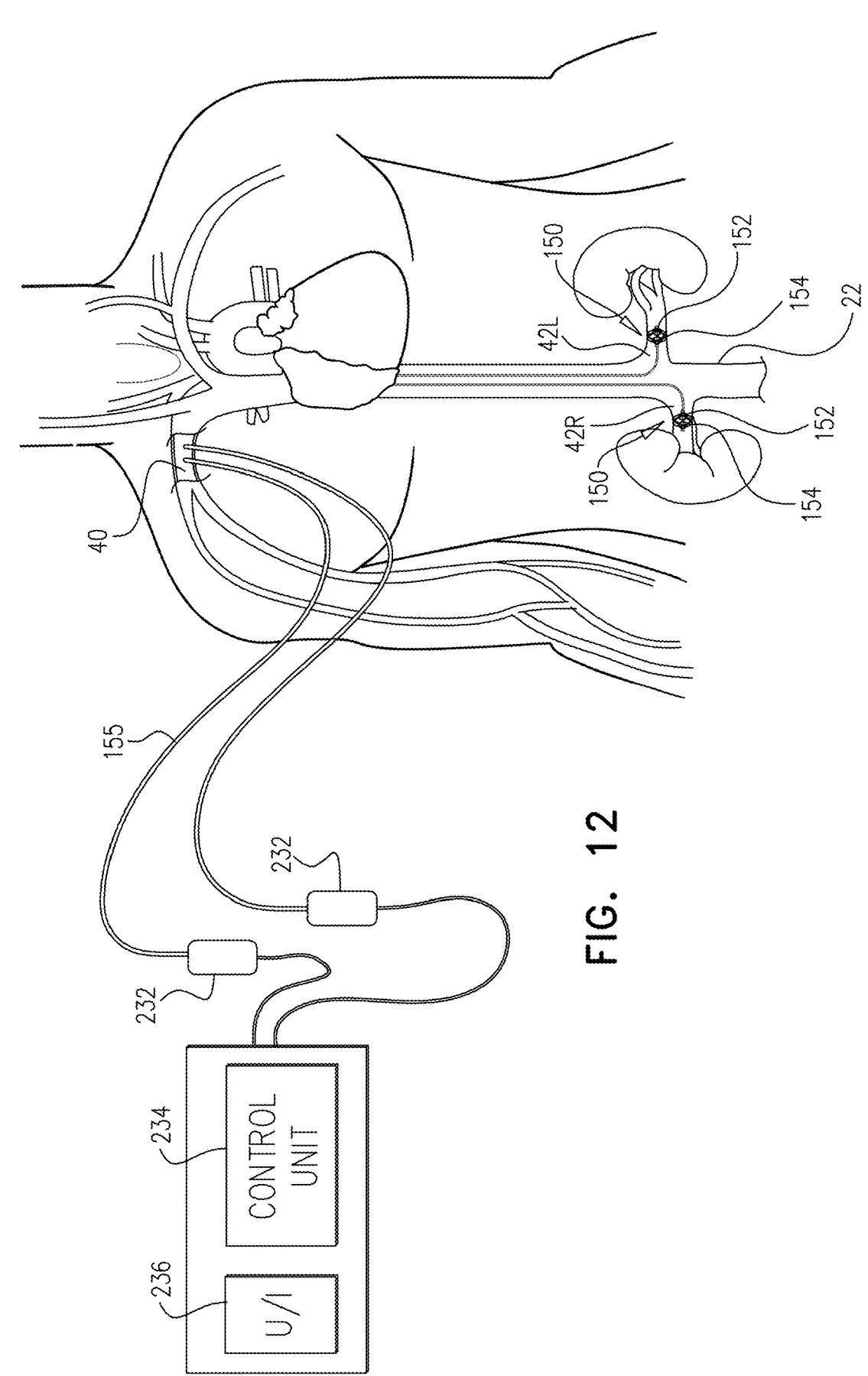
FIG. 12 is a schematic illustration of impeller-based blood pumps inserted into a subject's left and right renal veins, in accordance with some applications of the present invention.

Reference is now made to FIG. 12, which is a schematic illustration of impeller-based blood pumps 150 inserted into a subject's left and right renal veins 42 via the subject's subclavian vein 40, in accordance with some applications of the present invention. Typically, each of the blood pumps includes a radially-expandable impeller 152 disposed inside a radially-expandable impeller cage 154. Typically, the blood pumps are inserted into the left and right renal veins via respective catheters 155. Alternatively (not shown), the blood pumps are inserted via a single catheter that passes from the venous access point to the subject's vena cava. The blood pumps are inserted into the subject's renal veins, while the blood pumps are in radially constrained configurations inside the guide catheter(s), and are configured to assume substantially radially non-constrained configurations by being released from the guide catheter(s) inside the subject's renal veins. For some applications, the catheters are both inserted via subclavian vein 40, as shown. Alternatively or additionally, the catheters are inserted via a different vein, e.g., the subject's femoral vein, and/or the subject's jugular vein. For some applications, blood pumps 150 are generally similar to blood pumps described in US 2016/0022890 to Schwammenthal, which is incorporated herein by reference, apart from differences described hereinbelow.

Blood pumps 150 are typically placed inside the subject's renal veins 42, and operated therein, in order to provide acute treatment of a subject suffering from cardiac dysfunction, congestive heart failure, low renal blood flow, high renal vascular resistance, arterial hypertension, diabetes, and/or kidney dysfunction. The therapeutic effect of operating blood pumps 150 within the renal veins (a) is typically generally similar to that described hereinabove with reference to blood-pump catheter 20, mutatis mutandis, and (b) is typically generally similar to the effect of renal vein blood pumps, as described in US 2016/0022890 to Schwammenthal, which is incorporated herein by reference.

Typically, the impellers of the blood pumps 150 are coupled to motors 232, which impart rotational motion to the impellers. In accordance with respective applications, the motors are disposed outside of the subject's body (as shown) or are placed inside the subject's body (not shown). Typically, a control unit 234 and a user interface 236 are disposed outside the subject's body. Further typically, the control unit receives inputs from pressure sensors, which are disposed on upstream and downstream sides of the blood pumps. When blood pump 150 is disposed inside a renal vein (as shown in FIG. 12, for example), the pressure measured by the upstream pressure sensor is indicative of blood pressure upstream of the blood pump, inside the renal vein, and the pressure measured by a downstream pressure sensor is indicative of central venous pressure. For some applications, the control unit receives an input from an additional sensor (such as a flow sensor and/or an oxygen-saturation sensor, and/or a thermal flow sensor, e.g., as described with reference to FIGS. 22Ai-22Cii of US 2016/0022890 to Schwammenthal, which is incorporated herein by reference), and the control unit controls the speed of the rotation of the impellers responsively to an input from the additional sensor.

For some applications, control unit 234 controls rotation of impellers 152, by controlling motors 232, responsively to one or more of the above-described inputs. Typically, user interface 236 displays the subject's current renal venous pressure and central venous pressure, based upon the pressures measured by the sensors. Typically, based upon the current values of the subject's renal venous pressure and central venous pressure, a user (such as a healthcare professional) inputs a target value for the subject renal venous pressure, via the user interface. In response thereto, control unit 234 controls the speed of the rotation of the impeller, such that the impeller pumps through the renal vein and toward the vena cava at a flow rate that is such as to reduce the renal venous pressure toward the target level, as indicated by the user. For some applications, in response to a signal received from the downstream pressure sensor indicating that the central venous pressure is at the target renal venous pressure, the control unit stops the impeller rotating. In general, the control unit typically controls the speed of the rotation of the impellers responsively to inputs from the upstream and downstream pressure sensors.

It is noted that control unit 234 typically includes a computer processor that comprises circuitry and that is configured to execute the actions described herein. Typically, the operations described herein that are performed by the computer processor transform the physical state of a memory, which is a real physical article that is in communication with the computer processor, to have a different magnetic polarity, electrical charge, or the like, depending on the technology of the memory that is used.

Control unit 234 is typically a hardware device programmed with computer program instructions to produce a special-purpose computer. For example, when programmed to perform the techniques described herein, control unit 234 typically acts as a special-purpose, renal-venous-pressure-modulating computer processor.

It is further noted that user interface 236 typically includes any type of user interface configured to receive inputs from a user and/or to provide outputs to the user. For example, the user interface may include one or more input devices (such as a keyboard, a mouse, a trackball, a joystick, a touchscreen monitor, a touchpad, a voice-command interface, a smartphone, a tablet computer, and/or other types of input devices that are known in the art), and/or one or more output devices (such as a monitor, an audio output device, a smartphone, a tablet computer, and/or other types of output devices that are known in the art).

Figures 13A, 13B, 14:
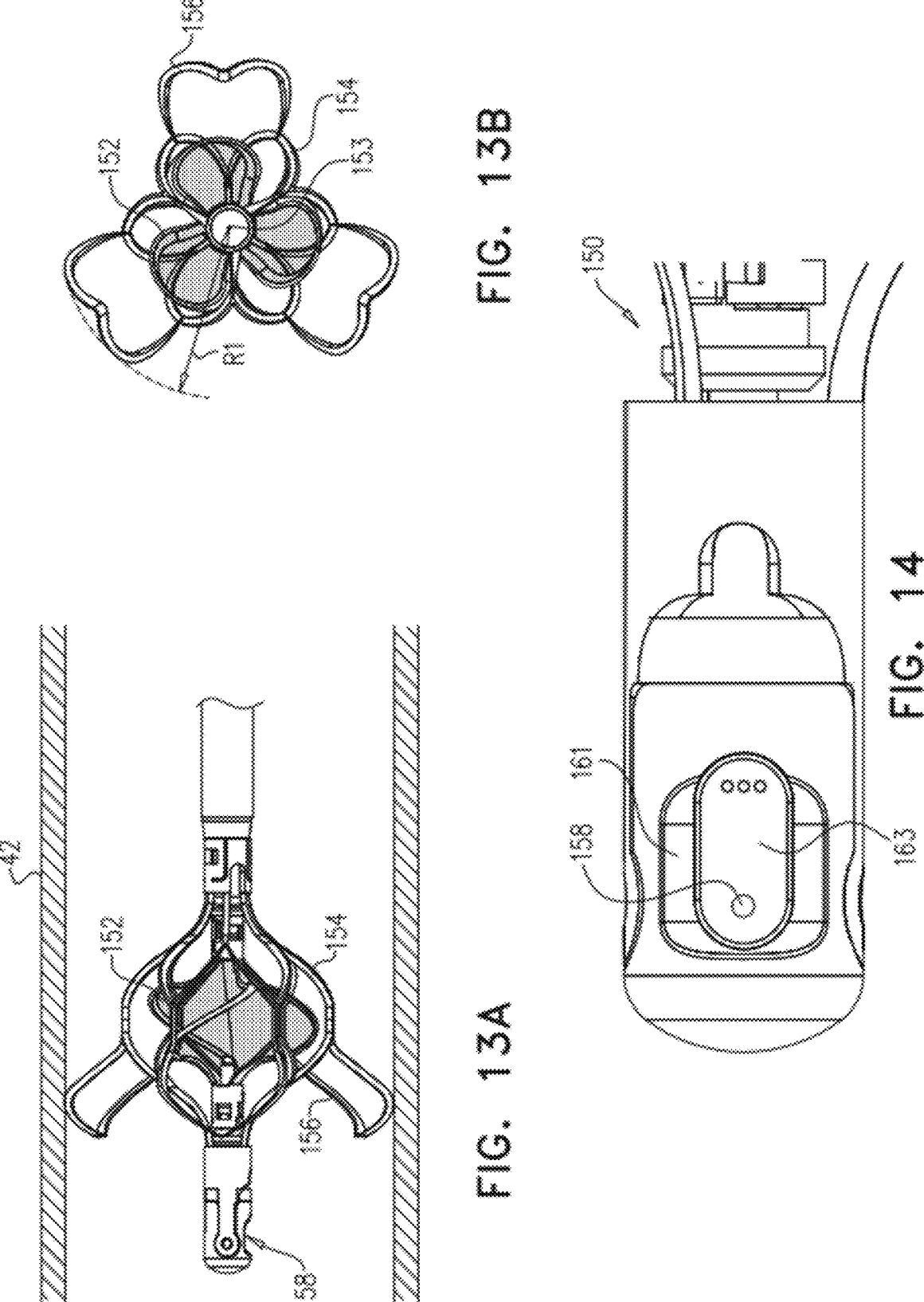
FIGS. 13A and 13B are schematic illustrations of an impeller cage that includes radially-protruding support arms that are configured to substantially align the longitudinal axis of an impeller with a local longitudinal axis of a blood vessel, in accordance with some applications of the present invention.
FIG. 14 is a schematic illustration of a pressure sensor disposed on a shaft of an impeller-based blood pump, in accordance with some applications of the present invention.

Reference is now made to FIGS. 13A-B, which are schematic illustrations of impeller cage 154, the cage including radially-protruding support arms 156 that are configured to align the longitudinal axis of impeller 152 with a local longitudinal axis of renal vein 42, in accordance with some applications of the present invention. FIG. 13A shows the impeller cage disposed inside the subject's renal vein 42. As shown, for some applications, the impeller cage is sized such that, when the cage is in a radially non-constrained configuration, the maximum diameter of the cage (i.e., the diameter of the cage at the longitudinal location at which the diameter of the cage is at its maximum) is less than the diameter of the renal vein at the location within the renal vein at which the impeller cage is deployed, at least in some subjects. Typically, diameters of renal veins vary from approximately 8 mm to approximately 16 mm, and, for example, the diameter of the impeller cage may be more than 8 mm (e.g., more than 10 mm), and/or less than 13 mm (e.g., less than 12 mm), e.g., between 8 and 13 mm, or between 10 and 12 mm. For such applications, the cage is typically configured to have a stiffness that is such that even if pressure is exerted upon the cage by walls of the renal vein, the cage does not become deformed, and the cage thereby protects the impeller from becoming deformed.

The inventors of the present application found that if impeller cages for placement within the renal veins as described herein (e.g., with reference to FIG. 12) are configured to be have diameters that are substantially greater than the diameters of some subjects' renal veins, and the impeller cages are configured to become radially compressed by the walls of the renal veins, this may result in the impeller becoming deformed (e.g., by the upstream and downstream ends of the impeller axis becoming misaligned), and/or in the impeller becoming misaligned with the local longitudinal axis of the renal veins. Therefore, as described hereinabove, for some applications, the impeller cage is configured to have a smaller diameter, such that even in cases in which the impeller cage has a greater diameter than a subject's renal vein (e.g., in the case of a subject with narrow renal veins), the radial force that is exerted upon the impeller cage by the subject's renal vein is lower. Furthermore, the impeller cage is configured to have a stiffness that is such that even if pressure is exerted upon the cage by walls of the renal vein, the cage does not become deformed, and the cage thereby protects the impeller from becoming deformed. It is noted that, even in such cases, the stiffness of the impeller cage is configured to permit the impeller cage to be inserted into the subject's renal vein by being crimped inside guide catheter 155, and to permit the impeller cage to navigate turns while being advanced through the guide catheter.

As described hereinabove, for some applications, impeller cage 154 is configured such that the maximum diameter of the cage is less than the diameter of the renal vein at the location within the renal vein at which the impeller cage is deployed. For some such applications, radially-protruding support arms 156 protrude radially from the impeller cage. The radially-protruding support arms 156 are configured, upon the blood pump being released into the subject's renal vein, to come into contact with the inner wall of the subject's renal vein by radially expanding. The radially-protruding support arms 156 are configured to thereby align the longitudinal axis of impeller 152 with a local longitudinal axis of renal vein 42, as shown in FIG. 13A. Typically, ceteris paribus, the efficacy of the pumping of blood by impeller 152 is greater, the greater than alignment of the longitudinal axis of the impeller with the local longitudinal axis of the renal vein. It is noted that, for some applications, the radially-protruding support arms may not fully align the longitudinal axis of impeller with the local longitudinal axis of renal vein. However, typically, the radially-protruding support arms maintain the longitudinal axis of the impeller in greater alignment with the local longitudinal axis of the renal vein, relative to alignment of the longitudinal axis of the impeller with the local longitudinal axis of the renal vein in the absence of the support arms, ceteris paribus.

For some applications, the radially-protruding support arms each define a radius R1 with respect to the longitudinal axis 153 of the shaft of the blood pump that is greater than 7 mm and/or less than 9 mm, e.g., 7-9 mm. Radius R1 (shown in FIG. 13B) is a measure of the maximum radial distance between the support arm and longitudinal axis 153. For some applications, rather than defining radially-protruding support arms, cage 30 defines a bulbous extension that, for example, may be generally similar in shape to bulbous extension 84 described hereinbelow with reference to FIG. 16, mutatis mutandis.

As described hereinabove, for some applications, control unit 234 (FIG. 12) receives inputs from pressure sensors that are disposed on upstream and downstream sides of the blood pumps, and controls rotation of impellers 152, by controlling motors 232, responsively to one or more of the inputs. As shown, for some applications, upstream pressure sensor 158 is disposed on the shaft of blood pump 150 distally to the impeller and the impeller cage. If the upstream pressure sensor comes into contact with the inner wall of the renal vein, then the upstream pressure sensor may measure the subject's intraabdominal pressure, which is conveyed through the wall of the renal vein, as opposed to measuring blood pressure within the renal vein. Therefore, for some applications, radially-protruding support arms 156 are configured to separate the upstream pressure sensor from the inner wall of the renal vein, by centering the shaft of the blood pump within the renal vein. For example, the radially-protruding support arms may maintain the pressure sensor at a distance of at least 2 mm from an inner wall of the renal vein.

For some applications, the impeller cage is sized such that, when the cage is in its radially non-constrained configuration, the maximum diameter of the cage is less than the diameter of the renal vein, as described hereinabove. For some such applications, even in the absence of radially-protruding support arms 156, the longitudinal axis of the impeller is maintained substantially in alignment with the local longitudinal axis of the renal vein by guide catheter 155 providing support to the impeller and the impeller cage. For example, the guide catheter may be inserted into the renal vein via the subject's femoral vein, and the catheter may be configured as described in US 2015/0157777 to Tuval, which is incorporated herein by reference. For such applications, the guide catheter is typically configured to maintain pressure sensor 158 at a distance of at least 2 mm from an inner wall of the blood vessel, as described hereinabove.

For some applications, control unit 124 is configured to account for pressure sensor 158 contacting the inner wall of the renal vein, and measuring the subject's intraabdominal pressure. For example, the control unit may run the following algorithm:

A. The Control Unit Increases the Rotation Speed of the Impeller.

If, in response to the rotation speed of the impeller increasing, the pressure reading of pressure sensor increases, the control unit (a) disregards the pressure reading from the pressure sensor, (b) generates an output indicating that the reading from pressure sensor 158 is erroneous, and/or (c) generates an indication that the reading from pressure sensor 158 is indicative of intraabdominal pressure, and not renal blood pressure. (This is because, in response to the rotation speed of the impeller increasing, renal pressure would be expected to decrease. The increase in pressure indicates that the inner wall of the renal vein has come into contact with the pressure sensor, such that the pressure sensor is measuring intraabdominal pressure.)

If, in response to the rotation speed of the impeller increasing, the pressure reading of the pressure sensor decreases, the control unit interprets the pressure reading from the pressure sensor as being indicative of renal blood pressure, and generates an output, and/or further modulates the speed of rotation of the impeller, in response thereto (e.g., in the manner described hereinabove, with reference to FIG. 12).

and/or

B. The control unit decreases the rotation speed of the impeller.

If, in response to the rotation speed of the impeller decreasing, the pressure reading of pressure sensor 158 decreases, the control unit (a) disregards the pressure reading from the pressure sensor from prior to the decrease in the rotation speed, (b) generates an output indicating that the reading from pressure sensor 158 from prior to the decrease in the rotation speed was erroneous, and/or (c) generates an indication that the reading from pressure sensor 158 from prior to the decrease in the rotation speed was indicative of intraabdominal pressure, and not renal blood pressure. (This is because, in response to the rotation speed of the impeller decreasing, renal pressure would be expected to increase. The increase in pressure indicates that the inner wall of the renal vein had been in contact with the pressure sensor, such that the pressure sensor was measuring intraabdominal pressure, but that the inner wall of the renal vein has now separated from the pressure sensor.)

If, in response to the rotation speed of the impeller decreasing, the pressure reading of pressure sensor increases, the control unit interprets the pressure reading from the pressure sensor as being and having been indicative of renal blood pressure, and generates an output, and/or further modulates the speed of rotation of the impeller, in response thereto (e.g., in the manner described hereinabove, with reference to FIG. 12).

For some applications, the above-described algorithm is run by control unit 52 (FIG. 1), in order to accurately measure blood pressure within the subject's vena cava and/or renal veins, mutatis mutandis.

Reference is now made to FIG. 14, which is a schematic illustration of pressure sensor 158 disposed on a shaft 161 of impeller-based blood pump 150, in accordance with some applications of the present invention. As shown, for some applications, the distal portion of shaft 161 defines an indentation 163 therein. Pressure sensor 158 is disposed inside the indentation. As described hereinabove, if pressure sensor 158 comes into contact with the inner wall of the renal vein, then the pressure sensor may measure the subject's intraabdominal pressure, which is conveyed through the wall of the renal vein, as opposed to measuring blood pressure within the renal vein. Therefore, for some applications, pressure sensor is disposed inside indentation 163, so as to reduce the likelihood of the pressure sensor coming into contact with the wall of the renal vein.

Figure 15:
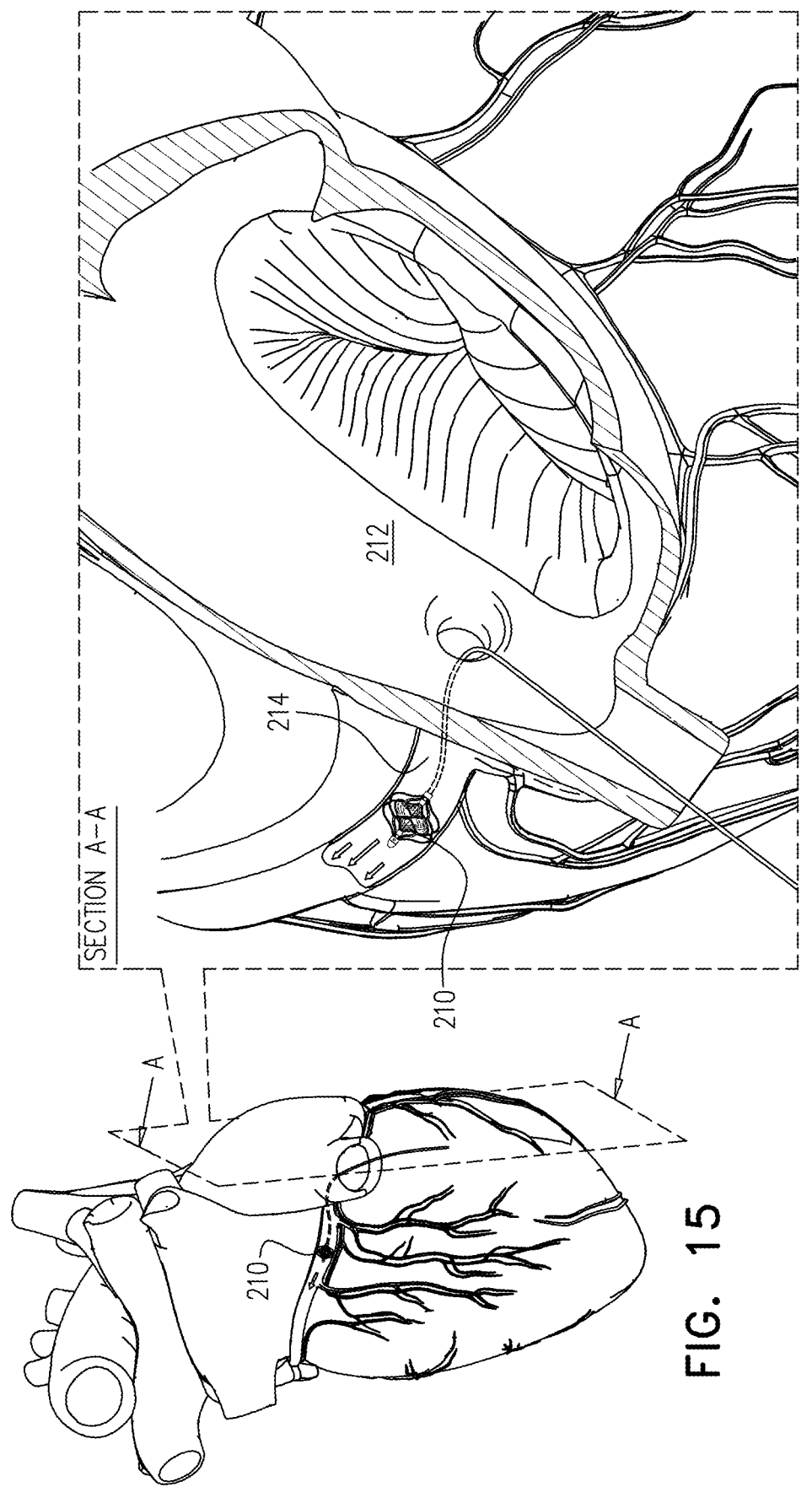
FIG. 15 is a schematic illustration of a blood pump configured to pump blood from a subject's right atrium into the subject's coronary sinus, in accordance with some applications of the present invention.

Reference is now made to FIG. 15, which is a schematic illustration of a blood pump 210 configured to pump blood from a subject's right atrium 212 into the subject's coronary sinus 214, in accordance with some applications of the present invention. For some applications, blood pump 210 is an impeller-based pump that is generally similar to pump 150 described hereinabove. Alternatively or additionally, blood pump 210 may have a different configuration. For some applications, the blood pump is inserted into the subject's right atrium and/or coronary sinus via the subject's vena cava, e.g., from a venous access point that is in the subject's femoral vein, subclavian vein, and/or jugular vein.

Blood pump 210 is configured to pump blood in a retrograde direction, from the subject's right atrium into the subject's coronary sinus. For some applications, by pumping blood into the coronary sinus, the blood pump is configured to increase blood pressure in the coronary sinus, and to thereby increase blood pressure within the capillary system, from which blood flows indirectly into the coronary sinus. This, in turn, increases blood supply to the myocardium. In addition, in cases in which there is a coronary obstruction, perfusion to vascular beds that are distal to the coronary obstruction is increased.

The level of oxygenation of blood in the coronary sinus (which is, typically, approximately 40 percent) is typically lower than that of blood entering to the right atrium from the vena cava (which is, typically, approximately 60-70 percent). For some applications, the blood pump is configured to pump, into the coronary sinus, blood that has returned to the right atrium from the vena cava, thereby increasing the level of oxygenation of the blood in the coronary sinus. This, in turn, increases the level of oxygenation of blood within the capillary system, from which blood flows indirectly into the coronary sinus. It is noted that the above-described effect of increasing the level of oxygenation of blood within the capillary system would not be achieved if a passive obstruction element (e.g., a balloon) were to be used to increase blood pressure within the coronary sinus (e.g., by being placed at the junction between the coronary sinus and the right atrium). By contrast, in accordance with the description hereinabove, blood pump 210 both (a) increases blood pressure within the coronary sinus, and (b) increases the level of oxygenation of blood within the coronary sinus.

Figure 16:
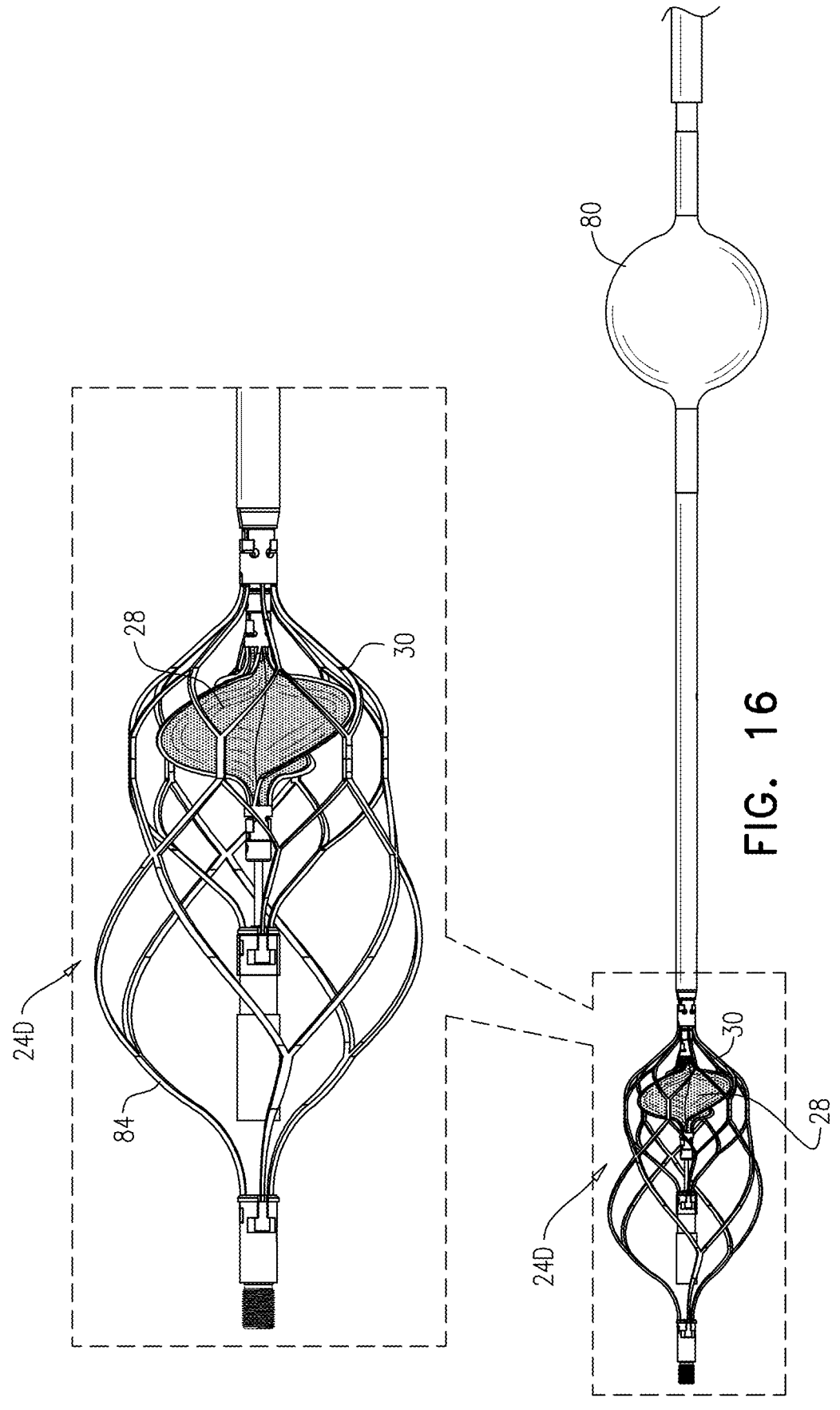
FIG. 16 is a schematic illustration of a catheter that includes a downstream pump and a balloon, in accordance with some applications of the present invention.

Reference is now made to FIG. 16, which is a schematic illustration of a catheter that includes downstream pump 24D and balloon 80, in accordance with some applications of the present invention. The apparatus shown in FIG. 16 is generally similar to that shown in FIG. 5A, except for differences described hereinbelow. The apparatus includes a catheter 20, which includes downstream pump 24D and an occlusion element, such as balloon 80, as shown. For some applications (not shown), a nozzle is used as the upstream occlusion element, e.g., as described in co-pending PCT Patent Application No. PCT/IL2017/051092 to Tuval, filed Sep. 28, 2017, which is incorporated herein by reference. For some applications, downstream pump is placed inside vena cava 22, downstream of the junctions of the vena cava with all of the subject's renal veins. The downstream pump pumps blood through the vena cava, in the downstream direction, away from the junctions of the vena cava with the renal veins, in the manner described hereinabove. For some applications, the occlusion element is placed inside the vena cava upstream of the junctions of the vena cava with the subject's renal veins. Typically, the occlusion element is configured to partially occlude the subject's vena cava upstream of the junctions of the vena cava with the subject's renal veins. The occlusion element is configured to partially occlude the subject's vena cava such that, in response to the pumping of the downstream blood pump, there is not a substantial increase of blood flow from the subject's lower body toward the subject heart, but such that a region of low pressure within the vena cava is generated, between the occlusion element and the downstream blood pump, within which the blood pressure is lower than the subject's central venous pressure. Typically, by generating a region of low pressure, blood flow from the renal veins into the vena cava increases, thereby lowering renal blood pressure and enhancing renal perfusion. It is noted that the occlusion element is configured to partially occlude, but not to totally occlude, the vena cava, in such a manner as to generate a region of low pressure within the vena cava, but to allow a substantial flow of blood through the vena cava.

Figure 17:
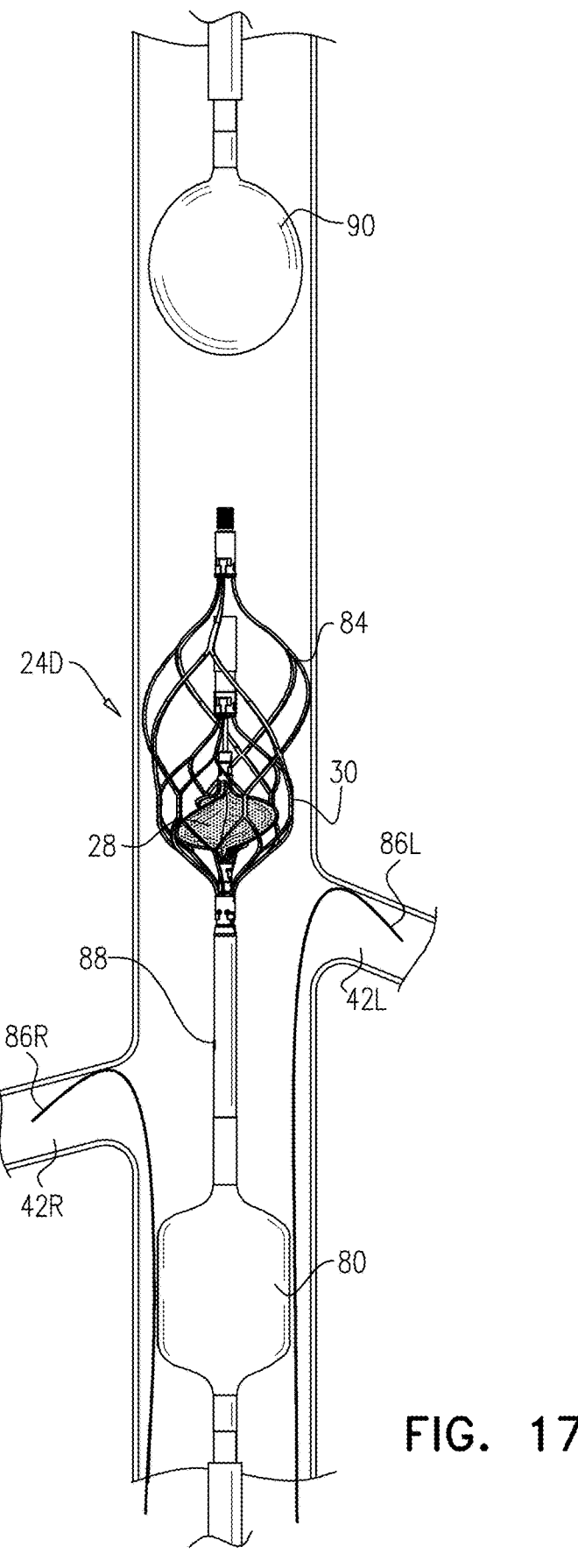
FIG. 17 is a schematic illustration of apparatus that was used in an experiment performed in accordance with some applications of the present invention.

For some applications, impeller 28 of blood pump 24D is disposed inside impeller cage 30, and the impeller cage is not sized such as to hold open the inner wall of the vena cava, the diameter of the cage being less than that of the vena cava under normal conditions, as shown in FIG. 17. In this respect, impeller cage 30 has a generally similar configuration to that described hereinabove with reference to FIGS. 9A-B. Even in such cases, impeller cage 30 typically functions to separate the inner wall of the vena cava from the impeller, e.g., in case the vena cava collapses inwardly due to intra-abdominal pressure, such that the vena cava does not become injured by the impeller and the impeller does not become deformed by pressure from the inner wall of the vena cava. Typically, for such applications, the stiffness of impeller cage 30 is sufficiently great that pressure exerted upon the cage by the inner wall of the vena cava does not deform the cage.

For some such applications, a bulbous extension 84 that is configured to come into contact with the inner wall of the vena cava extends from impeller cage 30. Bulbous extension 84 is configured to align the longitudinal axis of cage 30, and, in turn, impeller 28, with the local longitudinal axis of the vena cava, by contacting the inner wall of the vena cava. (It is noted that, for some applications, the bulbous extension may not fully align the longitudinal axis of impeller with the local longitudinal axis of the vena cava. However, typically, the bulbous extension maintains the longitudinal axis of the impeller in greater alignment with the local longitudinal axis of the vena cava, relative to alignment of the longitudinal axis of the impeller with the local longitudinal axis of the vena cava in the absence of the bulbous extension.) Typically, ceteris paribus, the efficacy of the pumping of blood by impeller 28 is greater, the greater than alignment of the longitudinal axis of the impeller with the local longitudinal axis of the vena cava.

For some applications, the bulbous extension is configured to prevent a pressure sensor that is coupled to blood pump 24D from coming into contact with the inner wall of the vena cava, and to thereby prevent the pressure sensor from measuring the subject's intraabdominal pressure instead of measuring blood pressure within the subject's vena cava, in a generally similar manner to that described hereinabove with reference to FIGS. 13A-B.

Typically, the maximum diameter of bulbous extension 84 (i.e., the diameter of the bulbous extension at the longitudinal location(s) at which the diameter of the bulbous extension is at its maximum), when the bulbous extension is in a non-constrained configuration thereof, is at least 1.1 times (and, for some applications, at least 1.3 times) greater than the maximum diameter of impeller cage 30 (i.e., the diameters of the impeller cage at the longitudinal location(s) at which the diameter of the impeller cage is at its maximum) when the impeller cage is in a non-constrained configuration thereof.

For some applications, rather than defining a bulbous extension, cage 30 defines radially-protruding support arms that are generally similar to radially-protruding support arms described hereinabove with reference to FIGS. 13A-B, mutatis mutandis.

In general, the scope of the present invention includes using any radially-protruding extension from an impeller cage that is, in at least some subjects, undersized with respect to a blood vessel in which the impeller cage is being placed, in order to maintain the longitudinal axis of an impeller (within the impeller cage) in greater alignment with the local longitudinal axis of the blood vessel, relative to alignment of the longitudinal axis of the impeller with the local longitudinal axis of the blood vessel in the absence of the radially-protruding extension. The radially-protruding extension may be a bulbous extension (e.g., as shown in FIG. 16), or radially-protruding support arms (e.g., as shown in FIG. 13A). The blood vessel may include the vena cava (e.g., as shown in FIG. 16), or a renal vein (e.g., as shown in FIG. 13A).

It is noted with respect to the catheter shown in FIG. 16 that such a catheter, which includes a downstream pump 24D disposed distally with respect to an occlusion element 80 is suitable for placement into the vena cava from a vein that is below the junctions of the vena cava with the subject's renal veins, e.g., the femoral vein (e.g., using a generally similar technique to that described hereinabove, with reference to FIG. 4, mutatis mutandis). However, the scope of the present invention includes a catheter that has a pump and an occlusion element disposed thereon, but with the upstream occlusion element disposed distally with respect to the downstream pump. Such a catheter is typically inserted via a vein that is disposed above the inferior vena cava, e.g., the subclavian vein or the jugular vein, e.g., using generally similar techniques to those described hereinabove, with reference to FIGS. 1 and 3, mutatis mutandis.

Reference is now made to FIG. 17, which is a schematic illustration of apparatus that was used in an experiment performed in accordance with some applications of the present invention. A blood-pump catheter, generally as described with reference to FIG. 16 was placed inside the vena cava of a pig weighing 66 kg. Pressure sensors 86L and 86R were placed inside the pig's left and right renal veins in order to measure renal venous pressure. In addition, a pressure sensor 88 was disposed on the shaft of the blood-pump catheter between balloon 80 and the downstream blood pump 24D. An additional balloon 90 was inserted into the pig's vena cava, downstream of the downstream blood pump. The additional balloon was inflated in order to increase the pig's central venous pressure, in order to mimic a subject suffering from high central venous pressure.

The pig initially had central venous pressure of 10 mmHg. The pig's central venous pressure was raised to 20 mmHg, by inflating balloon 90. Pumping of blood by the downstream blood pump was then initiated and the venous pressure as measured by pressure sensors 86L, 86R and 88 were recorded, while the rotation speed of the impeller of blood pump 24D was increased.

Figure 18:
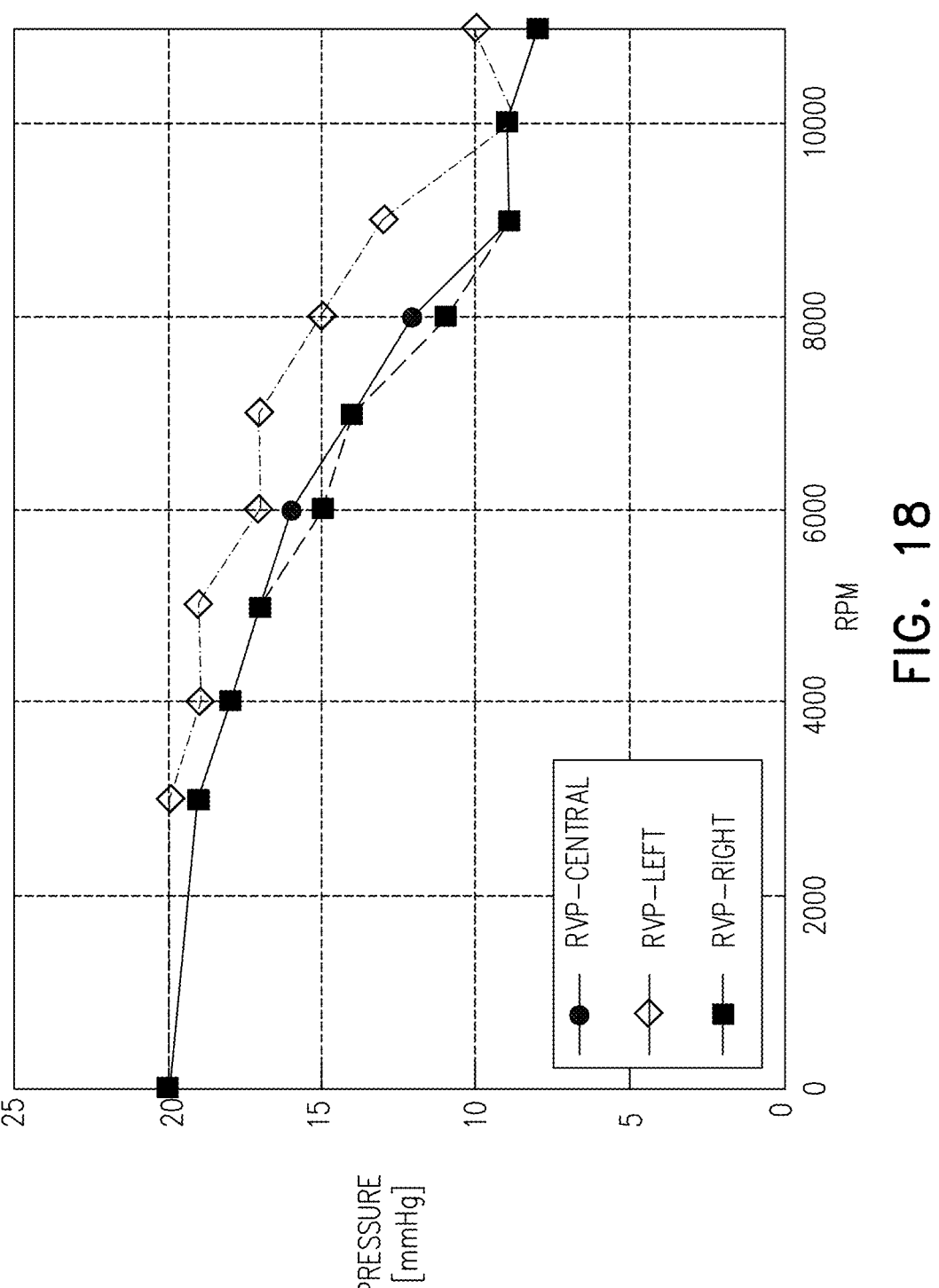
FIG. 18 is a graph showing the results of the experiment that was performed in accordance with some applications of the present invention.

FIG. 18 is a graph showing the results of the experiment that was performed in accordance with some applications of the present invention. The graph shows plots of the renal venous pressure as measured by (a) left renal vein pressure sensor 86L (indicated by "RVP-LEFT" in the legend on the graph), (b) right renal vein pressure sensor 86L (indicated by "RVP-RIGHT" in the legend on the graph), and (c) pressure sensor 88, disposed on the shaft of the blood-pump catheter (indicated by "RVP-CENTRAL" in the legend on the graph), plotted against revolutions per minute (RPM) of the impeller of blood pump 24D. It may be observed that using a blood pump catheter as shown in FIG. 16 cause the renal venous pressure, as measured by all three of the pressure sensors, to fall. It is noted that the drop in pressure recorded by left renal vein pressure sensor 86L was generally lowest. It is hypothesized that this is because the left renal vein is larger than the right renal vein and therefore the resultant pressure drop in the left renal vein is lower than in the right renal vein.

Figure 19A:
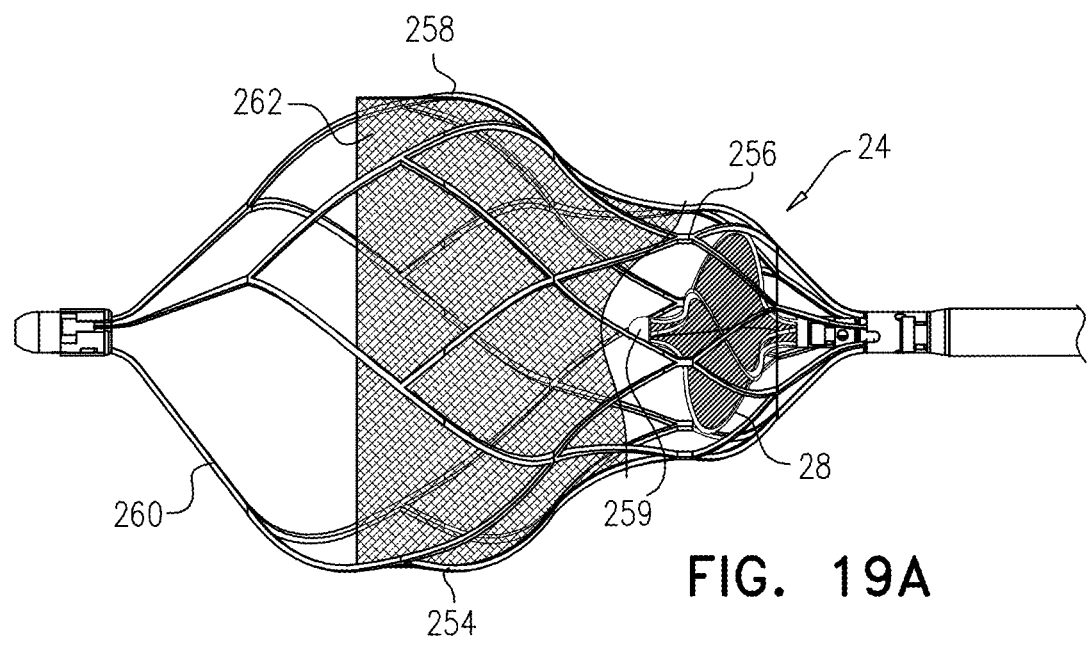
FIGS. 19A and 19B are schematic illustrations of a blood pump, in accordance with some applications of the present invention.
Figure 19B:
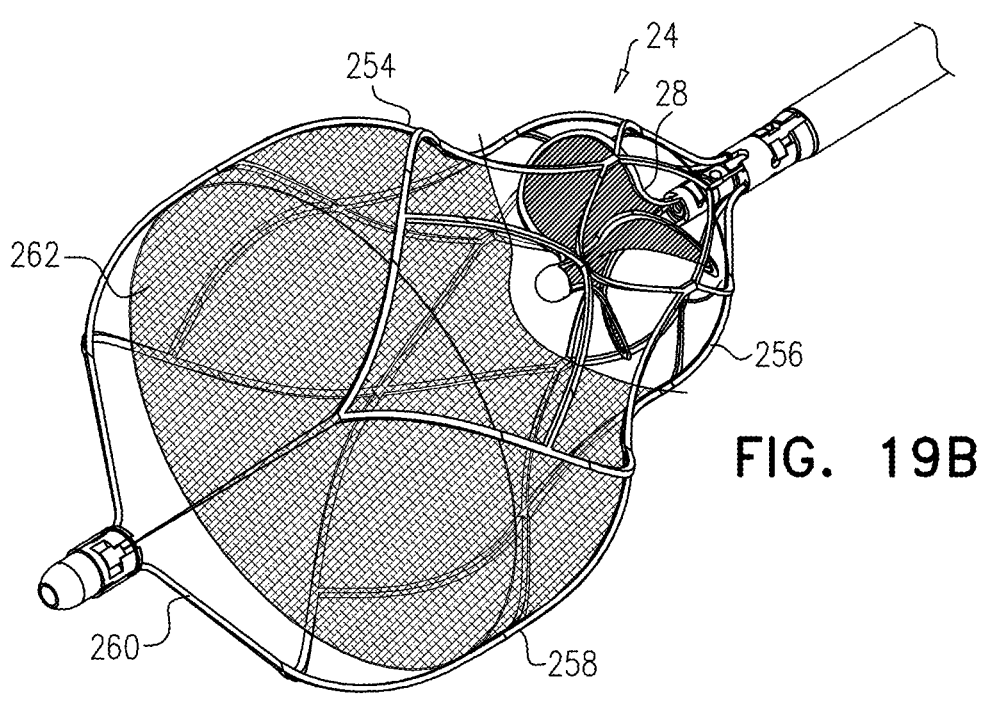

Reference is now made to FIGS. 19A and 19B, which are schematic illustrations of blood pump 24, in accordance with some applications of the present invention. Typically, the blood pump as shown in FIGS. 19A and 19B is used in a generally similar manner to that shown in FIG. 16. That is, blood pump 24 is disposed at the distal end of a catheter, and an occlusion element (e.g., balloon 80, as shown in FIG. 16) is disposed proximally to the blood pump. For some applications, the pump is placed inside vena cava 22, downstream of the junctions of the vena cava with all of the subject's renal veins. The pump pumps blood through the vena cava, in the downstream direction, away from the junctions of the vena cava with the renal veins, in the manner described hereinabove. For some applications, the occlusion element is placed inside the vena cava upstream of the junctions of the vena cava with the subject's renal veins. Typically, the occlusion element is configured to partially occlude the subject's vena cava upstream of the junctions of the vena cava with the subject's renal veins. The occlusion element is configured to partially occlude the subject's vena cava such that, in response to the pumping of the blood pump, there is not a substantial increase of blood flow from the subject's lower body toward the subject heart, but such that a region of low pressure within the vena cava is generated, between the occlusion element and the downstream blood pump, within which the blood pressure is lower than the subject's central venous pressure. Typically, by generating a region of low pressure, blood flow from the renal veins into the vena cava increases, thereby lowering renal blood pressure and enhancing renal perfusion. It is noted that the occlusion element is configured to partially occlude, but not to totally occlude, the vena cava, in such a manner as to generate a region of low pressure within the vena cava, but to allow a substantial flow of blood through the vena cava.

It is noted with respect to the catheter shown in FIGS. 19A-B that such a catheter, which includes pump 24 that is typically disposed distally with respect to an upstream occlusion element, is suitable for placement into the vena cava from a vein that is below the junctions of the vena cava with the subject's renal veins, e.g., the femoral vein (e.g., using a generally similar technique to that described hereinabove, with reference to FIG. 4, mutatis mutandis). However, the scope of the present invention includes a catheter that has a pump and an occlusion element disposed thereon, but with the upstream occlusion element disposed distally with respect to the downstream pump. Such a catheter is typically inserted via a vein that is disposed above the inferior vena cava, e.g., the subclavian vein or the jugular vein, e.g., using generally similar techniques to those described hereinabove, with reference to FIGS. 1 and 3, mutatis mutandis.

Figure 19C:
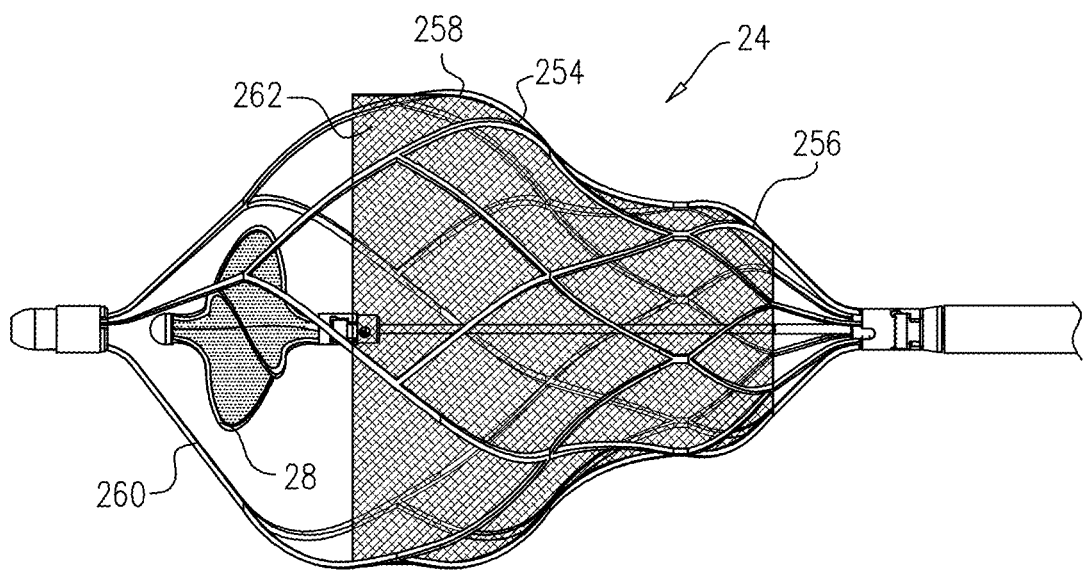
FIG. 19C is a schematic illustration showing relative dispositions into which an impeller and a support cage are placed prior to crimping the impeller and the support cage, in accordance with some applications of the present invention.
Figure 19D:
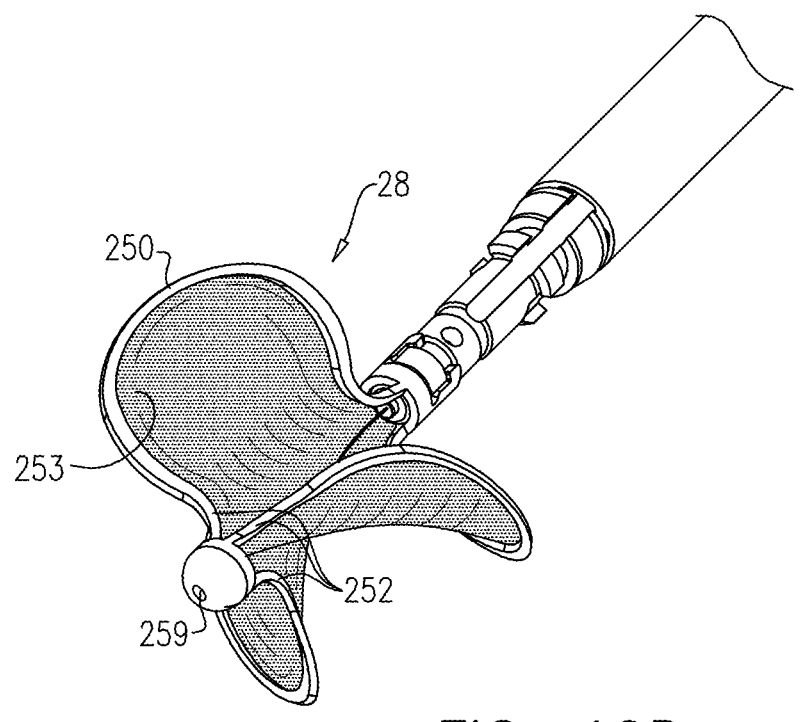
FIG. 19D is a schematic illustration of an impeller of a blood pump, in accordance with some applications of the present invention

Reference is now additionally made to FIG. 19D, which is a schematic illustration of impeller 28 of blood pump 24, in accordance with some applications of the present invention. For some applications, blood pump 24 includes impeller 28, and the distal end of the impeller is not coupled to a distal bearing. For such applications, during use of the impeller, the distal end of the impeller is typically substantially maintained in alignment with a proximal end of the impeller, by virtue of a frame 250 of the impeller being of sufficient stiffness. Typically, the frame of the impeller includes a plurality of helical elongate elements 252, which support a film 253 of a material (e.g., silicone) therebetween. For example, the impeller may be generally as described in US 2016/0022890 to Schwammenthal, which is incorporated herein by reference.

As shown in FIGS. 19A-B, for some applications, impeller 28 is disposed inside a support cage 254, the support cage including a narrow proximal portion 256, in which the impeller is configured to be disposed, during use of blood pump 24. Proximal portion 256 typically functions to separate the inner wall of the vena cava from the impeller (e.g., in case the vena cava collapses inwardly due to intraabdominal pressure), such that the vena cava does not become injured by the impeller and the impeller does not become deformed by pressure from the inner wall of the vena cava. Typically, for such applications, the stiffness of proximal portion 256 is sufficiently great that pressure exerted upon the proximal portion of the support cage by the inner wall of the vena cava does not deform the proximal portion of the support cage.

For some such applications, a bulbous distal extension 258 of the support cage extends from proximal portion 256 of the support cage, and is configured to come into contact with the inner wall of the vena cava. Bulbous distal extension 258 is configured to align the longitudinal axis of support cage 254, and, in turn, impeller 28, with the local longitudinal axis of the vena cava, by contacting the inner wall of the vena cava. (It is noted that, for some applications, the bulbous distal extension may not fully align the longitudinal axis of impeller with the local longitudinal axis of the vena cava. However, typically, the bulbous distal extension maintains the longitudinal axis of the impeller in greater alignment with the local longitudinal axis of the vena cava, relative to alignment of the longitudinal axis of the impeller with the local longitudinal axis of the vena cava in the absence of the bulbous extension.) Typically, ceteris paribus, the efficacy of the pumping of blood by impeller 28 is greater, the greater than alignment of the longitudinal axis of the impeller with the local longitudinal axis of the vena cava.

For some applications, bulbous distal extension 258 of support cage 254 is configured to prevent a pressure sensor 259 that is coupled to blood pump 24 from coming into contact with the inner wall of the vena cava, and to thereby prevent the pressure sensor from measuring the subject's intraabdominal pressure instead of measuring blood pressure within the subject's vena cava, in a generally similar manner to that described hereinabove with reference to FIGS. 13A-B.

Typically, the maximum diameter of bulbous distal extension 258 (i.e., the diameter of the bulbous distal extension at the longitudinal location(s) at which the diameter of the bulbous distal extension is at its maximum), when the bulbous distal extension is in a radially non-constrained configuration thereof, is at least 1.1 times (and, for some applications, at least 1.3 times) greater than the maximum diameter of proximal portion 256 of support cage 254 (i.e., the diameter of the proximal portion at the longitudinal location(s) at which the diameter of the proximal portion is at its maximum) when the proximal portion is in a radially non-constrained configuration thereof.

For some applications, support cage 254 includes a frame 260 (e.g., a rigid or semi-rigid frame) made of a shape-memory element (such as nitinol) that is at least partially covered with a material 262 (e.g., a blood-impermeable material, e.g., polyester, polyurethane, and/or a different polymer). Typically, the material is coupled to the frame such as to contact the vessel wall and to occlude the blood vessel in the region of the blood vessel that surrounds the impeller. The material typically defines a hole therethrough in a central region of the vessel in a vicinity of the impeller. The material is configured to occlude backflow of blood around the outside of the impeller, but such to allow antegrade blood flow in the central region of the vessel in the vicinity of the impeller. For some applications, the use of the material in the above-described manner reduces a likelihood of there being retrograde blood flow in the region of the blood vessel that surrounds the impeller, caused by turbulence that is introduced by the impeller. For some applications (not shown), blood pump 24 as shown in FIG. 16 includes material that is coupled to cage 30 and/or bulbous extension 84, and that is configured to act in a generally similar manner to that described with reference to material 262.

For some applications, rather than defining a bulbous distal extension, support cage 254 defines radially-protruding support arms that are generally similar to radially-protruding support arms described hereinabove with reference to FIGS. 13A-B, mutatis mutandis.

Reference is now made to FIG. 19C, which shows relative dispositions into which impeller 28 and support cage 254 are placed prior to crimping the impeller and the support cage, in accordance with some applications of the present invention. Support cage 254 is typically shape-set such as to assume a radially expanded configuration thereof in the absence of any radially constraining force acting upon the support cage, the radially expanded configuration being as shown in FIGS. 19A-B. The support cage is inserted into the subject's vena cava, while the support cage is in a radially constrained configuration (i.e., crimped) inside the guide catheter, and is configured to assume a substantially radially non-constrained configuration by being released from the guide catheter inside the subject's vena cava.

For some applications, a distal portion of support cage 254 is not covered with material 262. Furthermore, it is typically the case that, as shown, the spacing between struts of the frame of the support cage at its distal end is greater than at the proximal end of the support cage. Therefore, for some applications, in order to crimp the impeller inside the support cage, the impeller is first advanced to the distal portion of the support cage. Typically, this allows for the combination of the impeller and the support cage to be crimped to a smaller diameter relative to if the impeller was disposed within the proximal portion of the support cage, since the impeller, by being disposed within the distal portion of the support cage, does not overlap with the material or with the portion of the support cage at which the struts of the support cage are closely spaced from each other. Further typically, this reduces the likelihood of the material and the impeller causing damage to one another during the crimping of the support cage and the impeller, relative to if the impeller was disposed within the proximal portion of the support cage. Subsequently, once the support cage and the impeller assume radially-non-constrained configurations inside the subject's vena cava, and prior to operating the impeller, the impeller is retracted with respect to the support cage, such that the impeller is disposed within the proximal portion of the support cage, as shown in FIGS. 19A and 19B.

Figure 20A:
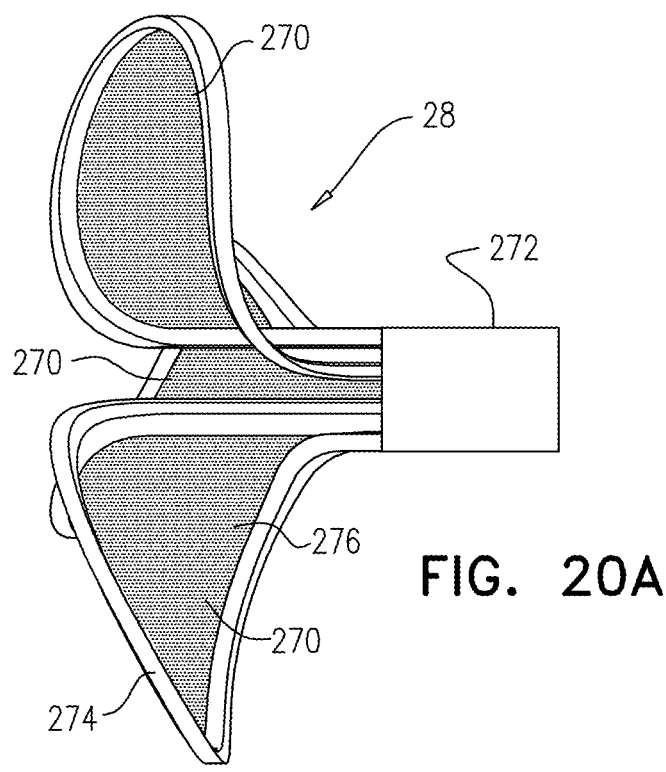
FIGS. 20A and 20B are schematic illustrations of an impeller of a blood pump, in accordance with some applications of the present invention
Figure 20B:
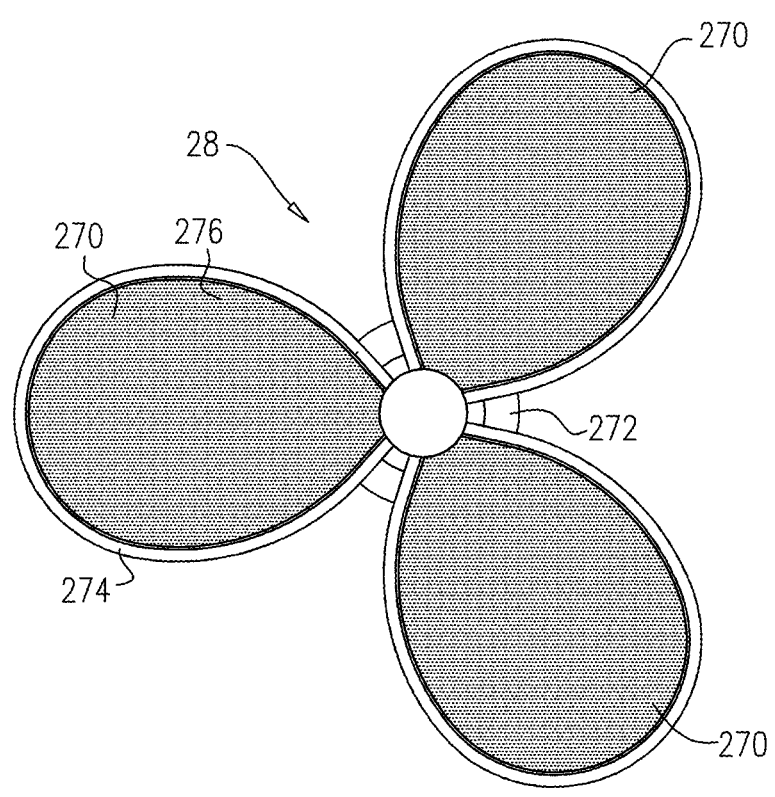

Reference is now additionally made to FIGS. 20A and 20B, which are schematic illustrations of impeller 28 of blood pump 24, in accordance with some applications of the present invention. As described hereinabove, with reference to FIG. 19D, for some applications, blood pump 24 includes impeller 28, and the distal end of the impeller is not coupled to a distal bearing. For some such applications, impeller 28 is as shown in FIGS. 20A and 20B, the impeller including a plurality (e.g., two, three (as shown), or more than three) impeller blades 270, which are not directly connected with each other. As shown, for some applications, the impeller blades protrude in a petal-like manner from a proximal bearing 272. Each of the blades typically includes a curved rigid or semi-rigid elongate element 274, which defines the outer edge of the blade and which extends from the proximal bearing from a first location around the circumference of the proximal bearing and curves back to a second location around the circumference of the proximal bearing. The curved elongate element 274 typically supports a film of material 276 (e.g., silicone), the curved elongate element and the film of material defining the impeller blade. Typically, impeller 28 as shown in FIGS. 20A and 20B is configured such that more than 80 percent of the mass of the impeller is concentrated within the proximal-most 50 percent of the length of the impeller. Typically, the relative concentration of the mass within the proximal-most 50 percent of the length of the impeller reduces vibration of the impeller during use of the impeller, relative to if more of the mass of the impeller was disposed within the distal-most 50 percent of the length of the impeller.

Figure 21A:
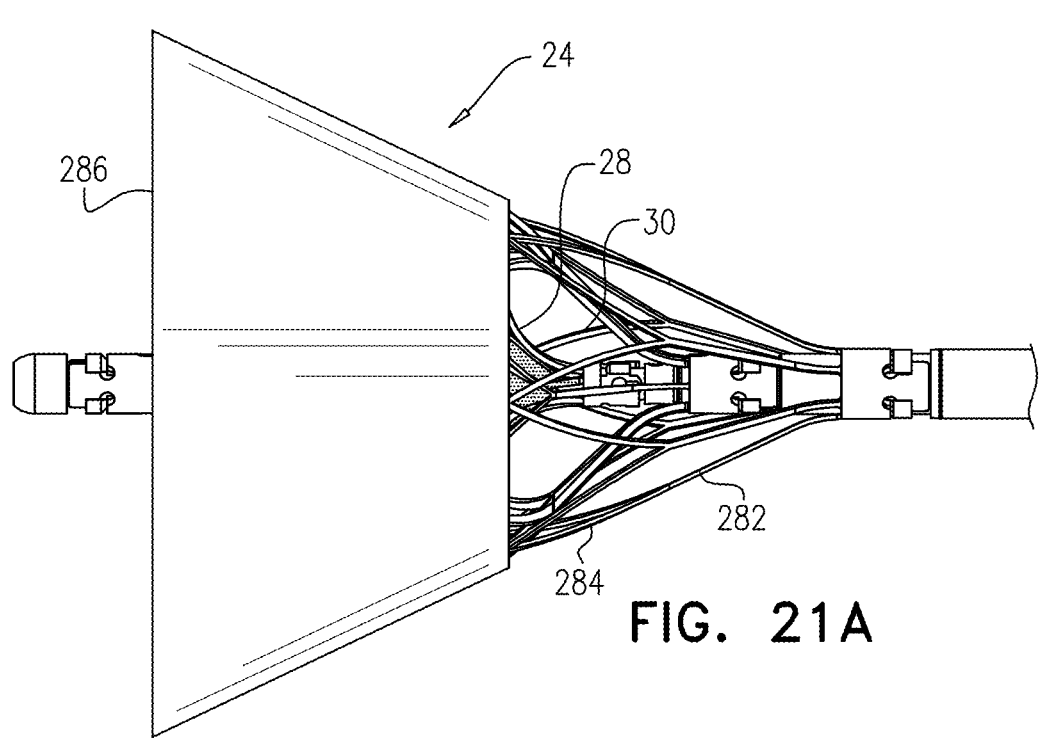
FIGS. 21A and 21B are schematic illustrations of a blood pump that includes an impeller, an impeller cage, and a frustoconical support cage, in accordance with some applications of the present invention.
Figure 21B:
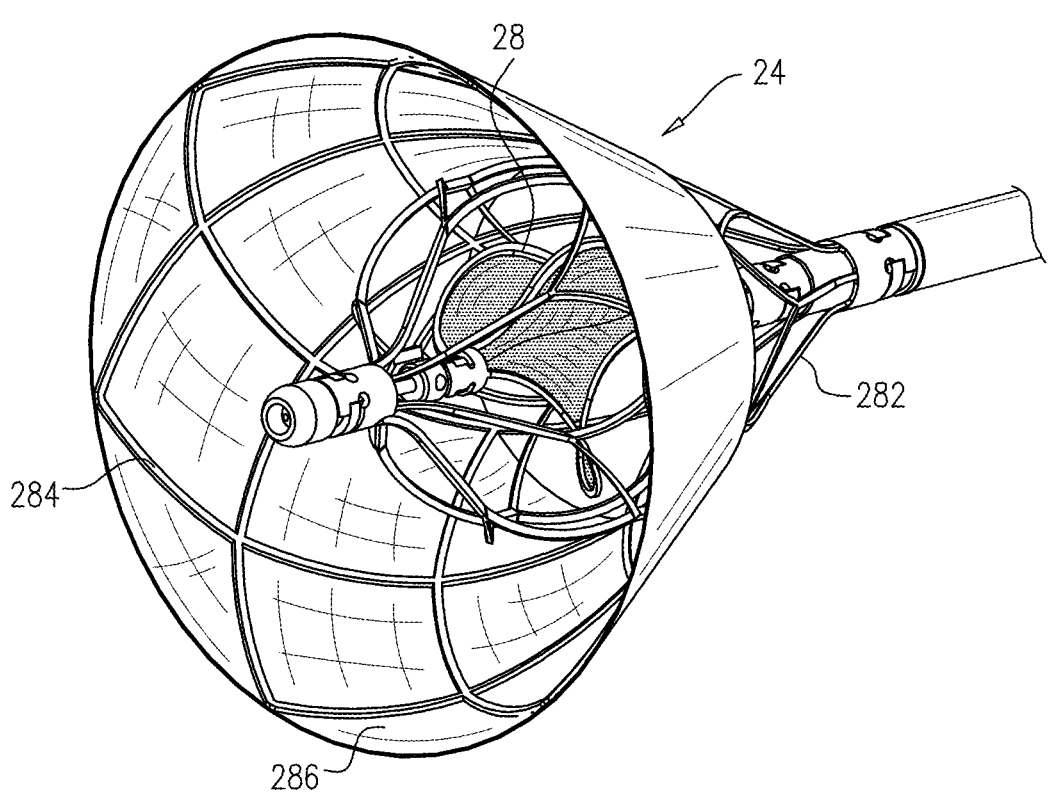

Reference is now made to FIGS. 21A and 21B, which are schematic illustrations of blood pump 24, the blood pump including impeller 28, impeller cage 30, and a frustoconical support cage 282, in accordance with some applications of the present invention. Blood pump 24 is generally similar to that described hereinabove with reference to FIG. 16, except for the differences described hereinbelow. For some applications, instead of bulbous extension 84 (as shown in FIG. 16), frustoconical support cage is used to align the longitudinal axis of cage 30, and, in turn, impeller 28, with the local longitudinal axis of the vena cava, by contacting the inner wall of the vena cava. The frustoconical support cage typically extends from a location that is proximal to the impeller cage to a longitudinal location that is distal to the impeller cage, with the cage diverging in the proximal-to-distal direction. For some applications, the frustoconical support cage includes a frame 284 (e.g., a rigid or semi-rigid frame) made of a shape-memory element (such as nitinol) that is at least partially covered with a material 286 (e.g., a blood-impermeable material, e.g., polyester, polyurethane, and/or a different polymer). Material 286 typically acts in a generally similar manner to that described with reference to material 262, described hereinabove with reference to FIGS. 19A-C.

Frustoconical support cage 282 is typically shape-set such as to assume a radially expanded configuration thereof in the absence of any radially constraining force acting upon the support cage, the radially expanded configuration being as shown in FIGS. 21A-B. The frustoconical support cage is typically inserted into the subject's vena cava, while the support cage is in a radially constrained configuration (i.e., crimped) inside the guide catheter, and is configured to assume a substantially radially non-constrained configuration by being released from the guide catheter inside the subject's vena cava.

As described hereinabove with reference to FIGS. 21A and 21B, for some applications, pump 24 is disposed upon a catheter distally with respect to an upstream occlusion element. Such a catheter is suitable for placement into the vena cava from a vein that is below the junctions of the vena cava with the subject's renal veins, e.g., the femoral vein (e.g., using a generally similar technique to that described hereinabove, with reference to FIG. 4, mutatis mutandis). The scope of the present invention includes a catheter that has a pump and an occlusion element disposed thereon, but with the upstream occlusion element disposed distally with respect to the downstream pump. Such a catheter is typically inserted via a vein that is disposed above the inferior vena cava, e.g., the subclavian vein or the jugular vein, e.g., using generally similar techniques to those described hereinabove, with reference to FIGS. 1 and 3, mutatis mutandis.

With reference to FIGS. 9A-B, 10A-D, 11A-C, 13A-B, 16, 19A-B, and 21A-B, it is noted that the scope of the present invention includes any blood pump configured to be placed inside a blood vessel of a subject, and which includes (a) an impeller configured to pump blood by rotating, and (b) a support cage that is shaped to define (i) a narrow portion that is configured to be disposed around the impeller, and to maintain a separation between a wall of the blood vessel and the impeller, and (ii) a radial extension from the narrow portion of the support cage that extends radially outward with respect to the narrow portion of the support cage, the extension being configured to substantially maintain a longitudinal axis of the impeller in alignment with a local longitudinal axis of the blood vessel by contacting the wall of the blood vessel. For some applications, the narrow portion and the radial extension of the support cage are two separately-formed components. Alternatively, the narrow portion and the radial extension of the support cage are separate portions of a single integrated component.

Typically, such applications are used with an impeller that is undersized with respect to the vessel in which it is placed. Such an impeller may be used, for example, in cases in which a larger impeller would undergo a substantial amount of vibration while rotating. Alternatively or additionally, such an impeller may be used in cases in which, if the portion of the cage that is configured to separate between the impeller and the vessel wall was larger, there would be a risk that the portion of the cage would become radially compressed by the walls of the vessel, which may result in the impeller becoming deformed (e.g., by the upstream and downstream ends of the impeller axis becoming misaligned), and/or in the impeller becoming misaligned with the local longitudinal axis of the vessel. Typically, for such applications, a narrow portion of the cage surrounds the impeller and is configured to maintain a separation between a wall of the blood vessel and the impeller, for example, in case the vessel narrows, such that, in the absence of the narrow portion of the cage, the walls of the vessel would collapse onto the impeller. The radial extension is typically configured to anchor the blood pump within the vessel by exerting an outward radial force upon the vessel wall, and to substantially maintain a longitudinal axis of the impeller in alignment with a local longitudinal axis of the blood vessel by contacting the wall of the blood vessel. Typically, a stiffness of the narrow portion of the cage is greater than that of the radial extension, such that the narrow portion of the cage is configured to maintain the separation between the wall of the blood vessel and the impeller, even if the wall of the vessel exerts pressure upon the support cage that causes the radial extension to deform.

For example, with reference to FIGS. 9A-B, the blood pump includes impeller 28, cage 30, which constitutes a narrow portion of the overall support cage, and support cage 180, which constitutes a radial extension from the narrow portion of the cage. With reference to FIGS. 10A-D, the blood pump includes impeller 28, cage 30, which constitutes a narrow portion of the overall support cage, and support sleeve 190, which constitutes a radial extension from the narrow portion of the cage. With reference to FIGS. 11A-C, the blood pump includes impeller 28, cage 30, which constitutes a narrow portion of the overall support cage, and support sleeve 200, which constitutes a radial extension from the narrow portion of the cage. With reference to FIGS. 13A-B, the blood pump includes impeller 152, cage 154, which constitutes a narrow portion of the support cage, and radially-protruding support arms 156, which constitute radial extensions from the narrow portion of the cage. With reference to FIG. 16, the blood pump includes impeller 28, cage 30, which constitutes a narrow portion of the support cage, and bulbous extension 84, which constitutes a radial extension from the narrow portion of the cage. With reference to FIGS. 19A-B, the blood pump includes impeller 28, narrow proximal portion 256, which constitutes a narrow portion of the support cage 254, and bulbous distal extension 258, which constitutes a radial extension from the narrow portion of the cage. With reference to FIGS. 21A-B, the blood pump includes impeller 28, impeller cage 30, which constitutes a narrow portion of the support cage, and frustoconical support cage 282, which constitutes a radial extension from the narrow portion of the cage. For some applications, the radial extension extends from the narrow portion of the cage distally with respect to the narrow portion. Alternatively or additionally, the radial extension extends from the narrow portion of the cage proximally with respect to the narrow portion, and/or level with the narrow portion.

For some applications, a material (e.g., blood-impermeable material) is disposed on the support cage (e.g., material 262, shown in FIGS. 19A-B). Typically, the material is coupled to the support cage such as to contact the vessel wall and to occlude the blood vessel in the region of the blood vessel that surrounds the impeller. The material typically defines a hole therethrough in a central region of the vessel, in a vicinity of the impeller. The material is configured to occlude backflow of blood around the outside of the impeller, but such as to allow antegrade blood flow in the central region of the vessel in the vicinity of the impeller.

For some applications, such a blood pump is configured to be placed within a subject's renal vein and to pump blood from the subject's renal vein into the subject's vena cava, e.g., as described hereinabove with reference to FIGS. 13A-B. For some applications, such a blood pump is configured to be placed within a subject's vena cava upstream of the junctions of the vena cava with all of the subject's renal veins, and to pump blood in a retrograde (i.e., upstream) direction, e.g., as described herein with reference to FIG. 22B. Alternatively or additionally, such a blood pump is configured to be placed within a subject's vena cava downstream of the junctions of the vena cava with all of the subject's renal veins, and to pump blood in an antegrade (i.e., downstream) direction, e.g. as described herein with reference to FIG. 22C. For some such applications, an occlusion element is configured to be placed within the subject's vena cava upstream of the junctions of the vena cava with all of the subject's renal veins, and to partially occlude the vena cava, e.g., as described herein with reference to FIG. 22C. For some applications, upstream and downstream blood pumps are disposed on a single catheter, e.g., as described hereinabove with reference to FIGS. 1A-C. Alternatively, an upstream occlusion element, and a downstream blood pump are disposed on a single catheter, e.g., as described herein with reference to FIGS. 5A-B, 16, and 22C. In accordance with some applications, the catheter is introduced into the vena cava from a vein that is above the inferior vena cava (e.g., the jugular vein or the subclavian vein), in which case the upstream pump or occlusion element is disposed upon the catheter distally with respect to the downstream blood pump, as described herein with reference to FIGS. 1A and 3. Alternatively, the catheter is introduced into the vena cava from a vein that is below the junctions of the vena cava with the subject's renal veins (e.g., the femoral vein), in which case the upstream pump or occlusion element is disposed upon the catheter proximally with respect to the downstream blood pump, e.g., as described herein with reference to FIG. 4.

Figures 22A, 22B, 22C:
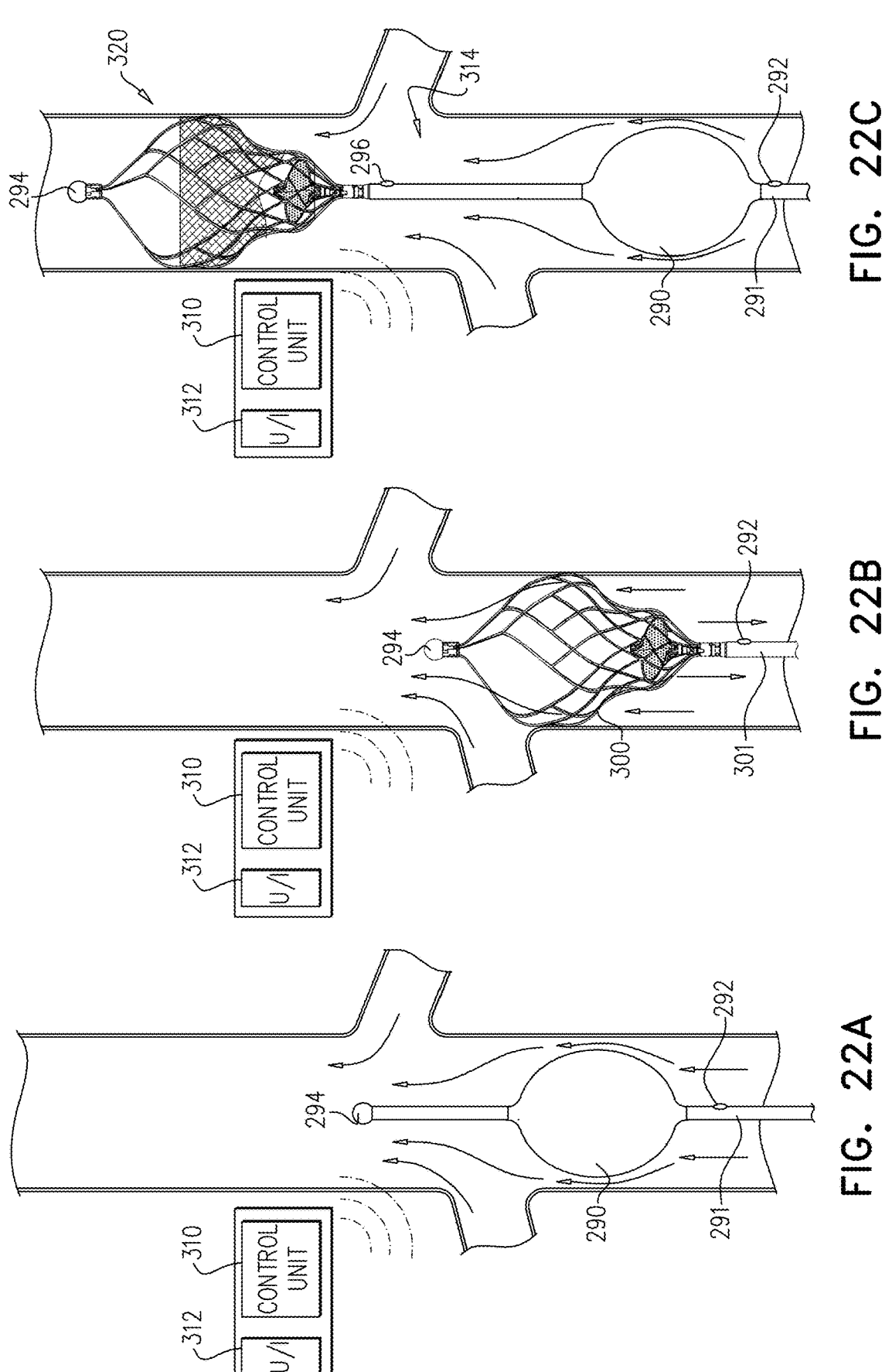
FIGS. 22A and 22B are schematic illustrations of an occlusion element and a blood pump, the occlusion element or the blood pump being placed in a subject's infra-renal vena cava (i.e., within the vena cava, upstream of junctions of the vena cava with all of a subject's renal veins), in accordance with respective applications of the present invention.
FIG. 22C is a schematic illustration of a catheter that includes a downstream pump and an upstream balloon, in accordance with some applications of the present invention.

Reference is now made to FIGS. 22A and 22B, which are schematic illustrations of an occlusion element 290 disposed upon a catheter 291 (FIG. 22A), and a blood pump 300 disposed upon a catheter 301 (FIG. 22B), the occlusion element or the blood pump being placed in a subject's infra-renal vena cava (i.e., within the vena cava, upstream of junctions of the vena cava with all of a subject's renal veins), in accordance with respective applications of the present invention. Typically, occlusion element 290, or blood pump 300, is inserted into the vena cava of a subject suffering from acute heart failure. For some applications, occlusion element is as described hereinabove with reference to FIGS. 5A and 5B, except for differences described hereinbelow. For some applications, blood pump 300 is generally similar to blood pumps described hereinabove. For example, as shown in FIG. 22B, blood pump 300 may be generally configured like blood pump 24 described hereinabove with reference to FIGS. 19A-D.

Typically, in patients suffering from acute heart failure, elevated systemic venous pressures cause increased renal parenchymal pressure and increased intraabdominal pressure, factors that can contribute to deterioration of renal perfusion and function. In addition, high systemic venous pressures may impede lymphatic drainage of pulmonary interstitial fluid resulting in aggravation and prolongation of pulmonary congestion in patients with acute pulmonary edema. For some applications, occlusion element 290 is configured to cause partial occlusion of the infra-renal vena cava, or blood pump 300 is used to pump blood in a retrograde direction within the infra-renal vena cava. Typically, use of occlusion element 290 or blood pump 300 in this manner reduces cardiac preload, by causing lower body venous pooling. Typically, reducing cardiac preload ameliorates pulmonary congestion and/or improve cardiac loading conditions and function. For some applications, a blood pump that is generally similar to that described with reference to FIGS. 19A-D is used for the application shown in FIG. 22B. However, it is noted that for applications as shown in FIG. 22B, blood pump 300 typically does not include material 262 (shown in FIG. 19A, for example) since it is desirable to allow antegrade blood flow through the vena cava around the outside of the region that immediately surrounds the impeller.

Due to gravity, the effect of infra-renal vena-caval occlusion by occlusion element 290, or infra-renal vena-caval retrograde blood pumping by blood pump 300 on renal and pulmonary function may be highly dependent on patient position. For example, bringing the patient into an upright position, is known to alleviate pulmonary congestion, but to aggravate renal congestion. Moreover, it is important to balance the positive of effects of reducing venous blood pressure against the possible negative effect of causing too great a reduction in cardiac output. This is of particular concern in the severely ill and fragile patient group of acute heart failure, for whom it is critical to avoid a drop in cardiac output. Therefore, in view of the aforementioned considerations, in accordance with some applications of the present invention, the extent to which occlusion element 290 occludes the infra-renal vena cava, and/or the rate at which blood pump 300 pumps blood, is controlled by a control unit 310.

For example, occlusion element 290 may include a balloon (as shown), and inflation of the balloon may be controllable. Alternatively, the occlusion element includes a frame (e.g., as shown in FIG. 5B), which is expandable (e.g., by heating the frame, or by applying an electrical current to the frame). Further alternatively, the occlusion element includes a nozzle, the diameter of an opening of which is controllable, e.g., as described in co-pending PCT Patent Application No. PCT/IL2017/051092 to Tuval, filed Sep. 28, 2017, which is incorporated herein by reference. For some applications, the extent to which the occlusion element occludes the vena cava is controlled by control unit 310 responsively to the parameters detected by sensors. For example, a first sensor 292 may be disposed upstream of the occlusion element, and a second sensor 294 may be disposed downstream of the occlusion element. For some applications, the first and second sensors are blood pressure sensors configured to measure, respectively, lower body venous blood pressure and central venous blood pressure. Alternatively or additionally, the first and second sensors may be flow sensors, blood velocity sensors, oxygen-saturation sensors, temperature sensors, and/or thermal flow sensors (e.g., as described with reference to FIGS. 22Ai-Cii of US 2016/0022890 to Schwammenthal, which is incorporated herein by reference), the first and second sensors being configured to measure lower body venous parameters and central venous parameters, respectively.

For some applications, upstream sensor 292 is mounted upon catheter 291 or catheter 301 at a location that is at least 1.5 cm (e.g., at least 2.5 cm) upstream of occlusion element 290, or upstream of blood pump 300, such that by the time that the blood flow reaches the occlusion element or the blood pump, any effect on the direction of the blood flow caused by the sensor has substantially dissipated. For some applications, downstream sensor 294 is mounted upon catheter 291 or catheter 301 at a location that is at least 1.5 (e.g., at least 2.5 mm) downstream of occlusion element 290, or downstream of blood pump 300, such that by the time that the blood flow reaches sensor 294, flow layers generated by having passed the occlusion element or the blood pump are sufficiently reunited to permit accurate measurement of flow, pressure, velocity, and/or other parameters as described hereinabove. For some applications, downstream sensor 294 is mounted upon catheter 291 or catheter 301 at a location that is at least 1.5 (e.g., at least 2.5 mm) downstream of the junction of the vena cava with the right renal vein, and/or at least 1.5 (e.g., at least 2.5 mm) downstream of junctions of the vena cava with all of the subject's renal veins.

Figure 23:
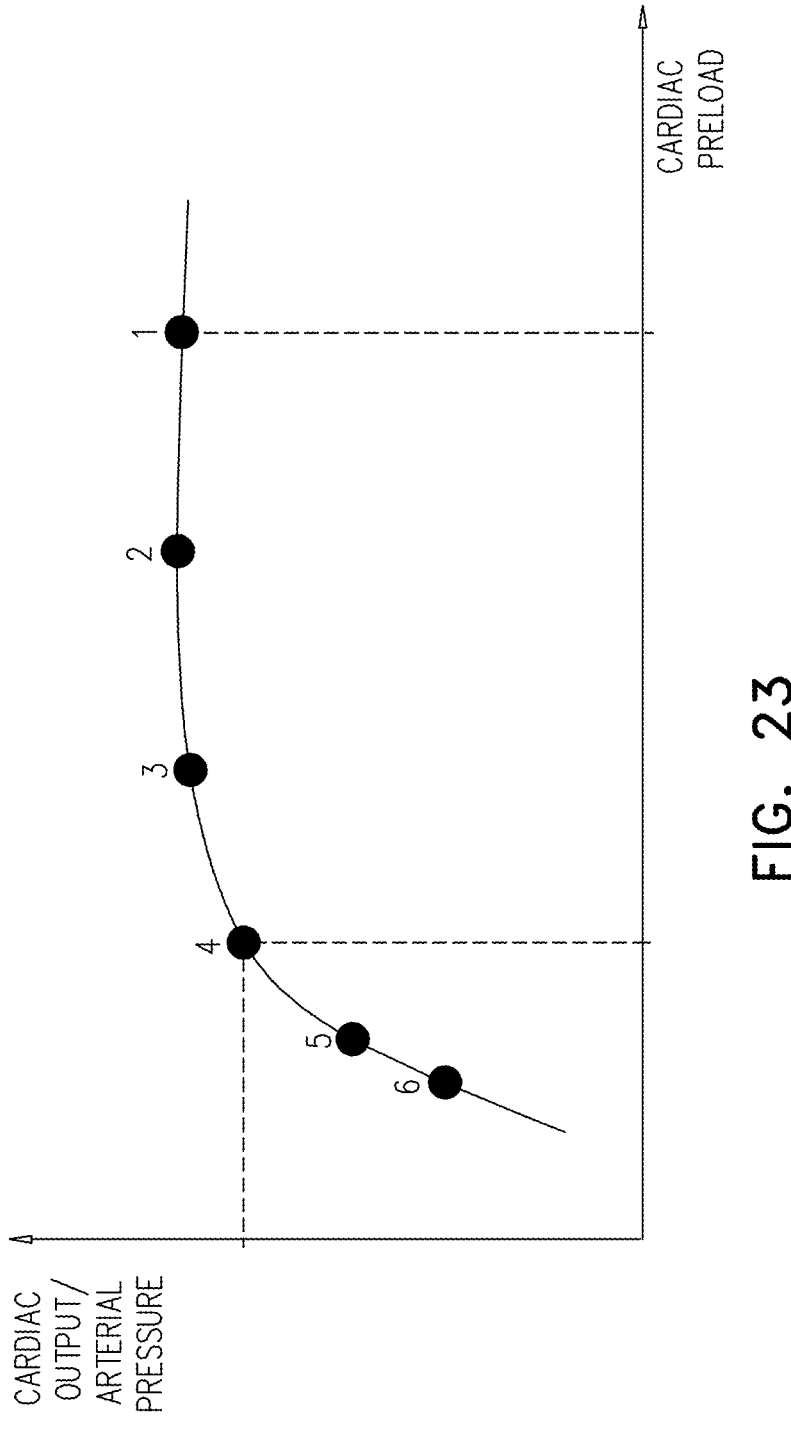
FIG. 23 is a curve showing the relationship between (a) cardiac preload and (b) cardiac output and/or arterial pressure, when the occlusion element of FIG. 22A or the blood pump of FIG. 22B is used, in accordance with some applications of the present invention.

Reference is now made to FIG. 23, which is a curve showing the relationship between (a) cardiac preload and (b) cardiac output and/or arterial pressure, when the occlusion element of FIG. 22A or the blood pump of FIG. 22B is used, in accordance with some applications of the present invention. Typically, an indication of cardiac preload is measured, for example, by measuring central venous pressure (e.g., using sensor 294), renal venous pressure, cardiac diameter and/or cardiac volume. Further typically, an indication of cardiac output and/or arterial pressure is measured, for example, by measuring arterial blood flow, minute flow, arterial flow velocity, and/or arterial blood pressure. For some applications, control unit 310 monitors the indication of cardiac preload, and modulates the extent to which the occlusion element occludes the infra-renal vena cava, and/or the rate at which the blood pump pumps blood, in response thereto. For some applications, the control unit is configured to modulates the extent to which the occlusion element occludes the infra-renal vena cava, and/or the rate at which the blood pump pumps blood, by first (algorithmically) generating a pressure-flow curve, e.g., as shown in FIG. 23. For some applications, the control unit then automatically sets the extent to which the occlusion element occludes the infra-renal vena cava, and/or the rate at which the blood pump pumps blood, by determining the highest degree of obstruction, or reverse blood flow, attainable without decreasing cardiac output and/or arterial pressure by more than a given threshold.

By way of example, before the occlusion element or the blood pump are used, central venous blood pressure and blood flow may be at position 1 upon the curve shown in FIG. 23. As the extent to which the occlusion element occludes the infra-renal vena cava is increased, or as the rate at which the blood pump pumps blood is increased, the cardiac preload and cardiac output and/or arterial pressure moves along the curve from position 2, through to position 6. For example, with reference to the points shown on the graph of FIG. 23, point 4 may be the optimal level of cardiac preload reduction, since there is a substantial reduction in cardiac preload without decreasing cardiac output and/or arterial pressure. By contrast, at points 5 and 6, the level of reduction in cardiac output and/or arterial pressure may be dangerous for the patient.

For some applications, a thermodilution catheter (e.g., a commercially available thermodilution catheter) is used to measure cardiac output. Alternatively, a different type of sensor is used to measure cardiac output, in accordance with techniques that are known in the art. Control unit 310 is configured to receive the measured cardiac output and to use the measured cardiac output as an input signal for determining the extent to which the occlusion element should occlude the infra-renal vena cava, and/or the rate at which the blood pump should pump blood, in accordance with the techniques described hereinabove. Alternatively or additionally, arterial blood pressure may be measured and may be used as an input signal for the control unit to determine the extent to which the occlusion element should occlude the infra-renal vena cava, and/or the rate at which the blood pump should pump blood. For example, the control unit may be configured to detect a relationship between decreases in central venous pressure and corresponding decreases in arterial pressure. The control unit may then be configured to set the level of occlusion or the rate of pumping, such that there is no decrease in arterial pressure, or such that the decrease in arterial pressure is below a given threshold, in accordance with the techniques described hereinabove.

Reference is now made to FIG. 22C, which is a schematic illustration of a catheter 314 is placed into a subject's vena cava, the catheter including a downstream pump 320 and an occlusion element, such as balloon 290, in accordance with some applications of the present invention. For some applications, the downstream pump is generally similar to pump 24 described with reference to FIGS. 19A-D. Alternatively or additionally, a different one of the pumps described hereinabove is used. For some applications, the occlusion element is similar to any of the occlusion elements described hereinabove. Typically, the extent to which the occlusion element occludes the vena cava can be controlled, e.g., using techniques as described hereinabove.

Typically, the downstream pump is placed downstream of the junctions of the vena cava with all of the subject's renal veins, and pumps blood through the vena cava, in the downstream direction, away from the junctions of the vena cava with the renal veins. Typically, the occlusion element is placed upstream of the junctions of the vena cava with all of the subject's renal veins and is configured to partially occlude the subject's vena cava upstream of the junctions of the vena cava with the subject's renal veins. The occlusion element is configured to partially occlude the subject's vena cava such that, in response to the pumping of the downstream blood pump, there is not a substantial increase of blood flow from the subject's lower body toward the subject heart, but such that a region of low pressure within the vena cava is generated, between the occlusion element and the downstream blood pump, within which the blood pressure is lower than the subject's central venous pressure. Typically, by generating a region of low pressure, blood flow from the renal veins into the vena cava increases, thereby lowering renal blood pressure and enhancing renal perfusion. For some applications, the combination of the downstream pump and the upstream occlusion element is configured such that the overall effect of the downstream pump and the upstream occlusion element is that (a) central venous pressure is lowered relative to lower body venous pressure (e.g., by the pumping of the downstream pump not fully compensating for the reduction in pressure caused by the occlusion of the vena cava by the upstream occlusion element), and (b) renal venous pressure is lowered relative to lower body venous pressure and central venous pressure, due to the region of low pressure being generated within the vena cava, between the occlusion element and the downstream blood pump.

For some applications, sensor 292 is disposed upstream of the occlusion element and is configured to measure a parameter that is indicative of lower body venous pressure, sensor 294 is disposed downstream of the blood pump and is configured to measure a parameter that is indicative of central venous pressure, and sensor 296 is disposed between the occlusion element and the blood pump, and is configured to measure a parameter that is indicative of renal venous pressure. For example, sensors 292, 294, and/or 296 may be pressure sensors, flow sensors, blood velocity sensors, oxygen-saturation sensors, temperature sensors, and/or thermal flow sensors. Typically, control unit 310 controls the extent to which the occlusion element occludes the vena cava and the rate at which the pump pumps blood, responsively to one or more of the parameters detected by the sensors. For example, based upon the parameters detected by the sensors, the control unit may control the extent to which the occlusion element occludes the vena cava and the rate at which the pump pumps blood in coordination with each other, such that the ratio between renal venous pressure and lower body pressure is a first ratio, and such that the ratio between central venous pressure and lower body pressure is a second ratio, which is different from the first ratio. Typically, the first ratio is designated based upon the extent to which it is desirable to decrease the subject's renal venous pressure, such as to increase renal perfusion, in accordance with the techniques described herein. Further typically, the second ratio is designated based upon the extent to which it is desirable to decrease the subject's cardiac preload, in accordance with the techniques described herein.

As noted hereinabove with respect to control unit 52, control unit 310 typically includes a computer processor that comprises circuitry and that is configured to execute the actions described herein. Typically, the operations described herein that are performed by the computer processor transform the physical state of a memory, which is a real physical article that is in communication with the computer processor, to have a different magnetic polarity, electrical charge, or the like, depending on the technology of the memory that is used. Control unit 310 is typically a hardware device programmed with computer program instructions to produce a special-purpose computer. For example, when programmed to perform the techniques described herein, control unit 310 typically acts as a special-purpose, preload-modulating computer processor. For some applications, a user interacts with the computer processor via a user interface 312, which is typically generally similar to user interface 54 described hereinabove.

Although some applications of the present invention are described with reference to blood pumps, according to which the blood pumps include impellers, the scope of the present invention includes using any other type of pump for pumping blood in the manner described herein, mutatis mutandis. For example, a roller pump, an Archimedes screw pump, a centrifugal pump, a pneumatic pump, and/or a compression pump may be used.

The scope of the present invention includes combining any of the apparatus and methods described herein with any of the apparatus and methods described in one or more of the following applications, all of which are incorporated herein by reference:

International Patent Application No. PCT/IL2017/051092 to Tuval, filed Sep. 28, 2017, entitled "Blood vessel tube," which U.S. Provisional Patent Application 62/401,403 to Tuval, filed Sep. 29, 2016;

International Patent Application No. PCT/IL2016/050525 to Schwammenthal (published as WO 16/185473), filed May 18, 2016, entitled "Blood pump," which claims priority from U.S. Provisional Patent Application 62/162,881 to Schwammenthal, filed May 18, 2015, entitled "Blood pump,"

US 2017/0100527 to Schwammenthal, which is the US national phase of International Patent Application PCT/IL2015/050532 to Schwammenthal (published as WO 15/177793), filed May 19, 2015, entitled "Blood pump," which claims priority from U.S. Provisional Patent Application 62/000,192 to Schwammenthal, filed May 19, 2014, entitled "Blood pump;"

US 2016/0022890 to Schwammenthal, which is the US national phase of International Patent Application PCT/IL2014/050289 to Schwammenthal (published as WO 14/141284), filed Mar. 13, 2014, entitled "Renal pump," which claims priority from (a) U.S. Provisional Patent Application 61/779,803 to Schwammenthal, filed Mar. 13, 2013, entitled "Renal pump," and (b) U.S. Provisional Patent Application 61/914,475 to Schwammenthal, filed Dec. 11, 2013, entitled "Renal pump;"

U.S. Pat. No. 9,764,113 to Tuval, issued Sep. 19, 2017, entitled "Curved catheter," which claims priority from U.S. Provisional Patent Application 61/914,470 to Tuval, filed Dec. 11, 2013, entitled "Curved catheter;" and U.S. Pat. No. 9,597,205 to Tuval, which is the US national phase of International Patent Application PCT/IL2013/050495 to Tuval (published as WO 13/183060), filed Jun. 6, 2013, entitled "Prosthetic renal valve," which claims priority from U.S. Provisional Patent Application 61/656,244 to Tuval, filed Jun. 6, 2012, entitled "Prosthetic renal valve."

There is therefore provided, in accordance with some applications of the present invention, the following inventive concepts:

Inventive concept 1. Apparatus comprising:

a catheter configured to be placed inside a blood vessel of a subject;

a first impeller configured to be inserted into the blood vessel via the catheter;

a first impeller cage configured to be disposed around the first impeller and to maintain a radial separation between the first impeller and an inner wall of the blood vessel;

a second impeller configured to be inserted into the blood vessel via the catheter, and to be placed within the blood vessel at a longitudinal separation from the first impeller;

a second impeller cage configured to be disposed around the second impeller and to maintain a radial separation between the second impeller and an inner wall of the blood vessel; and a support cage configured to be inserted into the blood vessel via the catheter, the support cage being configured to extend longitudinally along more than 50 percent of a region between the first and second impellers, the support cage being configured to thereby support an inner wall of the blood vessel in an open configuration in the region between the first and second impellers, a maximum diameter of the support cage when the support cage is in a non-constrained configuration thereof being at least 1.1 times greater than maximum diameters of each of the first and second impeller cages when the first and second impeller cages are in non-constrained configurations thereof.

Inventive concept 2. The apparatus according to inventive concept 1, wherein the maximum diameter of the support cage when the support cage is in the non-constrained configuration thereof is at least 1.3 times greater than maximum diameters of each of the first and second impeller cages when the first and second impeller cages are in non-constrained configurations thereof.

Inventive concept 3. The apparatus according to inventive concept 1, wherein a stiffness of each of the first and second impeller cages is at least 1.5 times greater than a stiffness of the support cage.

Inventive concept 4. The apparatus according to inventive concept 1, wherein the support cage is configured to extend at least from a longitudinal center of the first impeller to a longitudinal center of the second impeller.

Inventive concept 5. The apparatus according to inventive concept 1, wherein the first and second impeller cages are integrally formed with the support cage.

Inventive concept 6. The apparatus according to inventive concept 1, wherein the first and second impeller cages are separately formed from the support cage.

Inventive concept 7. The apparatus according to inventive concept 1, wherein the first and second impellers are configured to pump fluid in opposite directions from one another by the first and second impellers rotating in the same direction as one another, as viewed from an external reference point.

Inventive concept 8. The apparatus according to inventive concept 1, wherein the first and second impellers are configured to pump fluid in opposite directions from one another by the first and second impellers rotating in opposite directions from one another, as viewed from an external reference point.

Inventive concept 9. The apparatus according to any one of inventive concepts 1-8, wherein the first impeller is configured to be placed within a vena cava of the subject, such that the first impeller is disposed downstream of junctions of the vena cava with all renal veins of the subject, and the second impeller is configured to be placed inside the subject's vena cava, such that the second impeller is disposed upstream of junctions of the vena cava with all of the subject's renal veins.

Inventive concept 10. The apparatus according to inventive concept 9, wherein the catheter is configured to be placed within the subject's vena cava by being inserted via a femoral vein of the subject.

Inventive concept 11. The apparatus according to inventive concept 9, wherein the catheter is configured to be placed within the subject's vena cava by being inserted via a vein of the subject selected from the group consisting of: a subclavian vein, and a jugular vein.

Inventive concept 12. The apparatus according to inventive concept 9, further comprising a control unit configured to control rotation of the first and second impellers, wherein the first and second impellers are configured, by rotating, to lower pressure within the subject's renal veins by:

the first impeller pumping blood through the vena cava in a downstream direction, and the second impeller pumping blood through the vena cava in an upstream direction.

Inventive concept 13. The apparatus according to any one of inventive concepts 1-8, wherein the first and second impellers are configured to generate a region within the blood vessel that is of lower blood pressure than elsewhere within the blood vessel by pumping blood away from a region of the blood vessel between the first and second impellers.

Inventive concept 14. The apparatus according to inventive concept 13, wherein:

the catheter is configured to be placed within a main vein of a subject into which blood flows from a tributary venous system, the first impeller is configured to be placed in the main vein, downstream of the tributary venous system, and the second impeller is configured to be placed in the main vein, upstream of the tributary venous system.

Inventive concept 15. Apparatus comprising:

a catheter configured to be placed inside a blood vessel of a subject;

a first impeller configured to be inserted into the blood vessel via the catheter;

a first impeller cage configured to be disposed around the first impeller and to maintain a radial separation between the first impeller and an inner wall of the blood vessel;

a second impeller configured to be inserted into the blood vessel via the catheter, and to be placed within the blood vessel at a longitudinal separation from the first impeller;

a second impeller cage configured to be disposed around the second impeller and to maintain a radial separation between the second impeller and an inner wall of the blood vessel; and a support sleeve configured to be inserted into the blood vessel via the catheter, the support sleeve being configured to extend longitudinally along more than 50 percent of a region between the first and second impellers, the support sleeve being configured to thereby support an inner wall of the blood vessel in an open configuration in the region between the first and second impellers, and at least one end of the support sleeve being open such that the first impeller cage and the first impeller are able to pass through the open end of the support sleeve even when the first impeller cage and the first impeller are in radially non-constrained configurations thereof.

Inventive concept 16. The apparatus according to inventive concept 15, wherein the first and second impeller cages are separately formed from the support sleeve, and are configured to be inserted into the blood vessel subsequent to the support sleeve having been inserted into the blood vessel.

Inventive concept 17. The apparatus according to inventive concept 15, wherein, during insertion of the support sleeve into the blood vessel via the catheter, the support sleeve is configured to be crimped with the first and second impeller cages and the first and second impellers disposed inside the support sleeve, and wherein the open end of the support sleeve is configured not to be fixedly coupled to the first impeller or to the first impeller cage such that the open end of the support sleeve is able to undergo longitudinal movement with respect to the first impeller and first impeller cage.

Inventive concept 18. Apparatus comprising:

a catheter configured to be placed inside a blood vessel of a subject;

a first impeller configured to be inserted into the blood vessel via the catheter;

a first impeller cage configured to be disposed around the first impeller and to maintain a radial separation between the first impeller and an inner wall of the blood vessel;

a second impeller configured to be inserted into the blood vessel via the catheter, and to be placed within the blood vessel at a longitudinal separation from the first impeller;

a second impeller cage configured to be disposed around the second impeller and to maintain a radial separation between the second impeller and an inner wall of the blood vessel; and a support sleeve configured to be inserted into the blood vessel via the catheter, the support sleeve being configured to extend longitudinally along more than 50 percent of a region between the first and second impellers, the support sleeve being configured to thereby support an inner wall of the blood vessel in an open configuration in the region between the first and second impellers, the first impeller cage and the support sleeve being cut from a single piece of a shape memory alloy; and a cage assembly element configured to hold closed an end of the first impeller cage.

Inventive concept 19. The apparatus according to inventive concept 18, wherein the cage assembly element comprises a ring-shaped fastening element.

Inventive concept 20. Apparatus comprising:

a catheter configured to be placed within a vena cava of a subject;

a first impeller configured to be inserted into the vena cava via the catheter such that the first impeller is disposed, longitudinally, on a first side of junctions of the vena cava with all renal veins of the subject;

a second impeller configured to be inserted into the vena cava via the catheter such that the second impeller is disposed, longitudinally, on a second side of junctions of the vena cava with all renal veins of the subject;

a motor configured to generate rotational motion in a first direction;

a rotation shaft configured to extend from the motor to the first impeller and to impart the rotational motion in the first direction to the first impeller; and a gear mechanism disposed between the first and second impeller and configured to reverse a direction of rotational motion that is imparted from the first impeller to the second impeller, such that the second impeller rotates in an opposite direction of rotation to the first direction.

Inventive concept 21. Apparatus comprising:

a catheter configured to be placed within a vena cava of a subject;

a first impeller configured to be inserted into the vena cava via the catheter such that the first impeller is disposed, longitudinally, on a first side of junctions of the vena cava with all renal veins of the subject;

a second impeller configured to be inserted into the vena cava via the catheter such that the second impeller is disposed, longitudinally, on a second side of junctions of the vena cava with all renal veins of the subject;

a motor configured to rotate the first and second impellers in a given direction of rotation, the first and second impellers being of opposing-handedness with respect to one another, and being configured to be disposed within the vena cava such that the impellers face opposite directions from one another, such that the first and second impellers pump blood in opposite directions from one another by the first and second impellers being rotated in a given direction of rotation; and a third impeller disposed between the first and second impellers and configured to be rotated passively by blood that flows between the first and second impellers.

Inventive concept 22. The apparatus according to inventive concept 21, wherein the third impeller is configured, by being rotated passively by blood that flows between the first and second impellers, to reduce rotational motion of the blood that flows between the first and second impellers.

Inventive concept 23. Apparatus comprising:

a catheter configured to be placed within a vena cava of a subject, the catheter defining a catheter shaft;

a first impeller configured to be inserted into the vena cava via the catheter such that the first impeller is disposed, longitudinally, on a first side of junctions of the vena cava with all renal veins of the subject;

a second impeller configured to be inserted into the vena cava via the catheter such that the second impeller is disposed, longitudinally, on a second side of junctions of the vena cava with all renal veins of the subject;

a first motor configured to generate rotational motion in a first direction;

a first rotation shaft configured to extend from the first motor to the first impeller and to impart the rotational motion in the first direction to the first impeller;

a second motor configured to generate rotational motion in an opposite direction to the first direction;

a second rotation shaft configured to extend from the second motor to the second impeller and to impart the rotational motion in the opposite direction to the first direction to the second impeller, the first and second rotation shafts being coaxial with one another, within the catheter shaft.

Inventive concept 24. Apparatus for use with a guide catheter, the apparatus comprising:

a blood pump configured to be inserted into a renal vein of a subject and to pump blood from the renal vein to a vena cava of the subject, the blood pump being configured to be inserted into the renal vein via the guide catheter, while the blood pump is in a radially constrained configuration inside the guide catheter, and the blood pump being configured to assume a radially non-constrained configuration by being released from the guide catheter inside the subject's renal vein, the blood pump comprising:

an impeller configured, in the radially non-constrained configuration of the blood pump inside the subject's renal vein, to pump blood through the subject's renal vein by rotating;

an impeller cage disposed around the impeller, such that in the radially non-constrained configuration of the blood pump inside the subject's renal vein, the impeller is separated from an inner surface of the cage; and a plurality of support arms protruding radially from the cage, and configured to contact an inner wall of the renal vein, to thereby maintain a longitudinal axis of the impeller in greater alignment with a local longitudinal axis of the renal vein, relative to alignment of the longitudinal axis of the impeller with the local longitudinal axis of the renal vein in an absence of the support arms.

Inventive concept 25. The apparatus according to inventive concept 24, wherein the blood pump further comprises a pressure sensor, wherein the support arms are configured to maintain the pressure sensor at a distance of at least 2 mm from an inner wall of the blood vessel.

Inventive concept 26. Apparatus for use with a guide catheter, the apparatus comprising:

a blood pump configured to be inserted into a renal vein of a subject and to pump blood from the renal vein to a vena cava of the subject, the blood pump being configured to be inserted into the renal vein via the guide catheter, while the blood pump is in a radially constrained configuration inside the guide catheter, and the blood pump being configured to assume a radially non-constrained configuration by being released from the guide catheter inside the subject's renal vein, the blood pump comprising:

an impeller configured, in the radially non-constrained configuration of the blood pump inside the subject's renal vein, to pump blood through the subject's renal vein by rotating;

an impeller cage disposed around the impeller, such that in the radially non-constrained configuration of the blood pump inside the subject's renal vein, the impeller is separated from an inner surface of the cage, a stiffness of the impeller cage being sufficiently great that pressure exerted upon the impeller cage by an inner wall of the renal vein does not deform the impeller cage.

Inventive concept 27. The apparatus according to inventive concept 26, wherein the stiffness of the impeller cage is configured to permit the impeller cage to be inserted into the subject's renal vein by being crimped inside the guide catheter.

Inventive concept 28. The apparatus according to inventive concept 26, wherein the stiffness of the impeller cage is configured to permit the impeller cage to navigate turns while being advanced through the guide catheter.

Inventive concept 29. The apparatus according to any one of inventive concepts 26-28, wherein, in the radially non-constrained configuration of the blood pump, a diameter of the impeller cage, at a longitudinal location along the impeller cage at which the diameter of the impeller cage is at its maximum, is less than 12 mm.

Inventive concept 30. A method for increasing coronary blood supply of a subject, the method comprising:

inserting a blood pump into a location selected from the group consisting of: a coronary sinus of a subject, and a right atrium of the subject; and activating the blood pump to pump blood from the subject's right atrium into the subject's coronary sinus.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus, comprising:

an occlusion element configured to reduce cardiac preload of a subject by being placed in a vena cava of the subject at an infra-renal location, and to partially occlude the subject's vena cava at the infra-renal location;

one or more sensors configured to monitor one or more physiological parameters of the subject selected from the group consisting of: lower body venous pressure, central venous pressure, central venous blood flow, renal venous pressure, cardiac diameter, cardiac volume, arterial pressure, and arterial blood flow;

a computer processor configured to modulate an extent to which the occlusion element occludes the vena cava at the infra-renal location, responsively to the one or more physiological parameters; and a blood pump configured to be placed at a location within the vena cava that is downstream of junctions of the vena cava with all renal veins of the subject, the blood pump being configured to reduce the subject's renal venous pressure relative to the subject's central venous pressure by pumping blood in an antegrade direction through the vena cava from the location, and wherein the computer processor is further configured to modulate the rate at which the blood pump pumps blood in the antegrade direction responsively to the one or more physiological parameters in coordination with modulating the extent to which the vena cava is occluded at the infra-renal location responsively to the one or more physiological parameters, so as to:

maintain a first ratio between the subject's renal venous pressure and the subject's lower body venous pressure, and maintain a second ratio between the subject's central venous pressure and the subject's lower body venous pressure, the second ratio being different from the first ratio.

2. The apparatus according to claim 1, wherein the occlusion element comprises a balloon configured to be inflated at the infra-renal location, and wherein the computer processor is configured to modulate the extent to which the occlusion element occludes the vena cava at the infra-renal location by modulating an extent to which the balloon is inflated.

3. The apparatus according to claim 1, wherein the occlusion element comprises an expandable frame having material covered thereto, and wherein the computer processor is configured to modulate the extent to which the occlusion element occludes the vena cava at the infra-renal location by modulating an extent to which the frame is expanded.

4. The apparatus according to claim 1, wherein the one or more sensors are configured to monitor a parameter of the subject that is indicative of cardiac output of the subject, and wherein the computer processor is configured to modulate the extent to which the occlusion element occludes the vena cava at the infra-renal location responsively to the parameter that is indicative of the cardiac output.

5. The apparatus according to claim 4, wherein the one or more sensors comprise a thermodilution catheter configured to monitor the parameter that is indicative of the cardiac output.

6. The apparatus according to claim 4, wherein the one or more sensors are further configured to monitor a parameter of the subject that is indicative of cardiac preload of the subject, and wherein the computer processor is configured to modulate the extent to which the occlusion element occludes the vena cava at the infra-renal location responsively to the parameter that is indicative of the cardiac output in combination with the parameter that is indicative of the cardiac preload.

7. The apparatus according to claim 1, wherein the one or more sensors are configured to monitor a parameter of the subject that is indicative of arterial blood pressure of the subject, and wherein the computer processor is configured to modulate the extent to which the occlusion element occludes the vena cava at the infra-renal location responsively to the parameter that is indicative of the arterial blood pressure.

8. The apparatus according to claim 7, wherein the one or more sensors are further configured to monitor a parameter of the subject that is indicative of cardiac preload of the subject, and wherein the computer processor is configured to modulate the extent to which the occlusion element occludes the vena cava at the infra-renal location responsively to the parameter that is indicative of the arterial blood pressure in combination with the parameter that is indicative of the cardiac preload.

9. A method, comprising:

reducing cardiac preload of a subject by partially occluding a vena cava of the subject at an infra-renal location;

monitoring one or more physiological parameters of the subject selected from the group consisting of: lower body venous pressure, central venous pressure, central venous blood flow, renal venous pressure, cardiac diameter, cardiac volume, arterial pressure, and arterial blood flow, and modulating an extent to which the vena cava is occluded at the infra-renal location, responsively to the one or more physiological parameters;

reducing the subject's renal venous pressure relative to the subject's central venous pressure by pumping blood in an antegrade direction through the vena cava from a location within the vena cava that is downstream of junctions of the vena cava with all renal veins of the subject; and modulating a rate at which the blood is pumped responsively to the one or more physiological parameters in coordination with modulating the extent to which the vena cava is occluded at the infra-renal location responsively to the one or more physiological parameters, so as to:

maintain a first ratio between the subject's renal venous pressure and the subject's lower body venous pressure, and maintain a second ratio between the subject's central venous pressure and the subject's lower body venous pressure, the second ratio being different from the first ratio.

10. The method according to claim 9, wherein partially occluding the subject's vena cava at the infra-renal location comprises inflating a balloon at the infra-renal location, and wherein modulating an extent to which the vena cava is occluded at the infra-renal location comprises modulating an extent to which the balloon is inflated.

11. The method according to claim 9, wherein partially occluding the subject's vena cava at the infra-renal location comprises placing an expandable frame having material covered thereto at the infra-renal location and expanding the expandable frame, and wherein modulating an extent to which the vena cava is occluded at the infra-renal location comprises modulating an extent to which the frame is expanded.

12. The method according to claim 9, wherein partially occluding the subject's vena cava at the infra-renal location comprises placing a nozzle at the infra-renal location, and wherein modulating an extent to which the vena cava is occluded at the infra-renal location comprises modulating a diameter of an opening of the nozzle.

13. The method according to claim 9, wherein monitoring the one or more physiological parameters comprises monitoring a parameter that is indicative of cardiac output of the subject, and wherein modulating an extent to which the vena cava is occluded at the infra-renal location comprises modulating an extent to which the vena cava is occluded at the infra-renal location responsively to the parameter that is indicative of the cardiac output.

14. The method according to claim 13, wherein monitoring the parameter that is indicative of the cardiac output comprises using a thermodilution catheter to monitor the parameter that is indicative of the cardiac output.

15. The method according to claim 13, wherein monitoring the one or more physiological parameters further comprises monitoring a parameter that is indicative of cardiac preload of the subject, and wherein modulating an extent to which the vena cava is occluded at the infra-renal location comprises modulating an extent to which the vena cava is occluded at the infra-renal location responsively to the parameter that is indicative of the cardiac output in combination with the parameter that is indicative of the cardiac preload.

16. The method according to claim 9, wherein monitoring the one or more physiological parameters comprises monitoring a parameter that is indicative of arterial blood pressure of the subject, and wherein modulating an extent to which the vena cava is occluded at the infra-renal location comprises modulating an extent to which the vena cava is occluded at the infra-renal location responsively to the parameter that is indicative of the arterial blood pressure.

17. The method according to claim 16, wherein monitoring the one or more physiological parameters further comprises monitoring a parameter that is indicative of cardiac preload of the subject, and wherein modulating an extent to which the vena cava is occluded at the infra-renal location comprises modulating an extent to which the vena cava is occluded at the infra-renal location responsively to the parameter that is indicative of the arterial blood pressure in combination with the parameter that is indicative of the cardiac preload.

* * * * *